(12) United States Patent
Coburn et al.

(10) Patent No.: US 9,975,888 B2
(45) Date of Patent: May 22, 2018

(54) ARYL LINKED IMIDAZOLE AND TRIAZOLE DERIVATIVES AND METHODS OF USE THEREOF FOR IMPROVING THE PHARMACOKINETICS OF A DRUG

(71) Applicant: MERCK SHARP & DOHME CORP., Rahway, NJ (US)

(72) Inventors: Craig A. Coburn, Novato, CA (US); Milana M. Maletic, Summit, NJ (US); Yunfu Luo, Shanghai (CN); Zhiqi Qi, Shanghai (CN); Chun Sing Li, Shanghai (CN); Tingting Yu, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days. days.

(21) Appl. No.: 15/036,274

(22) PCT Filed: Nov. 7, 2014

(86) PCT No.: PCT/US2014/064461
§ 371 (c)(1),
(2) Date: May 12, 2016

(87) PCT Pub. No.: WO2015/073308
PCT Pub. Date: May 21, 2015

(65) Prior Publication Data
US 2016/0297809 A1     Oct. 13, 2016

(30) Foreign Application Priority Data

Nov. 12, 2013   (WO) ................ PCT/CN2013/086919

(51) Int. Cl.
| | |
|---|---|
| C07D 417/14 | (2006.01) |
| C07D 417/12 | (2006.01) |
| C07D 487/04 | (2006.01) |
| C07D 401/12 | (2006.01) |
| C07D 405/14 | (2006.01) |
| C07D 403/10 | (2006.01) |
| C07D 401/14 | (2006.01) |
| A61K 45/06 | (2006.01) |
| A61K 31/427 | (2006.01) |
| A61K 31/4439 | (2006.01) |
| A61K 31/454 | (2006.01) |
| A61K 31/4545 | (2006.01) |
| A61K 31/4725 | (2006.01) |
| A61K 31/496 | (2006.01) |
| A61K 31/4985 | (2006.01) |
| C07D 409/14 | (2006.01) |
| C07D 471/04 | (2006.01) |
| A61K 31/4178 | (2006.01) |
| A61K 31/5377 | (2006.01) |

(52) U.S. Cl.
CPC ........ *C07D 417/14* (2013.01); *A61K 31/4178* (2013.01); *A61K 31/427* (2013.01); *A61K 31/4439* (2013.01); *A61K 31/454* (2013.01);
*A61K 31/4545* (2013.01); *A61K 31/4725* (2013.01); *A61K 31/496* (2013.01); *A61K 31/4985* (2013.01); *A61K 31/5377* (2013.01); *A61K 45/06* (2013.01); *C07D 401/12* (2013.01); *C07D 401/14* (2013.01); *C07D 403/10* (2013.01); *C07D 405/14* (2013.01); *C07D 409/14* (2013.01); *C07D 417/12* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | |
|---|---|---|
| 7,550,463 B2 | 6/2009 | Yoshida |
| 7,919,488 B2 | 4/2011 | Planken et al. |
| 2009/0175820 A1 | 7/2009 | Desai et al. |

FOREIGN PATENT DOCUMENTS

| | | |
|---|---|---|
| WO | 2006108879 A2 | 10/2006 |
| WO | 2007034312 A2 | 3/2007 |
| WO | 2008010921 A2 | 1/2008 |
| WO | 2009016498 A1 | 2/2009 |
| WO | 2011008809 A1 | 1/2011 |
| WO | 2011042477 A1 | 4/2011 |
| WO | 2012064943 A2 | 5/2012 |

OTHER PUBLICATIONS

Sridhar et al. Molecules. ; 17(8): 9283-9305 (2013).*
CA Registry No. 1410586-03-6, entered into CA Registry File on Dec. 4, 2012, supplied by Aurora Fine Chemicals.*
CA Registry No. 1408376-28-2, entered into CA Registry File on Nov. 30, 2012, supplied by Aurora Fine Chemicals.*
Aurora Fine Chemicals Product Guide. 1 page, retrieved from the Internet at http://www.aurorafinechemicals.com/abouthtml on Apr. 28, 2015.*
Berge et al., "Pharmaceutical Salts", J. Pharm Sci., 1977, pp. 1-19, vol. 66, No. 1.
Bingham et al., "Over One Hundred Solvates of Sulfathiazole", Chem. Commun., 2001, pp. 603-604.
Bolm, C., et al, "a-Trialkylsily-Substituted a-Amino Acids", Angew. Chem. Int. Ed., 2000, pp. 2288-2290, vol. 39, No. 13.

(Continued)

*Primary Examiner* — Emily Bernhardt
(74) *Attorney, Agent, or Firm* — Jeffrey P. Bergman; Catherine D. Fitch

(57) ABSTRACT

The present invention relates to aryl linked imidazole and triazole derivatives, compositions comprising said compounds, alone or in combination with other drugs, and methods of using the compounds for improving the pharmacokinetics of a drug. The compounds of the invention are useful in human and veterinary medicine for inhibiting CYP3A4 and for improving the pharmacokinetics of a therapeutic compound that is metabolized by CYP3A4.

17 Claims, No Drawings

(56) References Cited

OTHER PUBLICATIONS

Caira et al., "Preparation and Crystal Characterization of a Polymorph,a Monohydrate, and an Ethyl Acetate Solvate of the Antifungal Fluconazole", J. Pharmaceutical Sci, 2004, pp. 601-611, vol. 93, No. 3.
Giralt, E., et al, "Replacement of a Proline With Silaproline Causes a 20-Fold Increase in the Cellular Uptake of a Pro-Rich Peptide", J. Am. Chem, Soc., 2006, p. 8479-8483, vol. 128.
Gould, P.L., "Salt Selections for Basic Drugs", Intl J. Pharmaceutics, 1986, pp. 201-217, vol. 33.
Green & Wuts, "Protective Groups in Organic Synthesis", 2nd Edition, 1991.
Greene, et al., "Protection for the Carbonyl Group", Organic Synthesis, 1999, pp. 312-344.
Johansson, T., et al, "In Vitro Metabolism of Haloperidol and Sila-Haloperidol: New Metabolic Pathways Resulting From Carbon/Silicon Exchange", Drug Metabolism and Disposition, 2010, pp. 78-83, vol. 38.
Masato Chiba, et al, "P450 Interaction With Farnesyl-Protein Transferase Inhibitors Metobolic Stability, Inhibitory Potency, and P450 Binding Spectra in Human Liver Microsomes", Biochemical Pharmacology, 2001 , 773-776, vol. 62, WO.
T. Higuchi and V. Stella, "Pro-drugs as Novel Delivery Systems", (1987) 14 of the A.C.S. Symposium Series.
Van Tonder, et al, "Preparation and Physicochemical Characterization of 5 Niclosamide Solvates and 1 Hemisolvate", AAPS Pharmscitech, 2004, pp. 1-10, vol. 5, No.
Pubchem. Compound Summary for CID 71149493: Create Date: Mar. 21, 2013 URL: https://pubchem.ncbi.nlm.nih.gov/compound/71149493?from=summary Retrieved from the Internet on Dec. 19, 2014.

* cited by examiner

ARYL LINKED IMIDAZOLE AND TRIAZOLE DERIVATIVES AND METHODS OF USE THEREOF FOR IMPROVING THE PHARMACOKINETICS OF A DRUG

CROSS-REFERENCE TO RELATED APPLICATIONS

This application is the national stage application under 35 U.S.C. 371 of International Patent Application No. PCT/US2014/064461, filed Nov. 7, 2014, which claims priority to International Patent Application No. PCT/CN2013/086919, filed Nov. 12, 2013. Each of the aforementioned PCT applications is incorporated by reference in its entirety.

BACKGROUND OF THE INVENTION

The cytochrome P450 enzyme system (CYP450) is responsible for the biotransformation of drugs from active substances to inactive metabolites that can be excreted from the body. In addition, the metabolism of certain drugs by CYP450 can alter their PK profile and result in sub-therapeutic plasma levels of those drugs over time. In the area of antiviral therapy, this can lead to resistance of the virus to the drug.

The virus causing acquired immunodeficiency syndrome (AIDS) is know by various names, including human immunodeficiency virus (HIV), of which two distinct families have been identified—HIV-1 and HIV-2. Many inhibitors of HIV, including HIV protease inhibitors, HIV integrase inhibitors and non-nucleoside reverse transcriptase inhibitors are metabolized by CYP450. This metabolic activity can lead to unfavorable pharmacokinetics, requiring administering more frequent and/or higher doses than are optimal.

Many drugs, including some HIV protease inhibitors, are now paired with other agents that improve exposure of the drug, with the drug-drug interaction being commonly referred to as "boosting." International Publication Nos. WO 2006/108879, WO 2007/034312 and WO 2008/010921; U.S. Patent Publication No. US 2009/0175820; and U.S. Pat. No. 7,919,488 describe compounds useful as pharmacokinetic enhancers.

Ritonavir, a common boosting agent, is widely used with HIV agents and is an HIV protease inhibitor itself that exerts its boosting effect through inhibition of Cytochrome P450 3A4 (CYP3A4) and p-glycoprotein drug transporters. Ritonavir, however, is associated with certain risks, including hepatotoxicity, hyperlipidemia and unfavorable gastrointestinal effects.

SUMMARY OF THE INVENTION

The present invention relates to aryl linked imidazole and triazole derivatives, compositions comprising said compounds, alone or in combination with other drugs, and methods of using the compounds for improving the pharmacokinetics of a drug. The compounds of the invention are useful in human and veterinary medicine for inhibiting CYP3A4 and for improving the pharmacokinetics of a therapeutic compound that is metabolized by CYP3A4.

DETAILED DESCRIPTION OF THE INVENTION

The invention encompasses a compound of formula (I):

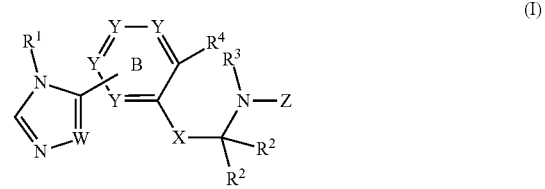

(I)

or a pharmaceutically acceptable salt thereof, wherein:

Z is selected from (1) H, (2) $C_1$-$C_6$ alkyl, (3) —$SO_2$—($C_1$-$C_6$ alkyl), (4) —C(O)—O—($C_1$-$C_6$ alkyl), (5) —C(O)—N($R^8$)—($C_1$-$C_6$ alkyl), (6) , (7) 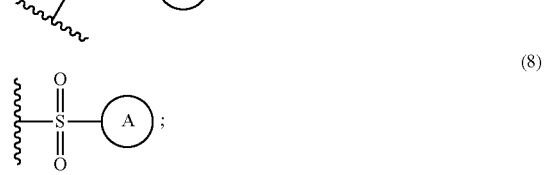, and (8)

A is selected from $C_3$-$C_6$ cycloalkyl, aryl, 5 or 6-membered heteroaryl, 5 or 6-membered monocyclic heterocycloalkyl and 9 or 10-membered bicyclic heterocycloalkyl, each of which is optionally substituted with up to four $R^5$ groups;

each W and each Y are independently —N= or —CH=, provided that at least one Y is —CH=;

X is a bond or —C($R^2$)($R^2$)—;

$R^1$ is selected from —($C_1$-$C_6$ alkylene)-aryl, —($C_1$-$C_6$ alkylene)-(5 or 6-membered heteroaryl), —($C_1$-$C_6$ alkylene)-O-aryl, —($C_1$-$C_6$ alkylene)-O-(5 or 6-membered heteroaryl) and $C_3$-$C_6$ cycloalkyl, wherein any aryl, heteroaryl or $C_3$-$C_6$ cycloalkyl group can be optionally substituted with up to four $R^9$ groups, which can be the same or different, and wherein said $C_3$-$C_6$ cycloalkyl group can be fused to a benzene ring and said fused benzene ring can be optionally substituted with up to four $R^9$ groups, which can be the same or different;

each occurrence of $R^2$ is independently selected from H, $C_1$-$C_6$ alkyl, —OH, —O—($C_1$-$C_6$ alkyl) and —($C_1$-$C_6$ alkylene)-O—($C_1$-$C_6$ alkyl); or two $R^2$ groups on the same carbon atom can be joined together to form a cyclopropyl group;

R³ is selected from H and C₁-C₆ alkyl, or R³ and an R² group, together with the atoms to which they are attached, can combine to form a C₃-C₆ heterocyclic ring;

R⁴ is H, or R³ and R⁴ can join together to form a linker group selected from —CH₂— and —CH₂—CH₂—, thereby forming a fused monocylic ring with ring B;

each occurrence of R⁵ is independently selected from halo, —OR⁸, —N(R⁶)₂—, —(C₁-C₆ alkylene)-N(R⁶)₂—, 5 or 6-membered monocyclic heterocycloalkyl or 9 or 10-membered bicyclic heterocycloalkyl, wherein said 5 or 6-membered monocyclic heterocycloalkyl group can optionally form a spirocycle with a C₃-C₆ cycloalkyl group or another 5 or 6-membered monocyclic heterocycloalkyl group, and wherein said 5 or 6-membered monocyclic heterocycloalkyl group and said 9 or 10-membered bicyclic heterocycloalkyl group can be optionally substituted on one or more ring carbon atoms with up to four R⁷ groups, which can be the same or different, and wherein a ring carbon atom of a 5 or 6-membered monocyclic heterocycloalkyl group may be functionalized as a carbonyl group each occurrence of R⁶ is independently selected from H, C₁-C₆ alkyl, C₁-C₆ hydroxyalkyl, C₃-C₆ cycloalkyl, C₃-C₆ cyclohydroxyalkyl, —C(O)—C₁-C₆ alkyl, —(C₁-C₆ alkylene)-O—C₁-C₆ alkyl, —C(O)-aryl, or 5 or 6-membered heteroaryl, wherein said C₁-C₆ alkyl group is optionally substituted with 1 or 2 groups, each independently being NH₂ or halo, and wherein said 5 or 6-membered heteroaryl group can be optionally substituted with up to four R⁷ groups;

each occurrence of R⁷ and each occurrence of R⁹ is independently selected from C₁-C₆ alkyl, 5 or 6-membered heterocycloalkyl, C₁-C₆ hydroxyalkyl, C₁-C₆ haloalkyl, halo, —CN, —N(R⁸)₂, —CH₂N(R⁸)₂, —OR⁸, —C(O)OR⁸, —SR⁸, —S(O)₂R⁸ and —C(O)N(R⁸)₂, wherein said 5 or 6-membered heterocycloalkyl group can be optionally substituted with a group selected from C₁-C₆ alkyl, halo, C₁-C₆ hydroxyalkyl, C₁-C₆ haloalkyl, halo, —CN, —N(R⁸)₂ and —OR⁸; and each occurrence of R⁸ is independently H or C₁-C₆ alkyl ("Embodiment E1").

The imidazole (when W═CH) or triazole (when W═N) group depicted in Formula (I) can be substituted at any substitutable position on ring B. For example when the variable Y is —CH═, the imidazole or triazole group can be substituted on the carbon atom by replacing the hydrogen atom.

In another embodiment ("Embodiment E2"), the invention encompasses a compound of Formula (I) as described in Embodiment E1, or a pharmaceutically acceptable salt thereof, wherein the A ring within the definition of Z is selected from: cyclopropyl, phenyl, benxo[d][1,3]dioxol-5-yl, tetrahydro-2H-pyran-2-yl, thiazolyl, pyridyl and pyrazinyl, each of which is optionally substituted with up to two R⁵ groups, and all other variable are defined as in Embodiment E1.

In another embodiment ("Embodiment E3"), the invention encompasses a compound of Formula (I) as described in Embodiment E1, or a pharmaceutically acceptable salt thereof, wherein: each W and each Y is —CH═; X is a bond; and R¹ is

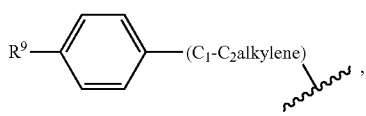

wherein the —(C₁-C₂alkylene)-linker depicted is straight or branched, and all other variable are defined as in Embodiment E1 or Embodiment E2.

For purposes of this specification, the straight chained —(C₁-C₂alkylene)-linker is —CH₂—CH₂—; the branched chained —(C₁-C₂alkylene)-linker is —CH(CH₃)—, In another embodiment ("Embodiment E4"), the invention encompasses a compound of formula (Ia):

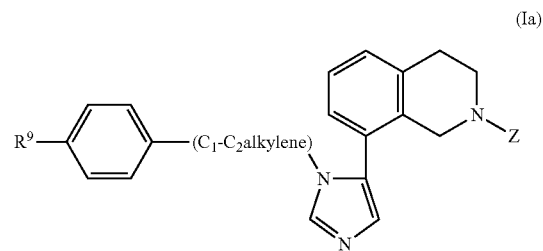

(Ia)

or a pharmaceutically acceptable salt thereof, wherein the —(C₁-C₂alkylene)-linker depicted in formula (Ia) is straight or branched, R⁹ is defined as in Embodiment E1 and Z is as defined in Embodiment E1 or Embodiment E2.

In another embodiment ("Embodiment E5"), the invention encompasses a compound of formula (Ia) as described in Embodiment E4, or a pharmaceutically acceptable salt thereof, wherein:

Z is

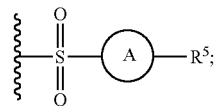

R⁹ is —F, R⁵ is defined as in Embodiment E1 and A is defined as in Embodiment E1 or Embodiment E2.

In another embodiment ("Embodiment E6"), the invention encompasses a compound of formula (Ia) as described in Embodiment 4, or a pharmaceutically acceptable salt thereof, wherein: Z and R⁹ are defined as in Embodiment E5, A is thiazol-2-yl or pyridin-3-yl, and R⁵ is selected from —N(H)—C(O)—C₁-C₄alkyl, 4-methylpiperazin-1-yl, 4-(2-hydroxyethyl)piperazin-1-yl, 4-hydroxypiperadin-1-yl and 7-hydroxyhexadydropyrrolo[1,2-a]pyrazin-2(1H)-yl.

In another embodiment ("Embodiment E7"), the invention encompasses a compound of formula (Ib):

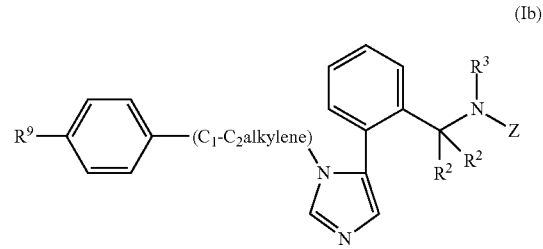

(Ib)

or a pharmaceutically acceptable salt thereof, wherein the —(C₁-C₂alkylene)-linker depicted in formula (Ib) is straight or branched, R⁹ is defined as in Embodiment E1 and Z is as defined in Embodiment E1 or Embodiment E2.

In another embodiment ("Embodiment E8"), the invention encompasses a compound of formula (Ib) as described in Embodiment E7, or a pharmaceutically acceptable salt thereof, wherein:
Z is

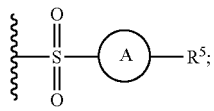

$R^9$ is —F, $R^5$ is defined as in Embodiment E1 and A is defined as in Embodiment E1 or Embodiment E2.

In another embodiment ("Embodiment E9"), the invention encompasses a compound of formula (Ib) as described in Embodiment E7, or a pharmaceutically acceptable salt thereof, wherein: Z and $R^9$ are defined as in Embodiment E8, A is thiazol-2-yl or pyridin-3-yl, and $R^5$ is selected from —N(H)—C(O)—$C_1$-$C_4$alkyl, 4-methylpiperazin-1-yl, 4-(2-hydroxyethyl)piperazin-1-yl, 4-hydroxypiperadin-1-yl and 7-hydroxyhexadydropyrrolo[1,2-a]pyrazin-2(1H)-yl.

In another embodiment ("Embodiment E10"), the invention encompasses a compound of formula (Ic):

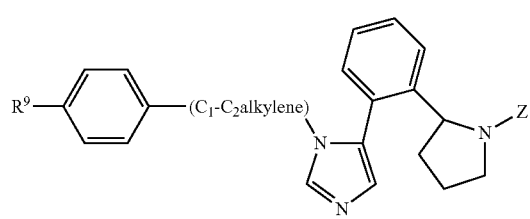

(Ic)

or a pharmaceutically acceptable salt thereof, wherein the —($C_1$-$C_2$alkylene)-linker depicted in formula (Ic) is straight or branched, $R^9$ is defined as in Embodiment E1 and Z is as defined in Embodiment E1 or Embodiment E2.

In another embodiment ("Embodiment E11"), the invention encompasses a compound of formula (Ic) as described in Embodiment E10, or a pharmaceutically acceptable salt thereof, wherein:
Z is

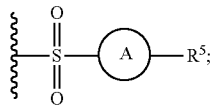

and
$R^9$ is —F, $R^5$ is defined as in Embodiment E1 and A is defined as in Embodiment E1 or Embodiment E2.

In another embodiment ("Embodiment E12"), the invention encompasses a compound of formula (Ic) as described in Embodiment E10, or a pharmaceutically acceptable salt thereof, wherein: Z and $R^9$ are defined as in Embodiment E11, A is thiazol-2-yl or pyridin-3-yl, and $R^5$ is selected from —N(H)—C(O)—$C_1$-$C_4$alkyl, 4-methylpiperazin-1-yl, 4-(2-hydroxyethyl)piperazin-1-yl, 4-hydroxypiperadin-1-yl and 7-hydroxyhexadydropyrrolo[1,2-a]pyrazin-2(1H)-yl.

In another embodiment ("Embodiment E13"), the invention encompasses a compound of formula (Id):

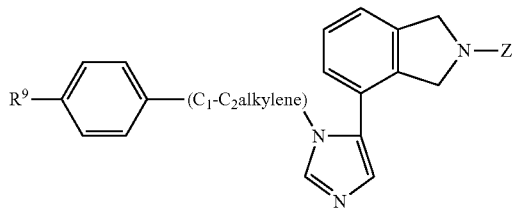

(Id)

or a pharmaceutically acceptable salt thereof, wherein the —($C_1$-$C_2$alkylene)-linker depicted in formula (Id) is straight or branched, $R^9$ is defined as in Embodiment E1 and Z is as defined in Embodiment E1 or Embodiment E2.

In another embodiment ("Embodiment E14"), the invention encompasses a compound of formula (Id) as described in Embodiment E13, or a pharmaceutically acceptable salt thereof, wherein:
Z is

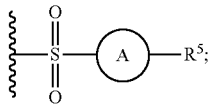

$R^9$ is —F, $R^5$ is defined as in Embodiment E1 and A is defined as in Embodiment E1 or Embodiment E2.

In another embodiment ("Embodiment E15"), the invention encompasses a compound of formula (Id) as described in Embodiment E13, or a pharmaceutically acceptable salt thereof, wherein: Z and $R^9$ are defined as in Embodiment E14, A is thiazol-2-yl or pyridin-3-yl, and $R^5$ is selected from —N(H)—C(O)—$C_1$-$C_4$alkyl, 4-methylpiperazin-1-yl, 4-(2-hydroxyethyl)piperazin-1-yl, 4-hydroxypiperadin-1-yl and 7-hydroxyhexadydropyrrolo[1,2-a]pyrazin-2(1H)-yl.

In another embodiment ("Embodiment E16"), the invention encompasses a compound of formula (Ia) as described in Embodiment E4, a compound of formula (Ib) as described in Embodiment E7, a compound of formula (Ic) as described in Embodiment E10 or a compound of formula (Id) as described in Embodiment E13, or a pharmaceutically acceptable salt of any of the foregoing, wherein:
Z is

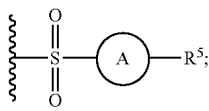

$R^5$ is selected from:

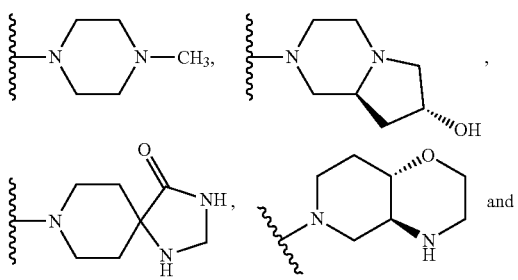

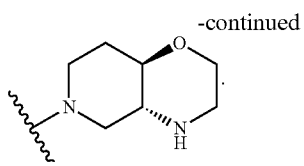

and $R^9$ is defined as in Embodiment E1 or $R^9$ is —F.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising one or more therapeutic compounds that are metabolized by CYP3A, preferably CYP3A4.

(c) The pharmaceutical composition of (b), wherein the therapeutic compound is an anti-HIV drug, preferably the anti-HIV drug(s) are selected from the group consisting of HIV protease inhibitors, HIV integrase inhibitors nucleoside reverse transcriptase inhibitors and non-nucleoside reverse-transcriptase inhibitors.

(d) A pharmaceutical combination that is (i) a Compound of Formula (I) and ii) a therapeutic compound metabolized by CYP3A4 that is an anti-HIV drug; wherein the Compound of Formula (I) and the therapeutic compound metabolized by CYP3A4 are each employed in an amount that renders the combination effective for inhibiting HIV replication, or for treating HIV infection and/or reducing the likelihood or severity of symptoms of HIV infection.

(e) The combination of (d), wherein the therapeutic compound metabolized by CYP3A4 is selected from the group consisting of HIV protease inhibitors, HIV integrase inhibitors, nucleoside reverse transcriptase inhibitors and non-nucleoside reverse-transcriptase inhibitors.

(f) A method of inhibiting HIV replication in a subject in need thereof which comprises administering to the subject: (i) a Compound of Formula (I) and (ii) one or more anti-HIV drugs, wherein the amounts of the Compound of Formula (I) and the anti-HIV drug(s) are together effective to inhibit HIV replication.

(g) A method of treating HIV infection and/or reducing the likelihood or severity of symptoms of HIV infection in a subject in need thereof which comprises administering to the subject (i) a Compound of Formula (I) and (ii) one or more anti-HIV drugs, wherein the amounts of the Compound of Formula (I) and the anti-HIV drug(s) are together effective to treat HIV infection.

(h) The method of (h), wherein the anti-HIV drug(s) are an selected from the group consisting of HIV protease inhibitors, HIV integrase inhibitors, nucleoside reverse transcriptase inhibitors and non-nucleoside reverse-transcriptase inhibitors.

(i) A method of inhibiting HIV replication in a subject in need thereof which comprises administering to the subject the pharmaceutical composition of (c) or the combination of (d) or (e).

(j) A method of treating HIV infection and/or reducing the likelihood or severity of symptoms of HIV infection in a subject in need thereof which comprises administering to the subject the pharmaceutical composition of (b) or (c) or the combination of (d) or (e).

Additional embodiments of the invention include the pharmaceutical compositions, combinations and methods set forth in (a)-(j) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (j) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 1-72 as set forth below, and pharmaceutically acceptable salts thereof.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In still another embodiment, the subject is a dog, cat, horse, pig, hamster or other companion animal.

The term "effective amount" as used herein, refers to: (i) an amount administered of a Compound of Formula (I), or pharmaceutically acceptable salt thereof, that is effective for inhibiting CYP3A4 in a subject, (ii) the amounts administered of each of a combination of: (A) a Compound of Formula (I), or pharmaceutically acceptable salt thereof, and (B) a therapeutic compound metabolized by CYP3A4 wherein the amounts administered are together effective in producing the desired therapeutic, ameliorative, inhibitory or preventative effect when administered to a subject. In one embodiment the patient is suffering from HIV infection or AIDS and the therapeutic compound is an anti-HIV agent. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —CH$_2$—. The term "$C_1$-$C_6$ alkylene" refers to an alkylene group having from 1 to 6 carbon atoms. The term "$C_3$-$C_5$ alkylene" refers to an alkylene group having from 3 to 5 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH═CH—, —CH═CHCH$_2$—, —CH$_2$CH═CH—, —CH$_2$CH═CHCH$_2$—, —CH═CHCH$_2$CH$_2$—, —CH$_2$CH$_2$CH═CH— and —CH(CH$_3$)CH═CH—. In one embodiment, an alkenylene group has from 2 to about 6 carbon atoms. In another embodiment, an alkenylene group has from about 3 to about 5 carbon atoms. In another embodiment, an alkenylene group is branched. In another embodiment, an alkenylene group is linear. The term "$C_2$-$C_6$ alkylene" refers to an alkenylene group having from 2 to 6 carbon atoms. The term "$C_3$-$C_5$ alkenylene" refers to an alkenylene group having from 3 to 5 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein. In one embodiment, a cycloalkyl group is unsubstituted. The term "3 to 6-membered cycloalkyl" refers to a cycloalkyl group having from 3 to 6 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

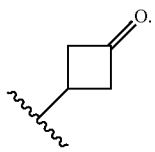

The term "CYP3A," as used herein, refers to the all the known members of the 3A subfamily of the cytochrome P450 superfamily of genes. CYP3A includes, but is not limited to CYP3A4, CYP3A5, CYP3A7 and CYP3A43. In one embodiment, the CYP3A gene is CYP3A4.

The term "halo," as used herein, means —F, —Cl, —Br or —I. In one embodiment, the halo group is F.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, the heterocycloalkyl group is bicyclic and has 9 or 10 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

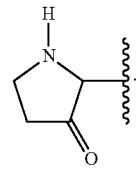

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "HIV," as used herein, refers generically to all known species of the HIV virus, including, but not limited to, HIV-1 and HIV-2.

The term "ring system substituent," as used herein, refers to a substituent group attached to an aromatic or non-aromatic ring system which, for example, replaces an available hydrogen on the ring system. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

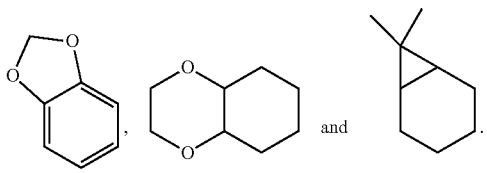

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., C$_1$-C$_6$ alkyl, R$^2$, R$^8$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Compound of Formula (I) or a pharmaceutically acceptable salt of the compound. The transformation may occur by various mechanisms (e.g., by metabolic or chemical processes), such as, for example, through hydrolysis in blood.

For example, if a Compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$)alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—(C$_1$-C$_2$)alkylamino(C$_2$-C$_3$)alkyl (such as β-dimethylaminoethyl), carbamoyl-(C$_1$-C$_2$)alkyl, N,N-di(C$_1$-C$_2$)alkylcarbamoyl-(C$_1$-C$_2$)alkyl and piperidino-, pyrrolidino- or morpholino(C$_2$-C$_3$)alkyl, and the like. Similarly, if a Compound of Formula (I) contains an alcohol functional group, a prodrug can be formed by the replacement of one or more of the hydrogen atoms of the alcohol groups with a group such as, for example, (C$_1$-C$_6$)alkanoyloxymethyl, 1-((C$_1$-C$_6$)alkanoyloxy)ethyl, 1-methyl-1-((C$_1$-C$_6$)alkanoyloxy) ethyl, (C$_1$-C$_6$)alkoxycarbonyloxymethyl, N—(C$_1$-C$_6$) alkoxycarbonylaminomethyl, succinoyl, (C$_1$-C$_6$)alkanoyl, α-amino(C$_1$-C$_4$)alkyl, α-amino(C$_1$-C$_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate) or a phosphate of structure PO$_3$M$_2$ where M is either sodium or potassium.

If a Compound of Formula (I) incorporates an amine functional group, a prodrug can be formed by the replacement of a hydrogen atom in the amine group with a group such as, for example, R-carbonyl-, RO-carbonyl-, NRR'-carbonyl- wherein R and R' are each independently (C$_1$-C$_{10}$) alkyl, (C$_3$-C$_7$) cycloalkyl, benzyl, a natural α-aminoacyl, —C(OH)C(O)OY$^1$ wherein Y$^1$ is H, (C$_1$-C$_6$)alkyl or benzyl, —C(OY$^2$)Y$^3$ wherein Y$^2$ is (C$_1$-C$_4$)alkyl and Y$^3$ is (C$_1$-C$_6$) alkyl; carboxy (C$_1$-C$_6$)alkyl; amino(C$_1$-C$_4$)alkyl or mono-N— or di-N,N—(C$_1$-C$_6$)alkylaminoalkyl; —C(Y$^4$)Y$^5$ wherein Y$^4$ is H or methyl and Y$^5$ is mono-N— or di-N, N—(C$_1$-C$_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Compounds of Formula (I) can form salts which are also within the scope of this invention. Reference to a Compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Compounds of Formula (I) may be atropisomers (e.g., substituted biaryls) and are considered as part of this invention. Enantiomers can also be directly separated using chiral chromatographic techniques.

It is also possible that the Compounds of Formula (I) may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Compound of Formula (I) incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Compounds of Formula (I), and of the salts, solvates, hydrates, esters and prodrugs of the Compounds of Formula (I), are intended to be included in the present invention.

The following abbreviations are used below and have the following meanings: AcOH is acetic acid; Boc is tert-butyloxycarbonyl, (Boc)$_2$O or Boc$_2$O is Boc anhydride; n-BuLi is n-butyl lithium; t-BuNO$_2$ or t-BuONO is tert-butyl nitrite; Cbz is carboxybenzyl; DCM is dichloromethane; DIEA is N,N-diisopropylethylamine; DMF is dimethylformamide; DMSO is dimethylsulfoxide; EtOAc is ethyl acetate; EtOH is ethanol; Et$_3$N or TEA is triethylamine; HMPA is hexamethylphosphoramide; HOAc is acetic acid; HPLC is high-pressure liquid chromatography; KSCN is potassium thiocyanate; LCMS is liquid chromatography-mass spectrometry; LDA is lithium diisopropylamide; MeCN is acetonitrile; MeI is iodomethane; MeOH is methanol; MS is mass spectroscopy; NaBH(OAc)$_3$ is sodium triacetoxy borohydride; NMR is nuclear magnetic resonance spectroscopy; PCy$_3$ is tricyclohexylphosphine; Pd(OAc)$_2$ is palladium(II) acetate; Pd$_2$(dba)$_3$ is tris dibenzylideneacetone dipalladium; PE is petroleum ether; PG is protecting group; Pd/C is palladium on carbon; Prep is preparative; rt is room temperature; TBAF is n-tetrabutylammonium fluoride; TFA is trifluoroacetic acid; TLC is thin-layer chromatography; TMSCN is trimethylsilyl cyanide; Ts is 4-toluenesulfonyl; THF is tetrahydrofuran; wt % is percentage by weight; and X-phos is 2-dicyclohexylphosphino-2',4',6'-triisopropylbiphenyl.

Uses of the Piperidine or Piperazine Imidazole and Triazole Derivatives

The compounds of the invention are useful in human and veterinary medicine for inhibiting CYP3A4. In addition, the compounds of the invention are useful for improving the pharmacokinetics of a therapeutic compound that is metabolized by CYP3A4.

The present invention provides novel compounds of Formula (I) that inhibit CYP3A. Uses of the compounds of Formula (I) described herein include inhibiting CYP3A, which may be useful for increasing the pharmacokinetics of compounds that are metabolized by CYP3A.

The present invention also encompasses the use of a Compound of Formula (I) for inhibiting CYP3A4 in a subject, said method comprising administering to said subject a Compound of Formula (I), or pharmaceutically acceptable salt thereof, in an amount that is effective to inhibit CYP3A4 in said subject.

The present invention also encompasses the use of a Compound of Formula (I) for the manufacture of a medicament useful for inhibiting CYP3A4 in a subject.

Inhibition of CYP3A4

The present invention provides methods for inhibiting CYP3A4 in a subject, said method comprising administering to said subject a Compound of Formula (I), or pharmaceutically acceptable salt thereof, in an amount that is effective to inhibit CYP3A4 in said subject.

The present invention also provides methods that may be, or are believed to be, useful for inhibiting other members of CYP3A in a subject, said method comprising administering to said subject a Compound of Formula I, or pharmaceutically acceptable salt thereof, in an amount that is effective to inhibit CYP3A in said subject. In one embodiment, the CYP3A being inhibited is CYP3A5. In another embodiment, the CYP3A being inhibited is CYP3A7. In another embodiment, the CYP3A being inhibited is CYP3A4.

Improving the Pharmacokinetics of a Therapeutic Compound that is Metabolized by CYP3A4

The present invention provides methods for improving the pharmacokinetics of a therapeutic compound that is metabolized by CYP3A4, comprising administering to a subject in need of such treatment an effective amount of a combination of said therapeutic compound and a Compound of Formula (I) or pharmaceutically acceptable salt thereof.

The present invention also provides methods that may be, or are believed to be, useful for improving the pharmacokinetics of a therapeutic compound that is metabolized by other members of CYP3A, comprising administering to a subject in need of such treatment an effective amount of a combination of said therapeutic compound and a Compound of Formula (I) or pharmaceutically acceptable salt thereof. In one embodiment, the therapeutic compound is metabolized by CYP3A5. In another embodiment, the therapeutic compound is metabolized by CYP3A7. In another embodiment, the therapeutic compound is metabolized by CYP3A43.

In one embodiment, the therapeutic compound whose pharmacokinetics are being improved is an anti-HIV drug.

In another embodiment, the therapeutic compound whose pharmacokinetics are being improved is an HIV protease inhibitor.

In still another embodiment, the therapeutic compound whose pharmacokinetics are being improved is an HIV integrase inhibitor.

In another embodiment, the therapeutic compound whose pharmacokinetics are being improved is a nucleoside reverse transcriptase inhibitor (nRTI).

In yet another embodiment, the therapeutic compound whose pharmacokinetics are being improved is a non-nucleoside reverse transcriptase inhibitor (nnRTI).

Treatment or Prevention of HIV Infection

The present invention provides methods for treating or preventing HIV infection in a subject comprising administering to the subject: (i) a Compound of Formula (I) or a pharmaceutically acceptable salt thereof and (ii) one or more anti-HIV drugs, wherein the amounts administered are together effective to treat or prevent HIV infection in said subject. In one embodiment, the present invention also provides methods for treating AIDS in a subject comprising administering to the subject: (i) a Compound of Formula (I) or a pharmaceutically acceptable salt thereof and (ii) one or more anti-HIV drugs, wherein the amounts administered are together effective to treat AIDS in said subject.

The compositions and combinations of the present invention can be useful for treating a subject suffering from infection related to any HIV genotype.

In one embodiment, the HIV infection being treated is HIV-1.

In another embodiment, the HIV infection being treated is HIV-2.

In another embodiment, the HIV infection being treated has transformed into AIDS.

Combination Therapy

When administering a combination of a Compound of Formula (I) and one or more anti-HIV drugs to a subject, the Compound of Formula (I) and anti-HIV drug may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Compound of Formula (I) and the anti-HIV drug(s) may be present in fixed amounts (dosage amounts) in a single dosage unit (e.g., a capsule, a tablet, and the like).

In one embodiment, the Compound of Formula (I) is administered during a time when the anti-HIV drug(s) exert their prophylactic or therapeutic effect, or vice versa.

In another embodiment, when administered in combination with a Compound of Formula (I), the anti-HIV drug(s) are administered in doses lower than the doses commonly employed when such agents are used as monotherapy for treating HIV infection. A lower dosage or less frequent administration of the the anti-HIV drug(s) may reduce the toxicity of therapy without reducing the efficacy of therapy.

In one embodiment, the at least one Compound of Formula (I) and the anti-HIV drug(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

In one embodiment, the administration of a Compound of Formula (I) and the anti-HIV drug(s) may inhibit the resistance of the HIV infection to one or more of the agents being administered.

Anti-HIV Drugs

An "anti-HIV drug," as defined herein, is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV drug is effective in treating, preventing, or delaying the onset or progression of HIV infection or AIDS and/or diseases or conditions arising therefrom or associated therewith. For example, the Compounds of Formula (I) can be effectively administered, whether at periods of pre-exposure and/or post-exposure, in combination with effective amounts of one or more anti-HIV drugs selected from anti-HIV drugs, imunomodulators, antiinfectives, useful for treating HIV infection or AIDS. HIV antivirals are listed in Table A below.

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| CMX-157 | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| Dolutegravir | PI |
| efavirenz, EFV, Sustiva ®, Stocrin ® | nnRTI |
| efavirenz + emtricitabine + tenofovir DF, Atripla ® | nnRTI + nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| raltegravir, MK-0518, Isentress ® | InI |
| rilpivirine, TMC-278 | nnRTI |
| Rilpivirine + emtricitabine + tenofovir, Complera | nnRTI + nRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor.
Some of the drugs listed in the table are used in a salt form; e.g., abacavir sulfate, indinavir sulfate, atazanavir sulfate, nelfmavir mesylate.

In one embodiment, the one or more anti-HIV drugs are selected from raltegravir, lamivudine, abacavir, ritonavir, dolutegravir, atazanavir, elvitegravir and lopinavir.

In still another embodiment, the compound of formula (I) is used in combination with an anti-HIV drug which is atazanavir, and optionally one or more additional anti-HIV drugs.

In another embodiment, the compound of formula (I) is used in combination with an anti-HIV drug which is darunavir, and optionally one or more additional anti-HIV drugs.

In another embodiment, the compound of formula (I) is used in combination with at least two anti-HIV drugs which are darunavir and raltegravir.

In another embodiment, the compound of formula (I) is used in combination with at least two anti-HIV drugs which are atazanavir and raltegravir.

In still another embodiment, the compound of formula (I) is used in combination with at least two anti-HIV drugs which are ritonavir and lopinavir.

In another embodiment, the compound of formula (I) is used in combination with at least three anti-HIV drug which are lopinavir, ritonavir and raltegravir.

In one embodiment, the present invention provides pharmaceutical compositions comprising (i) a compound of formula (I) or a pharmaceutically acceptable salt thereof; (ii) a pharmaceutically acceptable carrier; and (iii) one or more additional anti-HIV drugs selected from lamivudine, abacavir, ritonavir and lopinavir, or a pharmaceutically acceptable salt thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt thereof and (ii) one or more additional anti-HIV drugs selected from raltegravir, lamivudine, abacavir, atazanavir, darunavir, ritonavir and lopinavir, or a pharmaceutically acceptable salt thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV drugs is not limited to the HIV antivirals listed in Table A, but includes in principle any combination with any drug or pharmaceutical composition useful for the treatment or prophylaxis of AIDS. The anti-HIV drugs and other agents will typically be employed in these combinations in their conventional dosage ranges and regimens as reported in the art, including, for example, the dosages described in the *Physicians' Desk Reference*, Thomson P D R, Thomson P D R, 57$^{th}$ edition (2003), the 58$^{th}$ edition (2004), the 59$^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the Compound(s) of Formula (I) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Compositions and Administration

Due to their activity, the Compounds of Formula (I) are useful in veterinary and human medicine. As described above, the Compounds of Formula (I) are useful for: inhibiting CYP3A4; improving the pharmacokinetics of a therapeutic compound that is metabolized by CYP3A4; and in combination with one or more anti-HIV agents for treating or preventing HIV infection in a subject in need thereof.

When administered to a subject, the Compounds of Formula (I) can be administered as a component of a composition that comprises a pharmaceutically acceptable carrier or vehicle. The present invention provides pharmaceutical compositions comprising an effective amount of at least one Compound of Formula (I) and a pharmaceutically acceptable carrier. In the pharmaceutical compositions and methods of the present invention, the active ingredients will typically be administered in admixture with suitable carrier materials suitably selected with respect to the intended form of administration, e.g., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, e.g., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the Compounds of Formula (I) are administered orally.

In another embodiment, the Compounds of Formula (I) are administered intravenously.

In one embodiment, the present invention provides compositions comprising a Compound of Formula (I) or a pharmaceutically acceptable salt thereof, and a pharmaceutically acceptable carrier.

In one embodiment, a pharmaceutical preparation comprising at least one Compounds of Formula (I) is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Compound(s) of Formula (I) by weight or volume. In various embodiments, the present compositions can contain, in one embodiment, from about 1% to about 70% or from about 5% to about 60% of the Compound(s) of Formula (I) by weight or volume.

The Compounds of Formula (I) can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Compounds of Formula (I) will be regulated according to the judgment of the attending clinician considering such factors as age, condition and size of the subject as well as severity of the symptoms being treated. The compositions of the invention can further comprise one or more additional therapeutic agents, selected from those listed above herein. Accordingly, in one embodiment, the present invention provides compositions comprising: (i) a Compound of Formula (I) or a pharmaceutically acceptable salt thereof; (ii) a therapeutic compound that is metabolized by CYP3A4; and (iii) a pharmaceutically acceptable carrier. In another embodiment, the present invention provides compositions comprising: (i) a Compound of Formula (I) or a pharmaceutically acceptable salt thereof; (ii) one or more anti-HIV drugs; and (iii) a pharmaceutically acceptable carrier, wherein the amounts in the composition are together effective to treat HIV infection.

In another embodiment, the present invention provides compositions comprising a Compound of Formula (I) or a pharmaceutically acceptable salt thereof, a pharmaceutically acceptable carrier, and one or more anti-HIV drugs, wherein said anti-HIV drugs are selected from raltegravir, lamivudine, abacavir, atazanavir, darunavir, lopinavir and ritonavir.

In still embodiment, the present invention provides compositions comprising a Compound of Formula (I) or a pharmaceutically acceptable salt thereof, a pharmaceutically acceptable carrier, and raltegravir.

Kits

In one aspect, the present invention provides a kit comprising a therapeutically effective amount of at least one Compound of Formula (I), or a pharmaceutically acceptable salt, solvate, ester or prodrug of said compound and a pharmaceutically acceptable carrier, vehicle or diluent.

In another aspect the present invention provides a kit comprising an amount of at least one Compound of Formula (I), or a pharmaceutically acceptable salt, solvate, ester or prodrug of said compound and a therapeutic compound that is metabolized by CYP3A4. In one embodiment, the Compounds of Formula (I) and the therapeutic compound that is metabolized by CYP3A4 are provided in the same container. In one embodiment, the Compounds of Formula (I) and the therapeutic compound that is metabolized by CYP3A4 are provided in separate containers.

In another aspect the present invention provides a kit comprising an amount of at least one Compound of Formula (I), or a pharmaceutically acceptable salt, solvate, ester or prodrug of said compound and an amount of at least one anti-HIV drug listed above, wherein the amounts of the two or more active ingredients result in a desired therapeutic effect. In one embodiment, the Compounds of Formula (I) and the one or more anti-HIV drugs are provided in the same container. In one embodiment, the Compounds of Formula (I) and the one or more anti-HIV drugs are provided in separate containers.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below. Alternative synthetic pathways and analogous structures will be apparent to those skilled in the art of organic synthesis.

One skilled in the art of organic synthesis will recognize that the synthesis of the Compounds of Formula (I) may require protection of certain functional groups (i.e., derivatization for the purpose of chemical compatibility with a particular reaction condition). Suitable protecting groups for the various functional groups of these compounds and methods for their installation and removal are well known in the art of organic chemistry. A summary of many of these methods can be found in Greene et al., *Protective Groups in Organic Synthesis*, Wiley-Interscience, New York, (1999).

One skilled in the art of organic synthesis will also recognize that one route for the synthesis of the Compounds of Formula (I) may be more desirable depending on the choice of appendage substituents. Additionally, one skilled in the art will recognize that in some cases the order of reactions may differ from that presented herein to avoid functional group incompatibilities and thus adjust the synthetic route accordingly.

The preparation of some intermediates useful for making the Compounds of Formula (I) have been described in the literature and in compendia such as "Comprehensive Heterocyclic Chemistry" editions I, II and III, published by Elsevier and edited by A. R. Katritzky & R. J K Taylor. Manipulation of the required substitution patterns have also been described in the available chemical literature as summarized in compendia such as "Comprehensive Organic Chemistry" published by Elsevier and edited by D H R. Barton and W. D. Ollis; "Comprehensive Organic Functional Group Transformations" edited by edited by A. R. Katritzky & R. J K Taylor and "Comprehensive Organic Transformation" published by Wily-CVH and edited by R. C. Larock.

The Compounds Formula (I) may contain one or more silicon atoms. The compounds contemplated in this invention in general can be prepared using the carba-analog methodology unless otherwise noted. A recent review of the synthesis of silicon containing compounds can be found in "Silicon Chemistry: from Atom to Extended Systems", Ed P. Jutzi & U. Schubet; ISBN 978-3-527-30647-3. Preparation of silyl containing amino acids has been described. See Bolm et al., *Angew. Chem. Int Ed.*, 39:2289 (2000). Descriptions of improved cellular update (Giralt, J. Am. Chem. Soc., 128:8479 (2006)) and reduced metabolic processing of silyl containing compounds have been described (Johansson et al., *Drug Metabolism & Disposition*, 38:73 (2009)).

The starting materials used and the intermediates prepared using the methods set forth in Schemes A-L may be isolated and purified if desired using conventional techniques, including but not limited to filtration, distillation, crystallization, chromatography and alike. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Varian VNMR System 400 (400 MHz) and are reported as ppm downfield from Me$_4$Si with number of protons, multiplicities, and coupling constants in Hertz indicated parenthetically. Where LC/MS data are presented, analyses was performed using an Agilent 6110A MSD or an Applied Biosystems API-100 mass spectrometer and Shimadzu SCL-10A LC column: Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of petroleum ether/ethyl acetate, from 100% petroleum ether to 100% ethyl acetate.

Example 1

N-(5-((6-(1-(4-fluorophenethyl)-1H-imidazol-5-yl)-3,4-dihydroisoquinolin-2(1H)-yl)sulfonyl)thiazol-2-yl)acetamide (Compound 1)

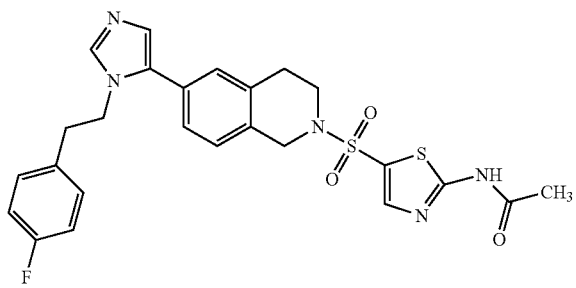 [SMILES: CC(=O)Nc1ncc(S(=O)(=O)N2CCc3cc(-c4cncn4CCc4ccc(F)cc4)ccc3C2)s1]

Step A—Preparation of Int 1-1

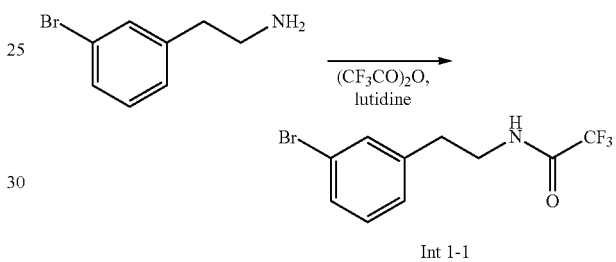

To a solution of m-bromophenethyl amine (20 g, 100 mmol) in DCM (400 mL) was added lutidine (11.8 g, 110 mmol) and trifluoroacetic anhydride (23.1 g, 110 mmol). The mixture was stirred at room temperature overnight. The reaction mixture was washed with HCl solution (aq. 1M), water and then followed by 10% NaHCO$_3$ solution. The organic phase was separated and was dried over Na$_2$SO$_4$ then evaporated to give 23 g of the crude product Int 1-1 as yellow oil which was used directly without further purification. $^1$H NMR (CDCl$_3$) δ: 7.30-7.40 (m, 2H), 7.00-7.20 (m, 3H), 3.54 (q, J=6.8 Hz, 2H), 2.83 (t, J=7.2 Hz, 2H), 2.53 (s, 1H). MS-ESI (m/z): 296 (M+H)$^+$.

Step B—Preparation of Int 1-2

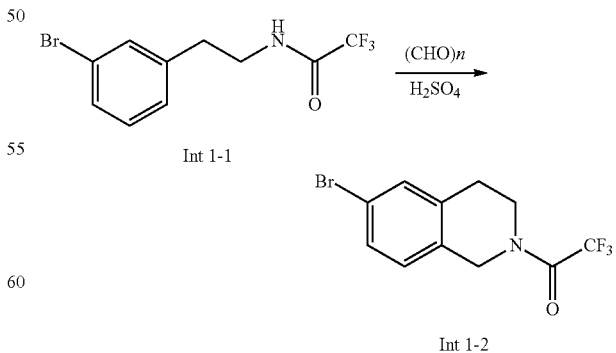

To a solution of compound Int 1-1 (3 g, 10 mmol) in HOAc (16.5 mL) was added paraformaldehyde (1.83 g, 20 mmol) and concentrated H$_2$SO$_4$ (11 mL) dropwise at 0° C.

The mixture was stirred at room temperature overnight. The reaction mixture was poured into ice water and diluted with water, and then extracted with EtOAc (3×50 mL). The combined organic extracts were washed with brine, dried over Na₂SO₄ and evaporated to dryness. The crude product of compound Int 1-2 (3 g) was used directly without further purification. ¹H NMR (CDCl₃) δ: 6.90-7.50 (m, 3H), 4.60-4.65 (m, 2H), 3.75-3.85 (m, 2H), 2.85-2.95 (m, 2H). MS-ESI (m/z): 309 (M+H)⁺.

Step C—Preparation of Int 1-3

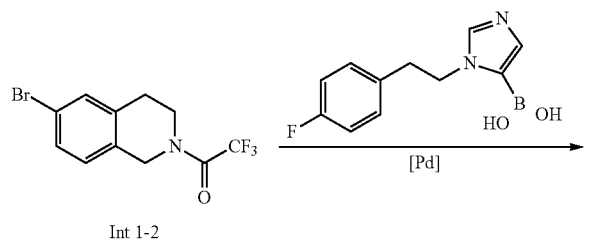

Int 1-2

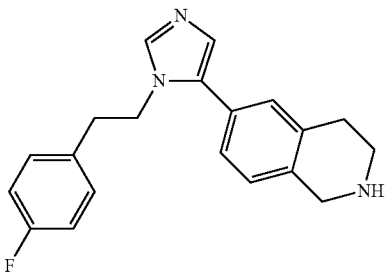

Int 1-4

To a solution of compound Int 1-3 (260 mg, 0.62 mmol) in MeOH (10 mL) was added K₂CO₃ (260 mg, 1.87 mmol) and water (2.5 mL). The mixture was stirred at room temperature for 2 h. The reaction mixture was concentrated and neutralized by 1M HCl and extracted with EtOAc (3×20 mL). The combined organic extracts were washed with brine, dried over Na₂SO₄ and evaporated to dryness to afford the crude product (150 mg) used directly without further purification. MS-ESI (m/z): 322.2 (M+H)⁺.

Step D—Preparation of Compound 1

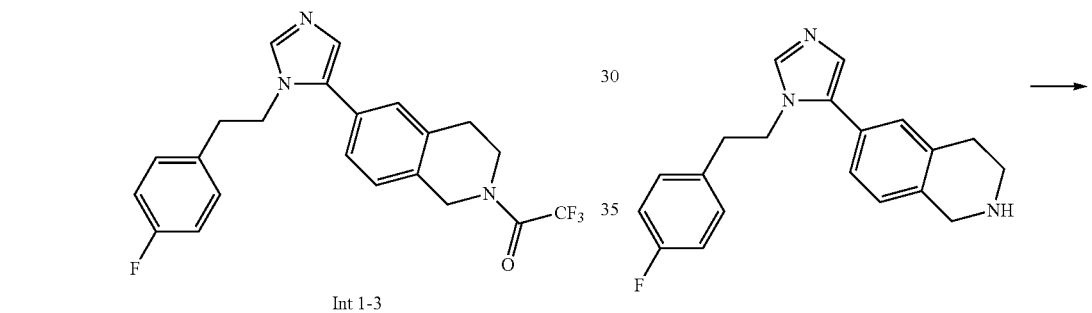

To a solution of compound Int 1-2 (200 mg, 0.65 mmol) in dioxane (5 mL) was added corresponding (1-(4-fluorophenethyl)-1H-imidazol-5-yl)boronic acid (150 mg, 0.65 mmol), Pd₂(dba)₃ (60 mg, 0.065 mmol), XantPhos (100 mg, 0.13 mmol) and K₂CO₃ (180 mg, 1.30 mmol). The mixture was stirred at 90° C. overnight under N₂. The reaction mixture was cooled and filtered then evaporated to dryness. The crude product was purified by silica gel chromatography eluting with petroleum ether/EtOAc=1:1 to afford compound Int 1-3 (260 mg) as white solid. MS-ESI (m/z): 418 (M+H)⁺.

Step D—Preparation of Int 1-4

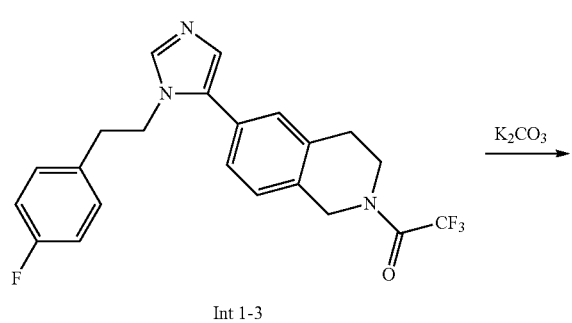

Int 1-3

To a solution of compound Int 1-4 (150 mg, 0.47 mmol) in DMF (4 mL) was added Et₃N (0.5 mL) and 2-acetamidothiazole-5-sulfonyl chloride (150 mg). The mixture was stirred for 1 h at ambient temperature. The mixture was filtered and purified by preparative HPLC to afford Compound 1 as white solid. ¹H NMR (CD₃OD) δ: 8.75 (s, 1H), 7.96 (s, 1H), 7.47 (s, 1H), 7.30-7.35 (m, 1H), 7.20-7.25 (m, 1H), 7.08 (s, 1H), 6.85-6.95 (m, 4H), 4.46 (t, J=6.8 Hz, 2H), 4.42 (s, 2H), 3.48 (t, J=6.8 Hz, 2H), 2.95-3.05 (m, 2H), 2.80-2.90 (m, 2H), 2.18 (s, 3H). MS-ESI (m/z): 634 (M+H)⁻.

The following compound—was prepared using a protocol similar to that described in Example 1 above.

| Cmpd | Structure | IUPAC name | M + 1 | ¹H NMR |
|---|---|---|---|---|
| 2 | 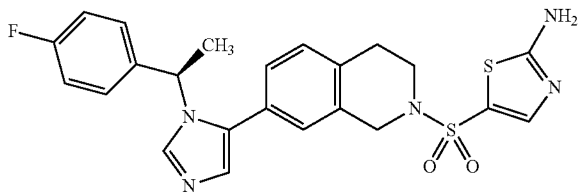 [SMILES: C[C@H](c1ccc(F)cc1)n1cncc1-c1ccc2c(c1)CN(S(=O)(=O)c1cnc(N)s1)CC2] | (R)-5-((7-(1-(1-(4-fluorophenyl)ethyl)-1H-imidazol-5-yl)-3,4-dihydroisoquinolin-2(1H)-yl)sulfonyl)thiazol-2-amine | 484 | CD₃OD: δ 8.09 (s, 1H), 7.39 (s, 1H), 7.06 (d, J = 8.0 Hz, 1H), 6.98 (s, 1H), 6.92~6.83 (m, 6H), 5.37 (q, J = 7.6 Hz, 1H), 4.13 (q, J = 16 Hz, 2H), 3.30 (t, J = 5.6 Hz, 2H), 2.86 (t, J = 5.6 Hz, 2H), 1.74(d, J = 7.2 Hz, 3H). |

Example 3

N-(1-(4-(1-(4-fluorophenethyl)-1H-imidazol-5-yl)phenyl)ethyl)-2-(4-methylpiperazin-1-yl)thiazole-5-sulfonamide (Compound 3)

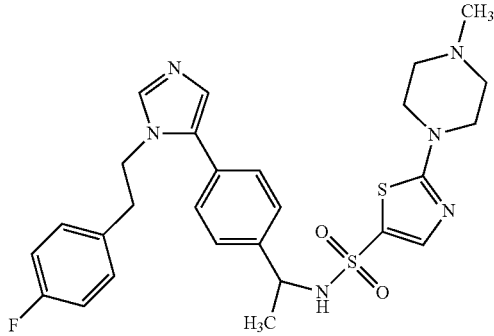 [SMILES: CC(NS(=O)(=O)c1cnc(N2CCN(C)CC2)s1)c1ccc(-c2cncn2CCc2ccc(F)cc2)cc1]

Step A—Preparation of Int 3-1

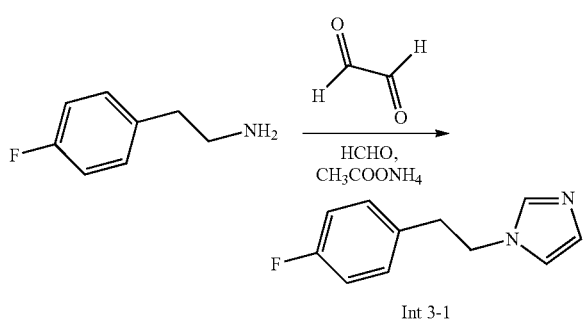

To a solution of 4-fluorophenethylamine (60 g, 0.43 mol) in MeOH (600 mL) was added formaldehyde (37.97 g, 0.86 mol), oxaldehyde (50.0 g, 0.86 mol) and ammonium acetate (66.4 g, 0.86 mol). The resulting mixture was heated to reflux overnight. After cooling to room temperature the mixture was concentrated under reduce pressure. The residue was diluted with water (150 mL) and extracted with EtOAc (3×150 mL). The combined organic extracts were washed with water (150 mL) and brine (150 mL), then dried, filtered and concentrated under reduced pressure. The residue was purified by column chromatography (Petroleum Ether/EtOAc=1/1) to afford 12 g of Int 3-1 as a white solid. MS (ESI) m/z 191 (M+H)⁺

Step B—Preparation of Int 3-2

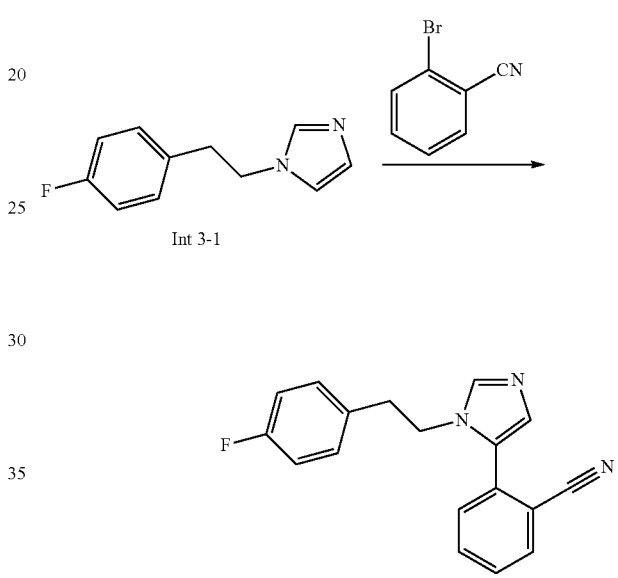

To a solution of Int 3-1 (4.0 g, 21 mmol) in DMF (60 mL) was added 2-bromobenzonitrile (4.59 g, 25.2 mmol), K₂CO₃ (8.7 g, 63 mmol), Cy₃P (1.18 g, 4.2 mmol) and Pd(OAc)₂ (471 mg, 2.1 mmol) under a nitrogen atmosphere. The sealed vial was irradiated in the microwave on a Biotage Smith Synthesizer at 160° C. for 1 h. The mixture was cooled to ambient temperature then diluted with water (180 mL) and extracted with EtOAc (3×60 mL). The combined organic extracts were dried, filtered and concentrated. The residue was purified by column chromatography (Petroleum Ether:EtOAc=2/3) to afford 1.8 g of the desired product. MS (ESI) m/z 292 (M+H)⁺

Step C—Preparation of Int 3-3

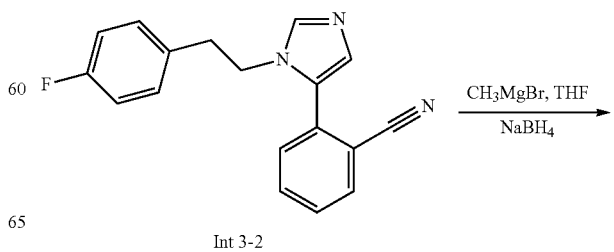

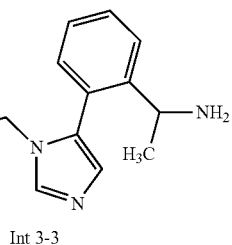

Int 3-3

To a solution of Int 3-2 (1.0 g, 3.43 mmol) in THF (15 mL) was added CH₃MgBr (2.04 g, 17.2 mmol) at 0° C. under a nitrogen atmosphere. The mixture was allowed to warm to 90° C. and stirred for 3 h. The mixture was cooled to 0° C. and NaBH$_4$ (260 mg, 6.86 mmol) in MeOH (5 mL) was added. The mixture was stirred at 90° C. for another 5 h. The mixture was then cooled to room temperature and diluted with water (20 mL) then washed with 1M HCl (3×10 mL). The aqueous washings were extracted with EtOAc (3×20 mL) and the pH was adjusted with NaHCO$_3$ until pH=7. The aqueous was then extracted with EtOAc (3×20 mL) and the combined organic extracts were dried, filtered and concentrated. The residue was purified by column chromatography (Petroleum Ether/EtOAc=1/1) to afford the product Int 3-3 (278 mg). MS (ESI) m/z 310 (M+H)⁺

Step D—Preparation of Compound 3

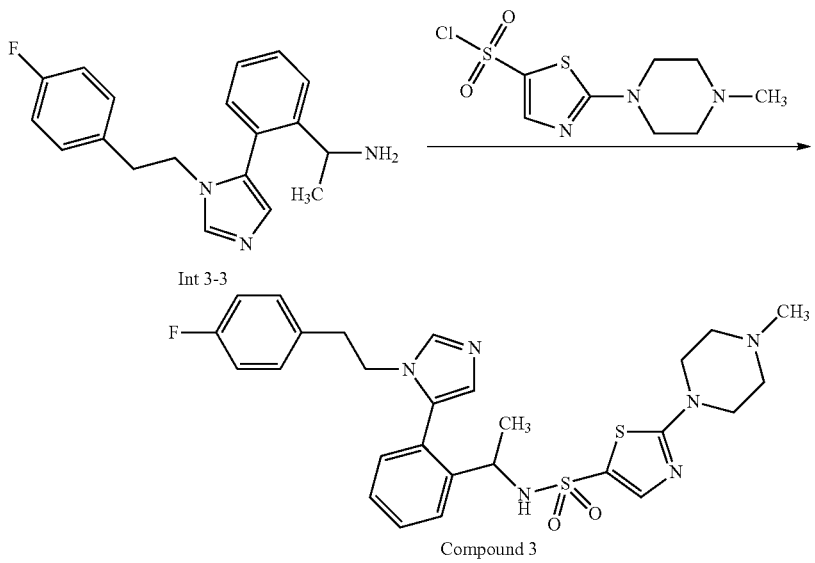

To a solution of Int 3-3 (10 mg, 0.027 mmol) in DMF (2 mL) were added 2,6-lutidine (8.6 mg, 0.08 mmol), DMAP (16.5 mg, 0.135 mmol) and 2-(4-methylpiperazin-1-yl)thiazole-5-sulfonyl chloride (15 mg, 0.027 mmol) at 0° C. The resulting mixture was stirred at room temperature overnight. The mixture was purified by HPLC to afford the desired product Compound 3. ¹H NMR (CD$_3$OD) δ: 8.98 (s, 1H), 7.52-7.62 (br, 3H), 7.38-7.43 (m, 1H), 7.37 (s, 1H), 6.98-7.15 (m, 5H), 4.37 (q, J=6.8 Hz, 1H), 4.05-4.30 (m, 2H), 3.79 (br, 4H), 3.40 (br, 4H), 3.01-3.12 (m, 2H), 2.96 (s, 3H), 1.30 (d, J=6.8 Hz, 3H). MS (ESI) m/z 555 (M+H)⁺.

The following compounds 4-7 were prepared using a protocol similar to that described in Example 3 above.

| Cmpd | Structure | IUPAC name | M + 1 | ¹H NMR |
|---|---|---|---|---|
| 4 | (structure shown) | N-(1-(2-(1-(4-fluorophenethyl)-1H-imidazol-5-yl)phenyl)ethyl)-N-methyl-2-(4-methylpiperazin-1-yl)thiazole-5-sulfonamide | 569.3 | (CD$_3$OD) δ: 8.95 (s, 1H), 7.57-7.45 (br, 3H), 7.34-7.43 (m, 1H), 7.37 (s, 1H), 6.99-7.15 (m, 5H), 4.37 (q, J = 6.8 Hz, 1H), 4.05-4.30 (m, 2H), 3.79 (br, 4H), 3.40 (br, 4H), 3.01-3.12 (m, 2H), 2.96 (s, 3H), 2.66 (s, 3H), 1.28 (d, J = 6.8 Hz, 3H). |

-continued

| Cmpd | Structure | IUPAC name | M + 1 | ¹H NMR |
|---|---|---|---|---|
| 5 | 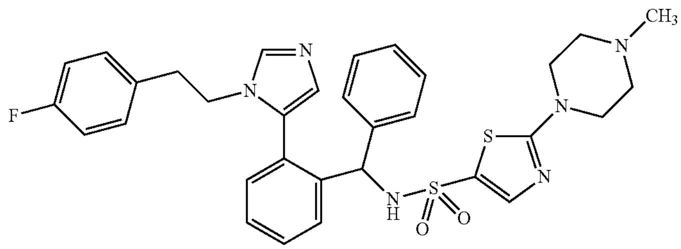 [SMILES: CN1CCN(c2ncc(S(=O)(=O)NC(c3ccccc3)c3ccccc3-c3cncn3CCc3ccc(F)cc3)s2)CC1] | N-((2-(1-(4-fluorophenethyl)-1H-imidazol-5-yl)phenyl)(phenyl)methyl)-2-(4-methylpiperazin-1-yl)thiazole-5-sulfonamide | 619.2 | (CD₃OD) δ: 9.03 (br, 1H) 7.52 (br 2H) 7.43 (t, J = 7.6 Hz, 1H), 6.83-7.30 (m, 12H), 5.57 (s, 1H), 4.08-4.46 (m, 2H), 3.68 (br, 4H), 3.36 (br, 4H), 3.15 (br, 2H), 2.94 (s, 3H). |
| 6a | 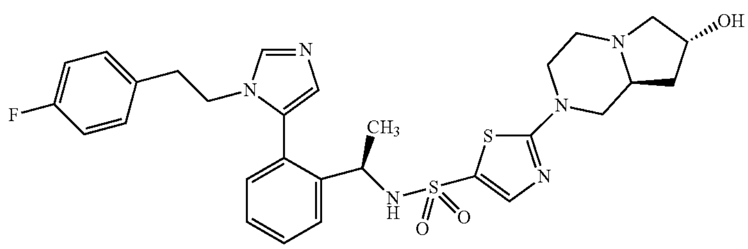 [SMILES: C[C@@H](NS(=O)(=O)c1cnc(N2CCN3C[C@H](O)C[C@H]3C2)s1)c1ccccc1-c1cncn1CCc1ccc(F)cc1] | N-((R)-1-(2-(1-(4-fluorophenethyl)-1H-imidazol-5-yl)phenyl)ethyl)-2-((7R,8aS)-7-hydroxy-hexahydro-pyrrolo[1,2-a]pyrazin-2(1H)-yl)thiazole-5-sulfonamide | 597.2 | (CD₃OD) δ: 7.83 (s, 1H), 7.64 (s, 1H), 7.51-7.54 (m, 1H), 7.37 (s, 2H), 7.05-7.07 (m, 6H), 4.49 (s, 2H), 4.07-4.09 (m, 3H), 3.89-3.93 (m, 1H), 3.56-3.57 (m, 2H), 2.90-3.15 (m, 4H), 2.47-2.54 (m, 2H), 2.26-2.27 (m, 1H), 1.88 (s, 2H), 1.34 (s, 3H). |
| 6b | 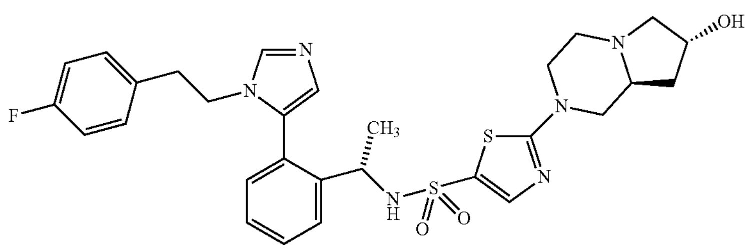 [SMILES: C[C@H](NS(=O)(=O)c1cnc(N2CCN3C[C@H](O)C[C@H]3C2)s1)c1ccccc1-c1cncn1CCc1ccc(F)cc1] | N-((S)-1-(2-(1-(4-fluorophenethyl)-1H-imidazol-5-yl)phenyl)ethyl)-2-((7R,8aS)-7-hydroxy-hexahydro-pyrrolo[1,2-a]pyrazin-2(1H)-yl)thiazole-5-sulfonamide | 597.2 | (CD₃OD) δ: 7.72 (s, 1H), 7.53 (d, J = 7.6 Hz, 1H), 7.42 (t, J = 7.2 Hz, 1H), 7.28 (t, J = 7.2 Hz, 1H), 7.25 (s, 1H), 6.92-7.00 (m, 6H), 4.36-4.41 (m, 2H), 3.95-4.01 (m, 3H), 3.77-3.81 (m, 1H), 3.45-3.49 (m, 1H), 3.11-3.17 (m, 1H), 3.03-3.06 (m, 1H), 2.90 (q, J = 6.8 Hz, 2H), 2.78 (t, J = 11.2 Hz, 1H), 2.33-2.45 (m, 2H), 2.14-2.18 (m, 1H), 1.75-1.79 (m, 2H), 1.24 (d, J = 11.2 Hz, 3H). |
| 7 | 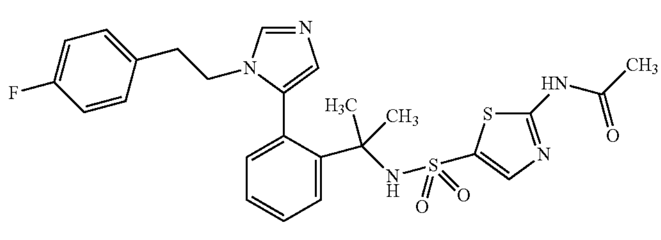 [SMILES: CC(=O)Nc1ncc(S(=O)(=O)NC(C)(C)c2ccccc2-c2cncn2CCc2ccc(F)cc2)s1] | N-(5-(N-(2-(2-(1-(4-fluorophenethyl)-1H-imidazol-5-yl)phenyl)propan-2-yl)sulfamoyl)thiazol-2-yl)acetamide | 528.1 | (CD₃OD) δ: 7.78 (br, 1H), 7.66 (d, J = 8 Hz, 1H), 7.6 (s, 1H), 7.36 (t, J = 7.2 Hz, 1H), 7.21 (t, J = 7.2 Hz, 1H), 6.85-7.16 (m, 5H), 6.76 (d, J = 7.2 Hz, 1H), 4.06-4.19 (m, 1H), 3.78-3.90 (m, 1H), 2.95-3.08 (m, 2H), 2.22 (s, 3H), 1.41 (s, 6H). |

Example 8

N-(5-((2-(4-(1-(4-fluorophenethyl)-1H-imidazol-5-yl)phenyl)pyrrolidin-1-yl)sulfonyl)thiazol-2-yl)acetamide (Compound 8)

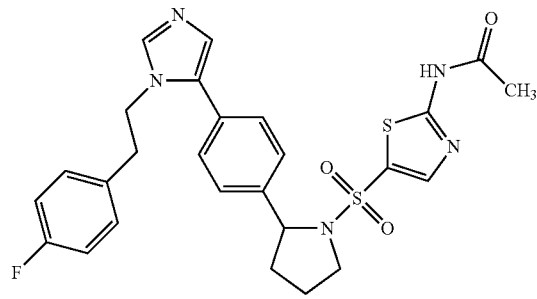 [SMILES: CC(=O)Nc1ncc(S(=O)(=O)N2CCCC2c2ccc(-c3cncn3CCc3ccc(F)cc3)cc2)s1]

Step A—Preparation of Int 8-1

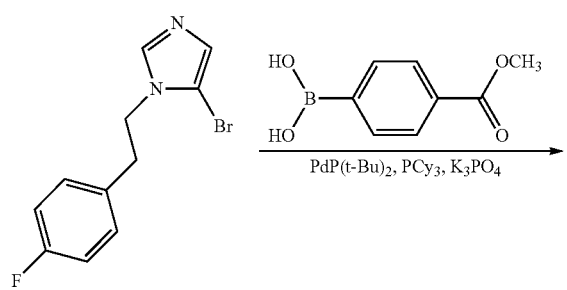

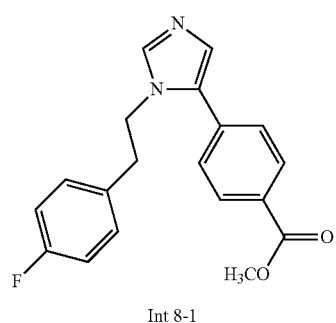

To a stirred solution of 5-bromo-1-(4-fluorophenethyl)-1H-imidazole (0.5 g, 1.86 mmol) in dioxane (10 mL) was added 4-carbomethoxyphenylboronic acid (335 mg, 1.86 mmol), Cy₃P (200 mg), K₃PO₄ (1.18 g, 5.58 mmol) and PdP(t-Bu)₃ (100 mg) and the mixture was refluxed for 2 h under a N₂ atmosphere. After cooling to ambient temperature, the mixture was filtered and the filtrate was evaporated to give a yellow oil. The crude product was purified by column chromatography (petroleum ether/ethyl acetate=2:1) to afford compound Int 8-1 as yellow oil.

$^1$H NMR (CDCl₃) δ: 8.00 (d, J=8.0 Hz, 2H), 7.94 (s, 1H), 7.47 (d, J=8.4 Hz, 2H), 7.08 (s, 1H), 6.85-6.81 (m, 4H), 4.21 (t, J=6.8 Hz, 2H), 3.95 (s, 3H), 2.83 (t, J=6.4 Hz, 2H). MS-ESI (m/z): 325 (M+H)⁺.

Step B—Preparation of Int 8-2

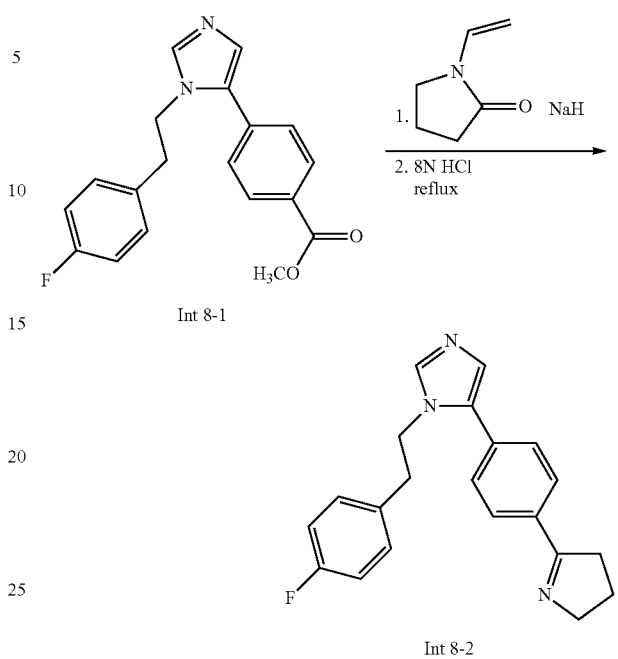

To a solution of 1-vinyl-pyrrolidin-2-one (283 mg, 2.54 mmol) in anhydrous THF (5 mL) was added the LDA solution (2.5 mL, 4.6 mmol) dropwise at −78° C. under N₂ atmosphere. The mixture was stirred at −78° C. for 1 h. Compound Int 8-1 (750 mg, 2.3 mmol) in THF (10 mL) was added dropwise and the reaction mixture was allowed to warm to room temperature for 4 h. The mixture was quenched by NH₄Cl solution (aq.) and extracted with EtOAc (3×20 mL). The organic extracts were washed with brine, dried over Na₂SO₄ and evaporated to dryness. The crude product was dissolved in 8 N HCl (15 mL) and the solution was refluxed for 8 h. After cooling to ambient temperature, the mixture was basified by adding NaOH solution (aq.) to pH~10. The aqueous layer was extracted with EtOAc, dried over Na₂SO₄ and evaporated. The crude product was purified by column chromatography (100% EtOAc) to afford compound Int 8-2 as yellow oil. $^1$H NMR (CDCl₃) δ: 7.90 (d, J=8.0 Hz, 2H), 7.52 (s, 1H), 7.33 (d, J=8.4 Hz, 2H), 7.11 (s, 1H), 6.91-6.82 (m, 4H), 4.22 (t, J=6.8 Hz, 2H), 4.10 (t, J=7.2 Hz, 2H), 2.97 (t, J=6.4 Hz, 2H), 2.82 (t, J=7.2 Hz, 2H), 2.12-2.00 (m, 2H). MS-ESI (m/z): 334 (M+H)⁺.

Step C—Preparation of Int 8-3

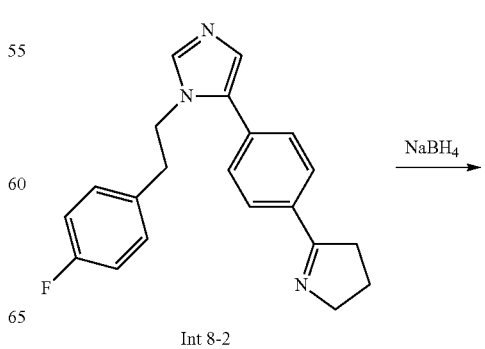

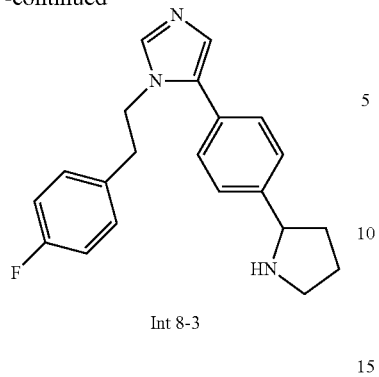

Int 8-3

To a solution of compound Int 8-2 (400 mg, 1.2 mmol) in EtOH (5 mL) was added NaBH₄ (136 mg, 3.6 mmol). The mixture was stirred at room temperature for 16 h then quenched with water and extracted with EtOAc (3×10 mL). The combined organic extracts were washed with brine, dried over Na₂SO₄ and evaporated to give crude desired product as yellow oil. The crude product of compound Int 8-3 (350 mg) was used directly without further purification. MS-ESI (m/z): 336 (M+H)⁺.

Step D—Preparation of Compound 8

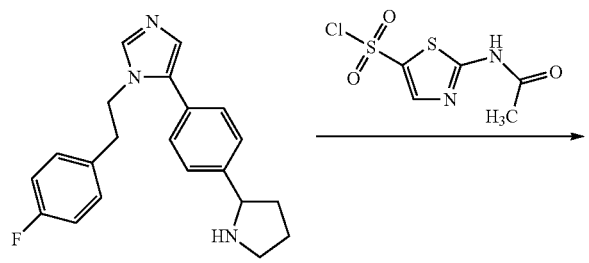

Int 8-3

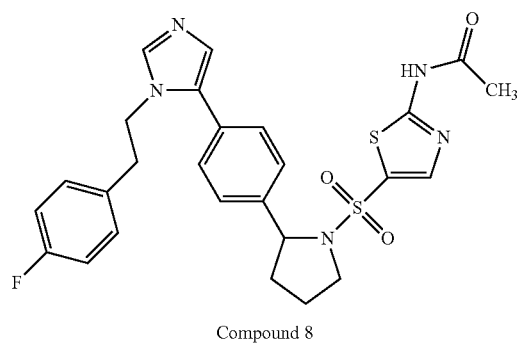

Compound 8

To a solution of compound Int 8-3 (150 mg, 0.45 mmol) in DMF (3 mL) was added Et₃N (0.5 mL) and 2-acetamidothiazole-5-sulfonyl chloride (108 mg, 0.45 mmol). The mixture was stirred for 0.5 h at ambient temperature, filtered and purified by preparative HPLC to afford Compound 8 as a white solid. ¹H NMR (CD₃OD) δ 8.87 (s, 1H), 7.93 (s, 1H), 7.58~7.55 (m, 3H), 7.39 (d, J=8.4 Hz, 2H), 6.95~6.91 (m, 4H), 4.84~4.80 (m, 1H), 4.51 (t, J=6.8 Hz, 2H), 3.74~3.34 (m, 1H), 3.52~3.46 (m, 1H), 2.91~2.85 (m, 2H), 2.25~2.19 (m, 4H), 1.98~1.84 (m, 3H). MS-ESI (m/z): 540 (M+H)⁺.

The following compound was prepared using a protocol similar to that described in Example 8 above.

| Cmpd | Structure | IUPAC name | M + 1 | ¹H NMR |
|---|---|---|---|---|
| 9 | 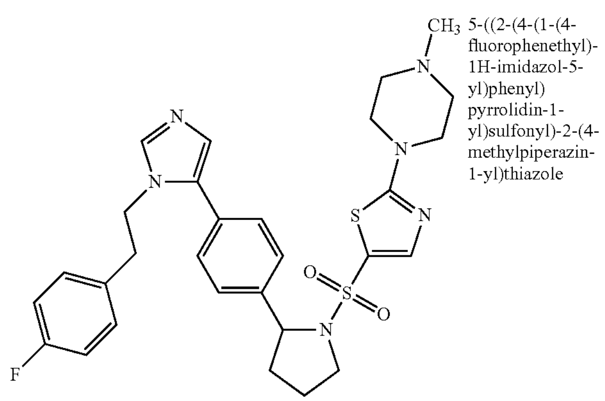 | 5-((2-(4-(1-(4-fluorophenethyl)-1H-imidazol-5-yl)phenyl)pyrrolidin-1-yl)sulfonyl)-2-(4-methylpiperazin-1-yl)thiazole | 581 | CD₃OD: δ 8.88 (d, J = 1.6 Hz, 1H), 7.71 (s, 1H), 7.58~7.55 (m, 3H), 7.69 (d, J = 8.4 Hz, 2H), 6.94~6.91 (m, 4H), 4.98~4.79 (m, 1H), 4.51 (t, J = 7.2 Hz, 2H), 4.49~3.29 (m, 10H), 2.97 (s, 3H), 2.89 (t, J = 6.8 Hz, 2H), 2.27~2.21 (m, 1H), 1.99~1.78 (m, 3H). |

Example 10

(R)—N-(5-(N-(1-(4-(1-(1-(4-fluorophenyl)ethyl)-1H-imidazol-5-yl)phenyl)cyclopropyl)sulfamoyl)thiazol-2-yl)acetamide (Compound 10)

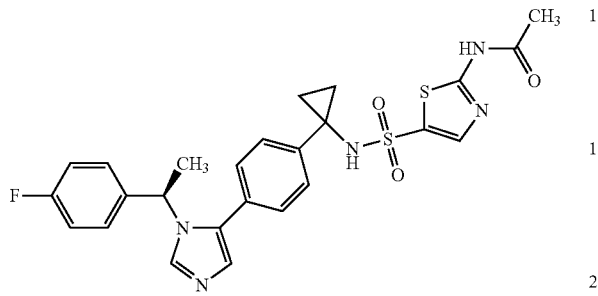

Step A—Preparation of Int 10-1

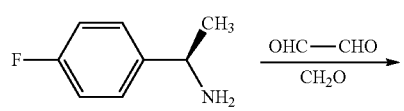

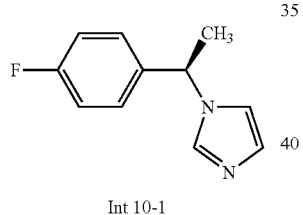

Int 10-1

To a solution of (R)-1-(4-fluorophenyl)ethanamine (2.54 mmol) in MeOH (30 mL) was added oxalaldehyde (5.08 mmol), formaldehyde (5.08 mmol) and ammonium acetate (5.08 mmol). The mixture was heated to reflux for 3 h, cooled and the solvent was evaporated. The crude product was purified by column chromatography (Petroleum Ether/EtOAc=3:2) to give compound Int 10-1 as brown oil. (200 mg, yield: 40%). MS-ESI (m/z):191 (M+H)$^+$.

Step B—Preparation of Int 10-2

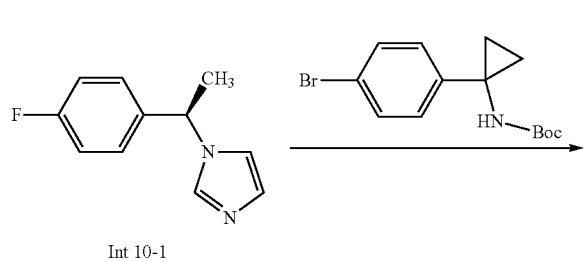

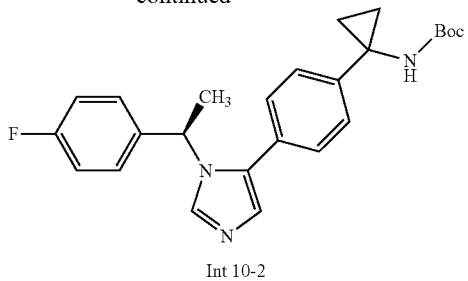

Int 10-2

To a solution of tert-butyl (1-(4-bromophenyl)cyclopropyl)carbamate (328 mg, 1.1 mmol) and compound Int 10-1 (200 mg, 1.1 mmol) in CH$_3$CN (5 mL) was added Pd$_2$(PPh$_3$)$_4$ (20 mg) and K$_3$PO$_4$ (40 mg) and the mixture was stirred at 90° C. for 3 hrs under a N$_2$ atmosphere. The reaction mixture was cooled, water was added and the mixture was extracted with EtOAc. The organic extracts were dried and the solvent was removed to give crude product Int 10-2 which was purified by HPLC. MS-ESI (m/z): 422 (M+H)$^+$.

Step C—Preparation of Int 10-3

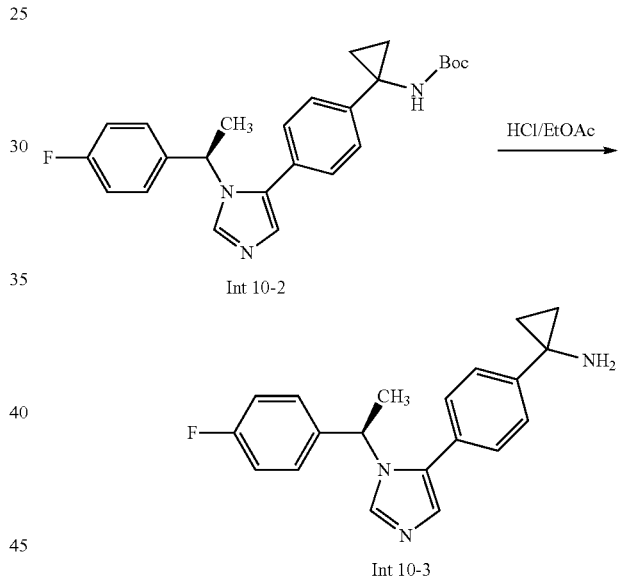

To a solution of compound Int 10-2 (100 mg, 0.24 mmol) in 4 mL of EtOAc was added HCl/EtOAc (10 mL) at room temperature. After stirring for 1 h, the mixture was concentrated to afford 40 mg of compound Int 10-3 as a white solid. MS-ESI (m/z): 322 (M+H)$^+$.

Step D—Preparation of Compound 10

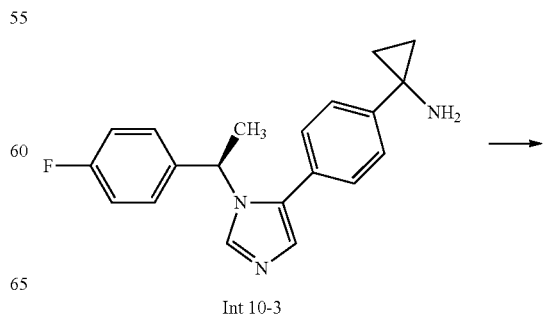

Int 10-3

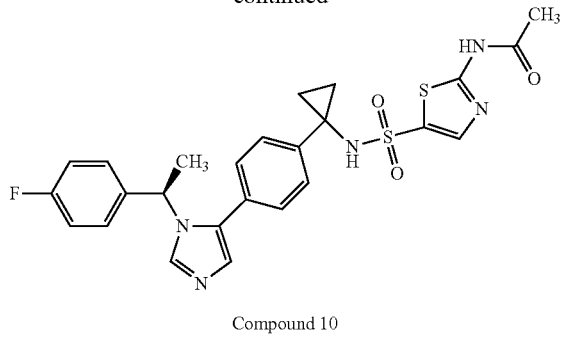

Compound 10

To a solution of compound Int 10-3 (40 mg, 0.12 mmol) in DMF (5 mL) was added Et$_3$N (0.5 mL) and 2-acetamidothiazole-5-sulfonyl chloride (48 mg, 0.2 mmol). The mixture was stirred for 10 min at ambient temperature. The mixture was filtered and evaporated to dryness. The crude product was purified by HPLC to afford Compound 10. $^1$H NMR (CD$_3$OD) δ 8.96 (s, 1H), 7.57 (s, 1H), 7.34 (d, J=8.0 Hz, 3H), 7.07 (d, J=8.0 Hz, 2H), 7.01 (d, J=6.8 Hz, 4H), 5.53 (q, J=7.2 Hz, 1H), 2.14 (s, 3H), 1.88 (d, J=7.2 Hz, 3H), 1.33-1.27 (m, 4H). MS-ESI (m/z): 526 (M+H)$^+$.

Example 11

N-(5-(N-((5-(1-(4-fluorophenethyl)-1H-imidazol-5-yl)pyridin-2-yl)methyl)sulfamoyl)thiazol-2-yl)acetamide (Compound 11)

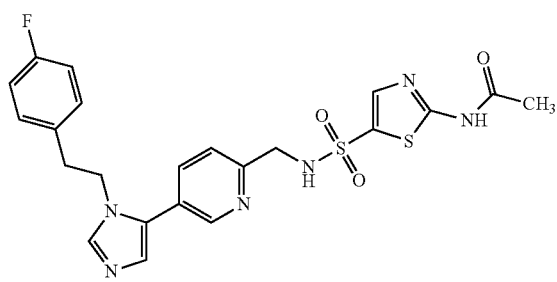 [SMILES: CC(=O)Nc1ncc(S(=O)(=O)NCc2ccc(-c3cncn3CCc3ccc(F)cc3)cn2)s1]

Step A—Preparation of Int 11-1

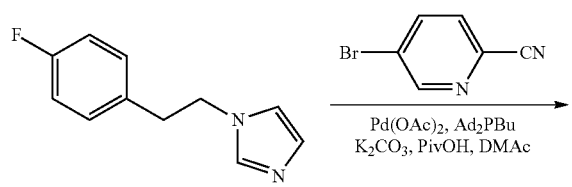

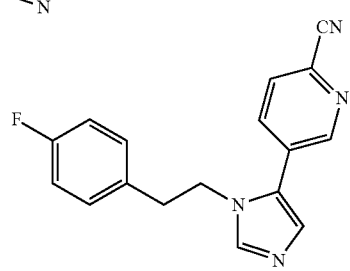

Int 11-1

To a solution of Int 3-1 (400 mg, 2.1 mmol) in DMAc/H$_2$O (10 mL/0.8 mL) was added 5-bromopicolinonitrile (497 mg, 2.73 mmol), potassium carbonate (1.02 g, 7.4 mmol), Ad$_2$PBu (226 mg, 0.63 mmol), PivOH (236 mg, 2.31 mmol) and Pd(OAc)$_2$ (47 mg, 0.21 mmol). The mixture was stirred overnight at 130° C. under nitrogen atmosphere. The mixture was cooled and water (5 mL) was added into the mixture before it was extracted with EtOAc (10 mL×3). The organic extracts were dried over sodium sulfate and concentrated. The crude mixture was purified by preparative TLC (Petroleum Ether:EtOAc=1:2) to give Int 11-1 (350 mg). MS (ESI): m/z (M+H)$^+$ 293.

Step B—Preparation of Int 11-2

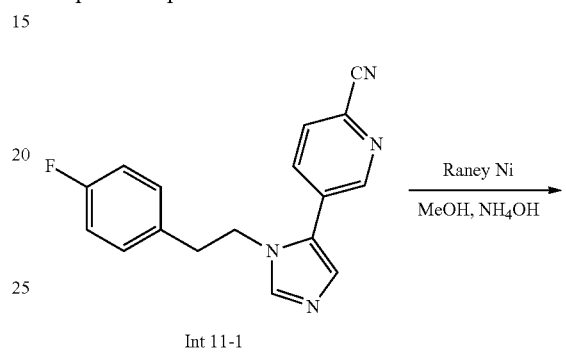

Int 11-1

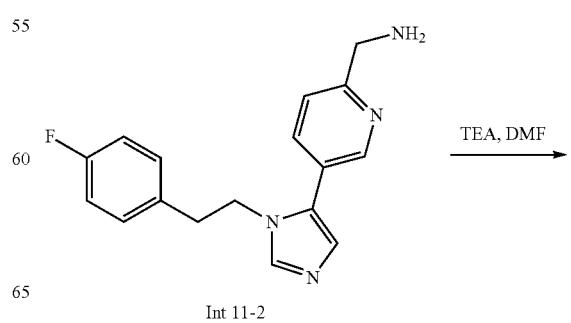

Int 11-2

To a solution of Int 11-1 (200 mg, 0.68 mmol) in MeOH (5 mL) was added conc ammonium hydroxide (0.6 mL) and Raney Ni (20 mg). The resulting mixture was stirred at room temperature under H$_2$ (45 psi) for 3 h, filtered and the filtrate was concentrated to give 160 mg of the crude product Int 11-2 which was used directly in the next step. MS (ESI): m/z (M+H)$^+$ 297.

Step C—Preparation of Compound 11

43
-continued

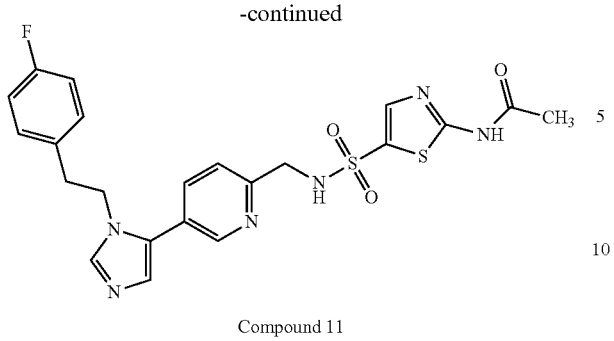

Compound 11

To a solution of Int 11-2 (100 mg, 0.34 mmol) in DMF (3 mL) was added TEA (0.4 mL), the mixture was stirred at 0° C. for 5 mins, then -acetamidothiazole-5-sulfonyl chloride (81 mg, 0.34 mmol) was added. The mixture was stirred at room temperature for 20 min then concentrated and purified by HPLC to give Compound 11. $^1$H NMR (CD$_3$OD): δ 8.19 (s, 1H), 7.71 (d, J=8.0 Hz, 1H), 7.56-7.63 (m, 3H), 6.95 (s, 1H), 6.85 (d, J=7.2 Hz, 4H), 4.25-4.29 (m, 4H), 2.80 (t, J=6.4 Hz, 2H), 2.05 (s, 3H). MS (ESI): m/z (M+H)$^+$ 501.

The following compounds 12-13 were prepared using a protocol similar to that described in Example 11 above.

44

Example 14
N-(2-(1-(4-fluorophenethyl)-1H-imidazol-5-yl)phenethyl)pyridine-3-sulfonamide (Compound 14)

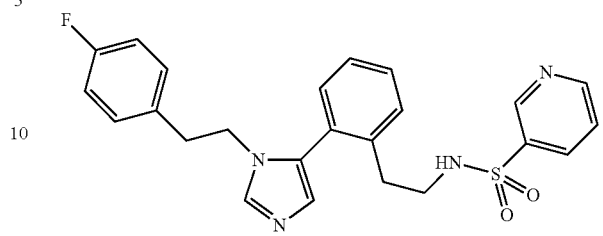

Step A—Preparation of Int 14-1

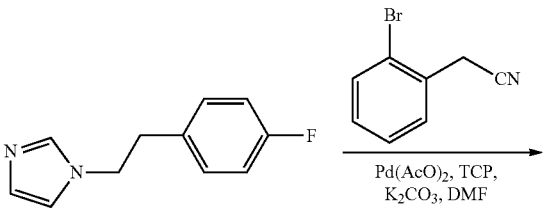

| Cmpd | Structure | IUPAC name | M + 1 | $^1$H NMR |
|---|---|---|---|---|
| 12 | ![structure] | N-(5-(N-(4-(1-(4-fluorophenethyl)-1H-imidazol-5-yl)benzyl)sulfamoyl)thiazol-2-yl)acetamide | 500 | CD$_3$OD: δ 8.80 (s, 1H), 7.81 (s, 1H), 7.54 (s, 1H), 7.49 (d, J = 8.4 Hz, 2H), 7.37 (d, J = 8.4 Hz, 2H), 6.97~6.91 (m, 4H), 4.48 (t, J = 6.8 Hz, 2H), 4.26 (s, 2H), 2.87 (t, J = 6.8 Hz, 2H), 2.19 (s, 3H). |
| 13 | ![structure] | N-(5-(N-(3-(1-(4-fluorophenethyl)-1H-imidazol-5-yl)benzyl)sulfamoyl)thiazol-2-yl)acetamide | 500 | CD$_3$OD: δ 8.87 (s, 1H), 7.83 (s, 1H), 7.56 (s, 1H), 7.52-7.43 (m, 2H), 7.38 (s, 1H), 7.37-7.28 (m, 1H), 6.98-6.90 (m, 4H), 4.51 (t, J = 6.8, 2H), 4.25 (s, 2H), 2.89 (t, J = 6.8, 2H), 2.21 (s, 3H). |

-continued

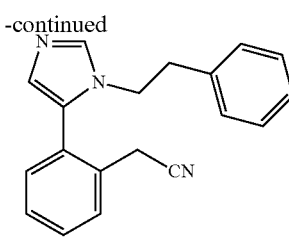
Int 14-1

-continued

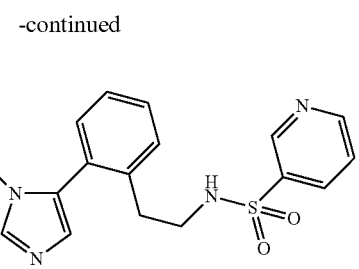
Compound 14

To a degassed solution of Int 3-1 (800 mg, 1.05 mmol), Cy₃P (224 mg, 0.8 mmol), (2-bromophenyl)acetonitrile (825 mg, 4.26 mmol) and K₂CO₃ (1.7 g, 12.6 mmol) in DMF (10 mL) was added Pd(OAc)₂ (90 mg, 0.4 mmol) under N₂ protection. The mixture was heated in a microwave at 150° C. for 30 min, cooled and filtered. The filtrate was diluted with EtOAc (40 mL), washed with water (25 mL) and brine (20 mL), dried over Na₂SO₄, filtered and concentrated. The residue was purified by column chromatography (Petroleum Ether:EtOAc=5:1) to give Int 14-1 (500 mg). MS (ESI): m/z (M+H)⁺ 306

Step B—Preparation of Int 14-2

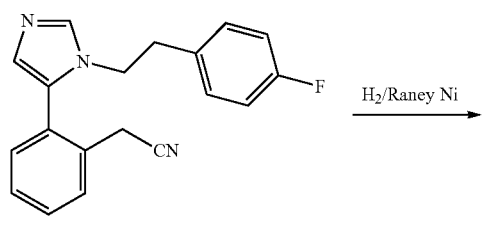

A solution of Int 14-1 (220 mg, 0.66 mmol) in MeOH (10 mL) was hydrogened with Raney Ni (50 mg) under 45 Psi of H₂ pressure for 6 h. The reaction mixture was filtered and the filtrate was concentrated to give 200 mg of Int 14-2 which was used in the next step without further purification. MS (ESI): m/z (M+H)⁺ 310.

Step C—Preparation of Compound 14

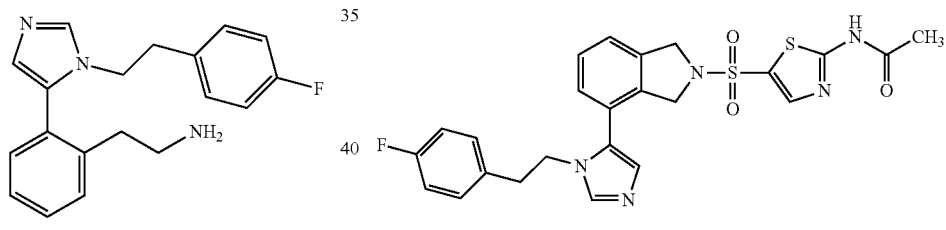

To a solution of Int 14-2 (80 mg, 0.31 mmol) and TEA (60 mg, 0.6 mmol) in DMF (5 mL) was added pyridine-3-sulfonyl chloride (55 mg, 0.31 mmol) at 0° C. The reaction mixture was stirred at room temperature for 2 h then purified by HPLC to give Compound 14 (50 mg). ¹H NMR (CD₃OD): 8.78 (s, 1H), 8.67 (q, J=1.6 Hz, 1H), 8.00-8.03 (m, 1H), 7.49 (q, J=5.2 Hz, 1H), 7.32 (t, J=7.6 Hz, 1H), 7.17-7.25 (m, 3H), 7.05 (s, 1H), 6.89 (d, J=7.2 Hz, 4H), 6.80 (d, J=7.6 Hz, 1H), 3.98 (t, J=6.8 Hz, 2H), 2.89-2.99 (m, 4H), 2.46 (t, J=7.2 Hz, 2H). MS (ESI): m/z (M+H)⁺ 451.

Example 15

N-(5-((4-(1-(4-fluorophenethyl)-1H-imidazol-5-yl)isoindolin-2-yl)sulfonyl)thiazol-2-yl)acetamide (Compound 15)

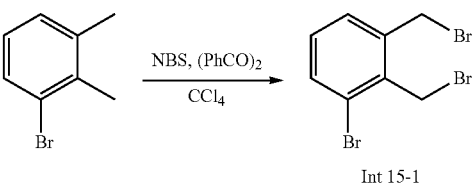

Step A—Preparation of Int 15-1

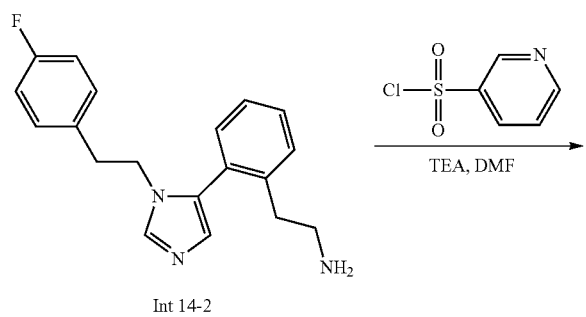

A mixture of compound 1-bromo-2,3-dimethylbenzene (10.0 g, 54.0 mmol), NBS (19.1 g, 108.0 mmol) and benzoyl peroxide (0.13 g, 0.54 mmol) in CCl₄ (100 mL) was refluxed overnight. The reaction was then cooled to 0° C. and filtered. The filtrate was concentrated and purified by column chromatography (Petroleum Ether:EtOAc=10:1) to give compound Int 15-1 (11.6 g).

¹H NMR (CDCl₃): δ 7.56 (d, J=8.0 Hz, 1H), 7.31 (d, J=6.8 Hz, 1H), 7.15 (t, J=8.0 Hz, 1H), 4.83 (s, 2H), 4.63 (s, 2H). MS (ESI): m/z (M+H)⁺ 343.

Step B—Preparation of Int 15-2

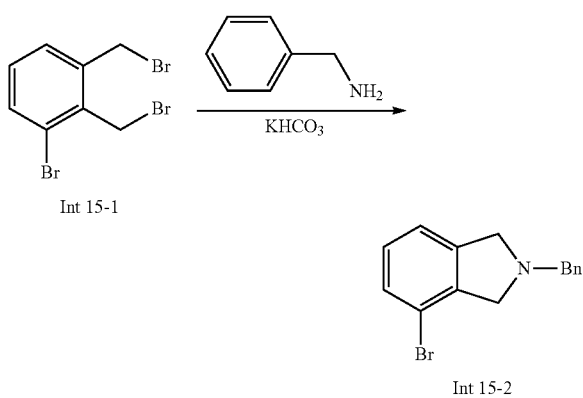

To a suspension of compound Int 15-1 (3.0 g, 8.8 mmol) in CH₃CN (22 mL) was added KHCO₃ (2.2 g, 21.9 mmol) and benzyl amine (0.94 g, 8.8 mmol). The resultant mixture was stirred at 75° C. overnight. The mixture was cooled and diluted with EtOAc (100 mL) and washed with 1M K₂CO₃ solution (40 mL), the organic layer was concentrated and purified by column chromatography (Petroleum Ether:EtOAc=20:1) to give compound Int 15-2 (1.1 g). $^1$H NMR (CDCl₃): δ 7.25-7.41 (m, 6H), 7.03-7.10 (m, 2H), 4.01 (s, 2H), 3.97 (s, 2H), 3.91 (s, 2H). MS (ESI): m/z (M+H)$^+$ 289.

Step C—Preparation of Int 15-3

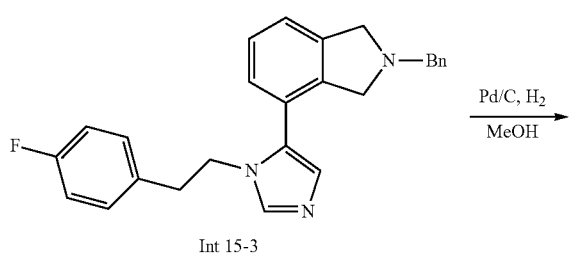

A mixture of Int 3-1 (462 mg, 2.4 mmol), Int 15-2 (700 mg, 2.4 mmol), Pd(OAc)₂ (54 mg, 0.24 mmol), P(n-Bu)Ad₂ (172 mg, 0.48 mmol) and K₂CO₃ (671 mg, 4.86 mmol) in DMF (15 mL) was heated to 120° C. overnight under nitrogen. The mixture was cooled and filtered and the filtrate was diluted with water (10 mL) and extracted with DCM (3×30 mL). The organic extracts were dried and evaporated to give compound Int 15-3 (300 mg). $^1$H NMR (CD₃OD): δ 8.93 (s, 1H), 7.65 (s, 1H), 7.47-7.61 (m, 7H), 7.37-7.38 (m, 1H), 6.95-6.99 (m, 5H), 4.78 (s, 2H), 4.62-4.65 (m, 4H), 4.34-4.39 (m, 2H), 2.91-2.95 (m, 2H). MS (ESI): m/z (M+H)$^+$ 398.

Step D—Preparation of Int 15-4

To a solution Int 15-3 (300 mg, 0.76 mmol) in 10 mL of EtOH was added Pd/C (100 mg). The reaction mixture was stirred under H₂ (50 psi) atmosphere overnight at room temperature then filtered and concentrated. The resulting residue was used for the next step directly (200 mg). MS (ESI): m/z (M+H)$^+$ 308.

Step E—Preparation of Compound 15

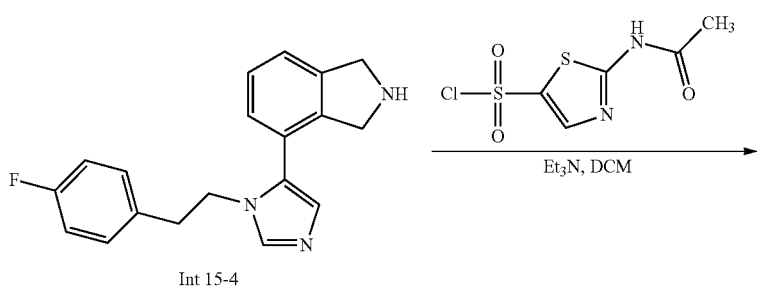

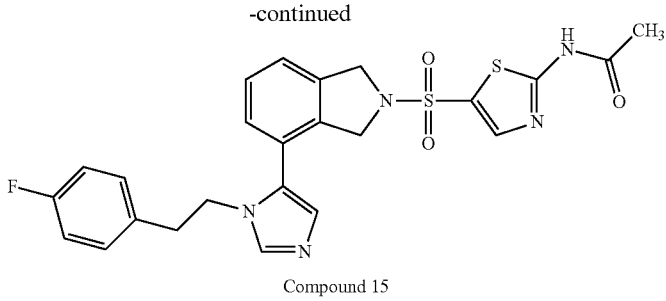

Compound 15

To the suspension of Int 15-4 (60 mg, 0.20 mmol) in DCM (5 mL) was added Et₃N (60 mg, 0.6 mmol) and 2-acetamidothiazole-5-sulfonyl chloride (47 mg, 0.20 mmol) at 0° C. The mixture was concentrated and purified by reverse phase HPLC to give Compound 15. ¹H NMR (CD₃OD): δ 8.04 (s, 1H), 7.67 (s, 1H), 7.30-7.35 (m, 2H), 7.18 (d, J=6.8 Hz, 1H), 6.95 (t, J=8.8 Hz, 3H), 6.81-6.84 (m, 2H), 4.67 (s, 2H), 4.42 (s, 2H), 4.10 (t, J=7.2 Hz, 2H), 2.60-2.63 (m, 2H), 2.03 (s, 3H). MS (ESI): m/z (M+H)⁺ 512.

The following compound 16 was prepared using a protocol similar to that described in Examples 15 above.

| Cmpd | Structure | IUPAC name | M + 1 | ¹H NMR |
|---|---|---|---|---|
| 16 | 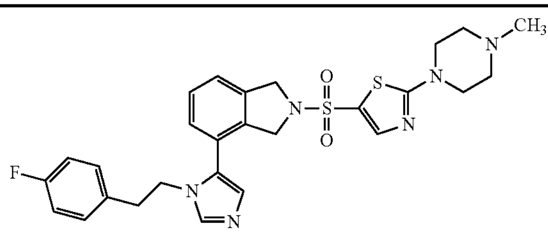 | 5-((4-(1-(4-fluorophenethyl)-1H-imidazol-5-yl)isoindolin-2-yl)sulfonyl)-2-(4-methylpiperazin-1-yl)thiazole | 553 | CD₃OD: δ 7.63 (d, J = 7.2 Hz, 1H), 7.32-7.40 (m, 2H), 7.14 (d, J = 7.2 Hz, 1H), 6.94 (s, 1H), 6.77-6.89 (m, 4H), 4.70 (s, 2H), 4.43 (s, 2H), 4.19 (t, J = 6.8 Hz, 2H), 3.40-3.43 (m, 4H), 2.67-2.71 (m, 2H), 2.40-2.42 (m, 4H), 2.27 (s, 3H). |

Example 17

N-(2-(1-(4-fluorophenethyl)-1H-imidazol-5-yl)benzyl)pyridine-3-sulfonamide (Compound 17)

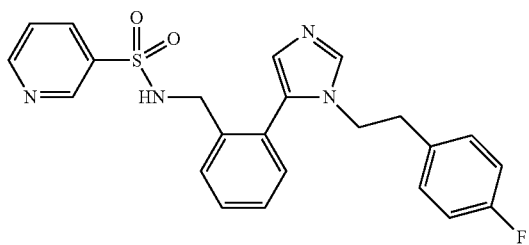 [SMILES: O=S(=O)(NCc1ccccc1-c1cncn1CCc1ccc(F)cc1)c1cccnc1]

Step A—Preparation of Int 17-1

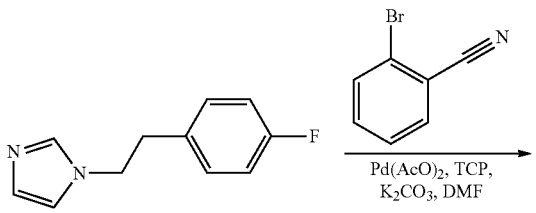

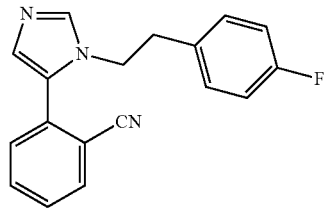

Int 17-1

To a degassed solution of Int 3-1 (200 mg, 1.05 mmol), Cy₃P (600 mg, 0.24 mmol), 2-bromobenzonitrile (191 mg, 0.56 mmol) and K₂CO₃ (434 mg, 3.15 mmol) in DMF (5 mL) was added Pd(OAc)₂ (23 mg, 0.105 mmol) under N₂ protection. The mixture was heated in a microwave reactor at 150° C. for 30 minutes then cooled and filtered. The filtrate was diluted with EtOAc (20 mL), washed with water (15 mL) and brine (20 mL), dried over Na₂SO₄, filtered and concentrated. The residue was purified by HPLC to give Int 17-1. ¹H NMR (DMSO-d⁶) δ 7.95 (d, J=7.9 Hz, 1H), 7.75-7.80 (m, 2H), 7.63 (t, J=6.8 Hz, 1H), 7.50 (d, J=7.3 Hz, 1H), 7.08 (s, 1H), 6.9-7.05 (m, 4H), 4.20 (t, J=7.0 Hz, 2H), 2.75 (t, J=7.0 Hz, 2H). MS (ESI): m/z (M+H)⁺ 292.

Step B—Preparation of Int 17-2

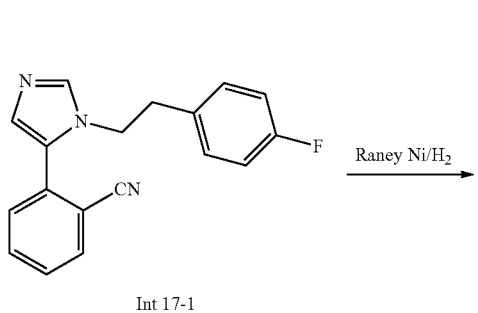

Int 17-1

Raney Ni/H₂ →

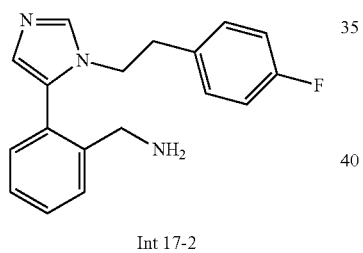

Int 17-2

A solution of Int 17-1 (220 mg, 0.76 mmol) in MeOH (10 mL) was hydrogened with Raney Ni (50 mg) under 45 Psi of H₂ pressure for 6 h. The mixture was filtered through celite and the filtrate was concentrated to give Int 17-2 (180 mg). MS (ESI): m/z (M+H)⁺ 296.

Step C—Preparation of Compound 17

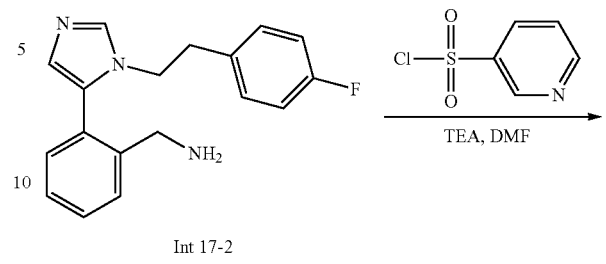

TEA, DMF →

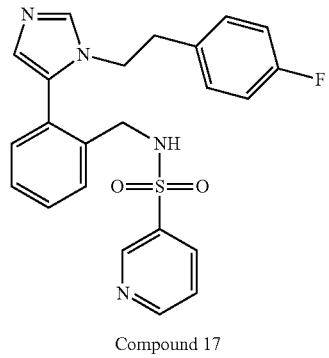

Compound 17

To a solution of Int 17-2 (170 mg, 0.58 mmol) and TEA (100 mg, 1.0 mmol) in DMF (5 mL) was added pyridine-3-sulfonyl chloride (90 mg, 0.5 mmol) at 0° C. The reaction mixture was stirred at room temperature for 2 h and evaporated. The resulting residue was purified by HPLC to give Compound 17 (100 mg). ¹H NMR (CD₃OD): δ 8.88 (s, 1H), 8.70 (q, J=4.4 Hz, 1H), 8.08 (q, J=4.4 Hz, 1H), 7.52-7.58 (m, 2H), 7.30-7.45 (m, 3H), 7.04 (q, J=0.8 Hz, 1H), 6.89 (q, J=5.2 Hz, 4H), 6.81 (s, 1H), 3.98 (t, J=6.8 Hz, 2H), 3.85 (s, 2H), 2.77 (t, J=6.8 Hz, 2H). MS (ESI): m/z (M+H)⁺ 437.

The following compound was prepared using a protocol similar to that described in Example 17 above.

| Cmpd | Structure | IUPAC name | M + 1 | ¹H NMR |
|---|---|---|---|---|
| 18 | (structure shown) | N-(5-(N-(2-(1-(4-fluorophenethyl)-1H-imidazol-5-yl)benzyl)sulfamoyl)thiazol-2-yl)acetamide | 500.1 | CD₃OD: δ 8.87 (s, 1H), 7.83 (s, 1H), 7.56 (s, 1H), 7.52-7.43 (m, 2H), 7.38 (s, 1H), 7.37-7.28 (m, 1H), 6.98-6.90 (m, 4H), 4.51 (t, J = 6.8, 2H), 4.25 (s, 2H), 2.89 (t, J = 6.8, 2H), 2.21 (s, 3H). |

Example 19

N-(2-(1-(4-fluorophenethyl)-1H-imidazol-5-yl)benzyl)-2-((7R,8aS)-7-hydroxyhexahydropyrrolo[1,2-a]pyrazin-2(1H)-yl)thiazole-5-sulfonamide (Compound 19)

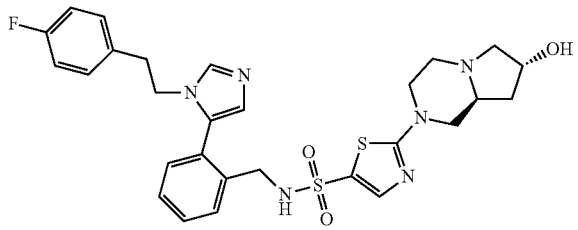 [SMILES: O=S(=O)(NCc1ccccc1-c1cncn1CCc1ccc(F)cc1)c1cnc(N2CCN3C[C@H](O)C[C@H]3C2)s1]

Step A—Preparation of Int 19-1

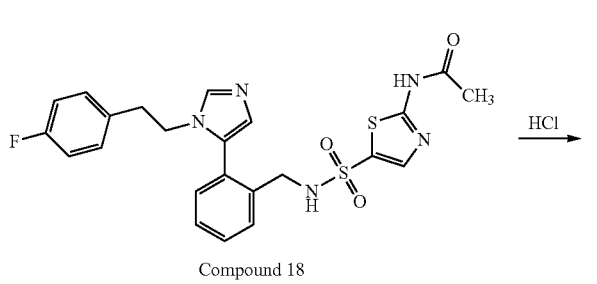

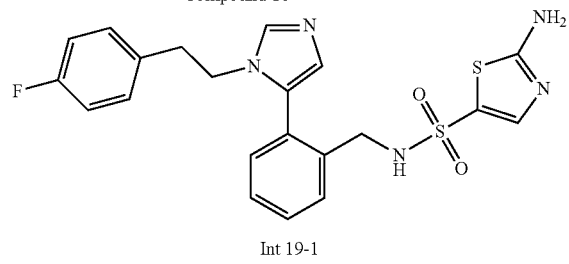

A mixture of compound 18 (400 mg, 0.779 mmol) in MeOH/6N aq. HCl (5 mL/5 mL) was stirred at 80° C. for 2 h. After the mixture was cooled to ambient temperature, the reaction mixture was concentrated and the residue was diluted with ethyl acetate (20 mL). The resulting solution was treated with 1M NaOH solution to pH~8 and the aqueous layer was extracted with ethyl acetate (3×30 mL). The organic layer was washed with brine, dried over anhydrous sodium sulfate, filtered and concentrated to give the compound Int 19-1 (300 mg). MS-ESI (m/z): 458 (M+H)$^+$.

Step B—Preparation of Int 19-2

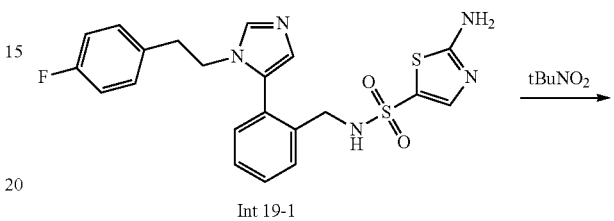

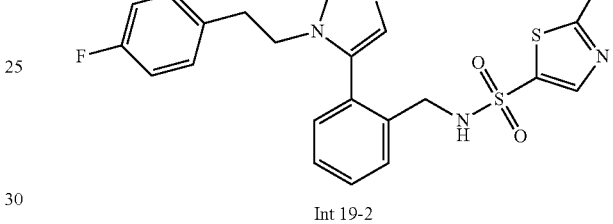

To a mixture of compound Int 19-1 (300 mg, 0.636 mmol) in acetonitrile (5 mL) was added CuBr$_2$ (284.2 mg, 1.272 mmol) and t-BuNO$_2$ (131.2 mg, 1.272 mmol). The mixture was stirred at 60° C. for 2 h. After cooling to ambient temperature, the reaction mixture was diluted with ethyl acetate (20 mL), and treated with conc. NH$_4$OH solution. The aqueous solution was extracted with ethyl acetate (3×30 mL) and the combined organic layers were dried over anhydrous Na$_2$SO$_4$, filtered and concentrated to give the crude product (280 mg). MS-ESI (m/z): 521, 523 (M+H)$^+$.

Step C—Preparation of Compound 19

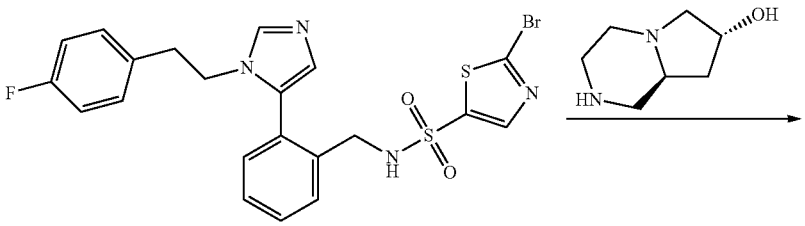

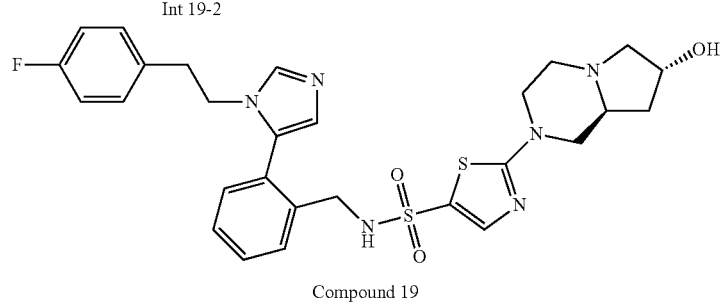

A mixture of compound Int 19-2 (280 mg, 0.56 mmol), (7R,8aS)-octahydropyrrolo[1,2-a]pyrazin-7-ol (95.6 mg, 0.67 mmol) and K₂CO₃ (155 mg, 1.12 mmol) in acetonitrile (5 mL) was stirred at 80° C. overnight. The reaction mixture was cooled and then treated with water and extrated with ethyl acetate (3×30 mL). The combined organics were washed with brine, dried over anhydrous sodium sulfate, filtered and concentrated. The residue was purified by preparative HPLC to afford Compound 19. ¹H NMR (CD₃OD) δ: 7.72 (s, 1H), 7.53 (d, J=7.6 Hz, 1H), 7.43-7.40 (m, 1H), 7.30-7.25 (m, 2H), 7.00-6.92 (m, 6H), 4.41-4.36 (m, 2H), 4.01-3.95 (m, 3H), 3.81-3.77 (m, 1H), 3.49-3.45 (m, 1H), 3.17-3.11 (m, 1H), 3.06-3.03 (m, 1H), 2.90 (q, J=6.8 Hz, 2H), 2.78 (t, J=11.2 Hz, 1H), 2.45-2.33 (m, 2H), 2.18-2.14 (m, 1H), 1.79-1.75 (m, 2H). MS-ESI (m/z): 583.2 (M+H)⁺.

Example 20

N-(5-((2-(2-(1-(2-methoxyethyl)-1H-imidazol-5-yl) phenyl)pyrrolidin-1-yl)sulfonyl)thiazol-2-yl)acetamide (Compound 20)

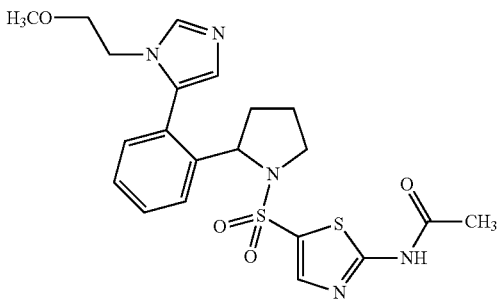 [SMILES: COCCn1cncc1-c1ccccc1C1CCCN1S(=O)(=O)c1cnc(NC(C)=O)s1]

Step A—Preparation of Int 20-1

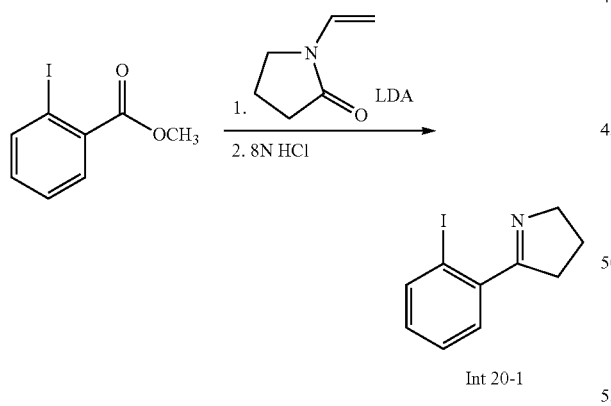

To a solution of 1-vinyl-pyrrolidin-2-one (14 g, 0.13 mol) in anhydrous tetrahydrofuran (250 mL) was added the LDA solution (126 mL, 0.25 mol) dropwise at −78° C. under a nitrogen atmosphere. The mixture was stirred at −78° C. for 1 hr then compound methyl 2-iodobenzoate (30 g, 0.11 mol) in tetrahydrofuran (150 mL) was added dropwise. The reaction mixture was allowed to warm to room temperature and stirred for another 2 hrs. The reaction was quenched with NH₄Cl aqueous solution (150 mL) and the aqueous solution was extracted with ethyl acetate (3×100 mL). The combined organic layers were washed with brine, dried over anhydrous sodium sulfate then filtered. The filtrate was concentrated under reduced pressure to give the crude product which was dissolved in methanol (100 mL) and 8N HCl (300 mL). The solution was refluxed for 8 hrs. After cooling to ambient temperature, the mixture was basified by adding NaOH aqueous solution to pH~10. The aqueous layer was extracted with ethyl acetate (3×100 mL) and the combined organic layer was dried over anhydrous sodium sulfate then filtered. The filtrate was concentrated under reduced pressure to give the crude product which was purified by silica gel chromatography eluting with petroleum ether: ethyl acetate (10:1, 5:1) to afford the product Int 20-1 (13 g, yield: 42%) as yellow oil. ¹H NMR (CDCl₃) δ: δ 7.87-7.83 (m, 1H), 7.42-7.26 (m, 2H), 7.05 (t, J=7.6 Hz, 1H), 4.12-4.05 (m, 2H), 2.96-2.91 (m, 2H), 2.10-2.02 (m, 2H). MS-ESI (m/z): 272.1 (M+H)⁺.

Step B—Preparation of Int 20-2

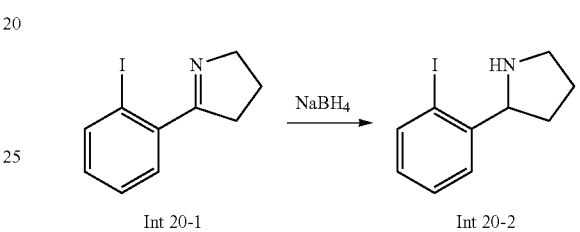

To a solution of compound Int 20-1 (13 g, 47 mmol) in ethanol (150 mL) was added NaBH₄ (5.36 g, 141 mmol). The mixture was stirred at room temperature for 16 hrs. The reaction was quenched with water (100 mL) and the aqueous solution was extracted with ethyl acetate (3×100 mL). The combined organic layer was washed with brine, dried over anhydrous sodium sulfate then filtered. The filtrate was concentrated under reduced pressure to give the crude product Int 20-2 as yellow solid, which was used directly without further purification. MS-ESI (m/z): 274.1 (M+H)⁻.

Step C—Preparation of Int 20-3

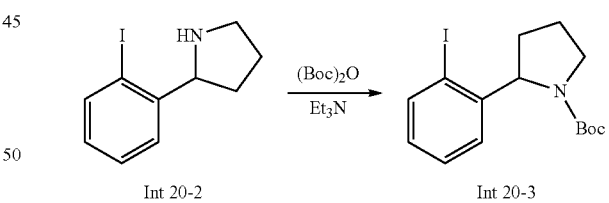

To a solution of compound Int 20-2 (15 g, 44 mmol) and triethylamine (18.5 mL, 132 mmol) in dichloromethane (200 mL) was added a solution of Boc₂O (19 g, 88 mmol) in dichloromethane (50 mL). After addition, the reaction mixture was stirred at room temperature for 3 hrs. The reaction solution was concentrated to give the crude product which was purified by silica gel chromatography eluting with petroleum ether: ethyl acetate (30:1, 20:1) to afford the product Int 20-3 as yellow oil. ¹H NMR (CDCl₃) δ: δ 7.79 (d, J=7.6 Hz, 1H), 7.30-7.26 (m, 1H), 7.11-7.03 (m, 1H), 6.91 (t, J=7.2 Hz, 1H), 5.07-4.93 (m, 1H), 3.73-3.51 (m, 2H), 2.42-2.34 (m, 1H), 1.90-1.69 (m, 4H), 1.45-1.33 (m, 9H). MS-ESI (m/z): 317.9 (M-55)⁺.

Step D—Preparation of Int 20-4

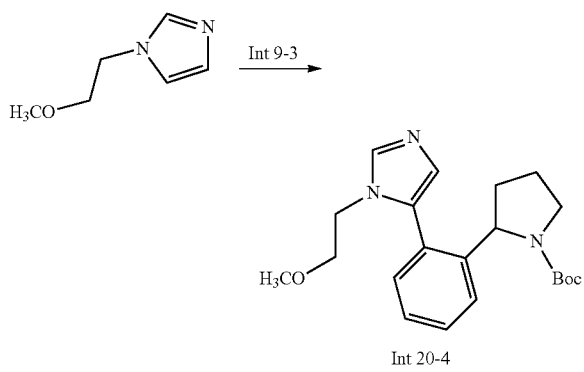

To a stirred solution of 0.68 g (5.36 mmol) of 1-(2-methoxyethyl)-1H-imidazole (CAS No. 126301-59-5) in N,N-dimethylacetamide (20 mL) was added compound Int 20-3 (2.0 g, 5.36 mmol), P(n-Bu)Ad$_2$ (200 mg), potassium carbonate (1.48 g, 10.7 mmol) and Pd(OAc)$_2$ (100 mg). The mixture was stirred at 120° C. for 6 hrs under nitrogen atmosphere. After cooling to ambient temperature, the mixture was filtered and the filtrate was evaporated to give the desired product which was purified by preparative HPLC to afford the product Int 20-4 (280 mg) as colorless oil.

$^1$H NMR (MeOD) δ: 7.83-7.79 (m, 1H), 7.44-7.24 (m, 4H), 6.92 (s, 1H), 4.78-4.64 (m, 1H), 4.09-3.97 (m, 2H), 3.61-3.43 (m, 4H), 3.26 (s, 3H), 2.08-2.00 (m, 1H), 1.87-1.61 (m, 3H), 1.43-1.22 (m, 9H). MS-ESI (m/z): 372.1 (M+H)$^+$.

Step E—Preparation of Int 20-5

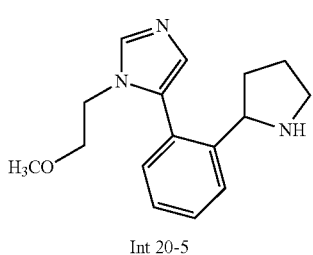

A mixture of compound Int 20-4 (50 mg, 0.14 mmol) in HCl/dioxane (10 mL) was stirred at 60° C. for 30 mins. The reaction solution was concentrated to afford 36 mg of the product Int 20-5 (as the HCl salt) as white solid which was used directly in next step without further purification. MS-ESI (m/z): 272.1 (M+H)$^+$.

Step F—Preparation of Compound 20

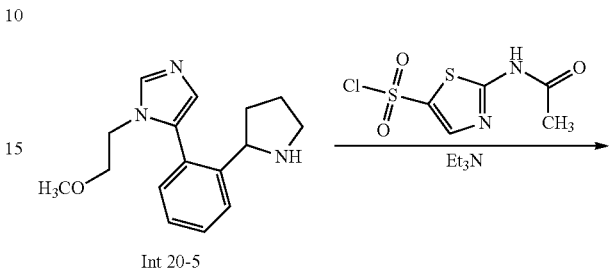

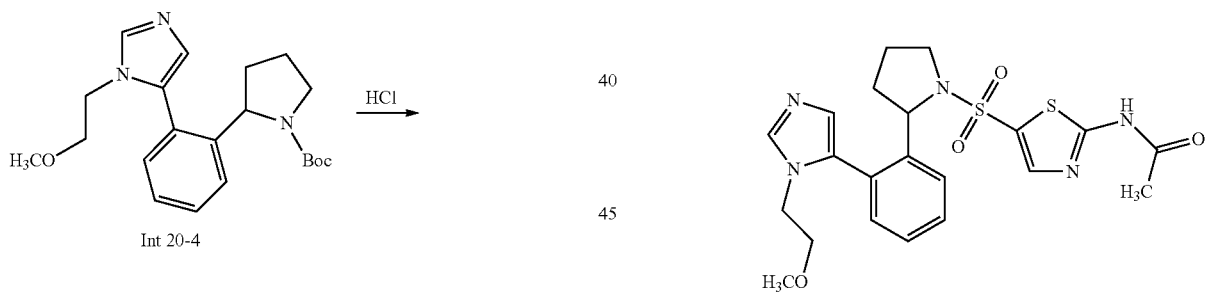

To a solution of compound Int 20-5 (36 mg, 0.14 mmol) and triethylamine (0.1 mL, 0.42 mmol) in dichloromethane (2 mL) was added compound 2-acetamidothiazole-5-sulfonyl chloride (33 mg, 0.14 mmol). After addition, the reaction mixture was stirred at room temperature for 1 hr. The reaction solution was concentrated to give the crude product which was purified by HPLC to afford Compound 20 (32 mg) as yellow solid. $^1$H NMR (CD$_3$OD) δ 7.91 (s, 1H), 7.71 (s, 1H), 7.64 (d, J=7.2 Hz, 1H), 7.49 (t, J=7.2 Hz, 1H), 7.36 (t, J=7.2 Hz, 1H), 7.27 (d, J=7.6 Hz, 1H), 6.89 (s, 1H), 4.61 (s, 1H), 4.47-4.45 (m, 1H), 4.03-3.92 (m, 2H), 3.72-3.33 (m, 4H), 3.30 (s, 3H), 2.23 (s, 3H), 1.99-1.91 (m, 2H), 1.74-1.70 (m, 1H), 1.54-1.51 (m, 1H). MS-ESI (m/z): 476.1 (M+H)$^+$.

The following compounds 21-57 were prepared using a protocol similar to that described in Example 20 above.

| Cmpd | Structure | IUPAC name | M + 1 | ¹H NMR |
|---|---|---|---|---|
| 21 | 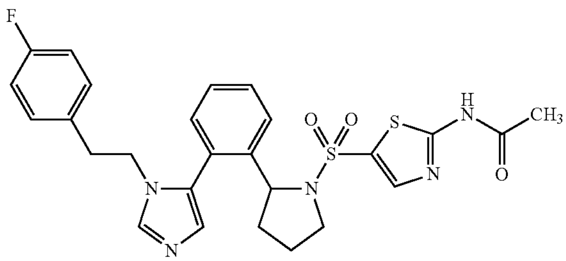 [SMILES: CC(=O)Nc1ncc(S(=O)(=O)N2CCCC2c2ccccc2-c2cncn2CCc2ccc(F)cc2)s1] | N-(5-((2-(2-(1-(4-fluorophenethyl)-1H-imidazol-5-yl)phenyl)pyrrolidin-1-yl)sulfonyl)thiazol-2-yl)acetamide | 540.1 | CD$_3$OD δ 7.74 (s, 2H), 7.65 (d, J = 7.6 Hz, 1H), 7.51 (t, J = 7.6 Hz, 1H), 7.33 (t, J = 6.4 Hz, 1H), 7.06-6.89 (m, 6H), 4.49-4.46 (m, 1H), 4.19-4.07 (m, 2H), 3.68-3.64 (m, 1H), 3.41-3.37 (m, 1H), 3.01-2.94 (m, 2H), 2.23 (s, 3H), 1.95-1.88 (m, 2H), 1.72-1.67 (m, 1H), 1.54-1.41 (m, 1H). |
| 22a | 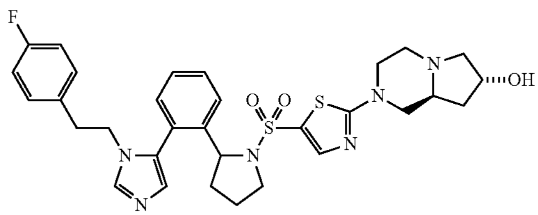 [SMILES: O=S(=O)(c1cnc(N2CCN3C[C@H](O)C[C@H]3C2)s1)N1CCCC1c1ccccc1-c1cncn1CCc1ccc(F)cc1] | (7R,8aS)-2-(5-(((R or S)-2-(2-(1-(4-fluoro-phenethyl)-1H-imidazol-5-yl)phenyl)pyrrolidin-1-yl)sulfonyl)thiazol-2-yl)octahydro-pyrrolo[1,2-a]pyrazin-7-ol | 623.2 | CDCl$_3$ δ 7.67 (d, J = 7.6 Hz, 1H), 7.52-7.48 (m, 3H), 7.32-7.28 (m, 1H), 7.00-6.94 (m, 6H), 4.58-4.55 (m, 2H), 4.06-3.88 (m, 4H), 3.68-3.56 (m, 2H), 3.50-3.29 (m, 2H), 3.10-3.07 (m, 1H), 2.95-2.89 (m, 3H), 2.58-2.47 (m, 3H), 2.29-2.25 (m, 1H), 2.03-1.85 (m, 4H), 1.74-1.65 (m, 2H). |
| 22b | 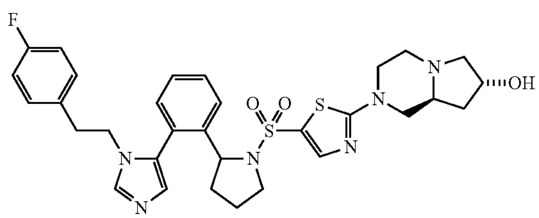 [SMILES: O=S(=O)(c1cnc(N2CCN3C[C@H](O)C[C@H]3C2)s1)N1CCCC1c1ccccc1-c1cncn1CCc1ccc(F)cc1] | (7R,8aS)-2-(5-(((R or S)-2-(2-(1-(4-fluoro-phenethyl)-1H-imidazol-5-yl)phenyl)pyrrolidin-1-yl)sulfonyl)thiazol-2-yl)octahydro-pyrrolo[1,2-a]pyrazin-7-ol | 623.2 | CDCl$_3$ δ 7.64 (d, J = 7.2 Hz, 1H), 7.49-7.45 (m, 3H), 7.29-7.26 (m, 1H), 6.99-6.91 (m, 6H), 4.57-4.54 (m, 2H), 4.05-3.82 (m, 4H), 3.63-3.53 (m, 2H), 3.33-3.22 (m, 2H), 3.07-3.04 (m, 1H), 2.91-2.82 (m, 3H), 2.51-2.44 (m, 2H), 2.24-2.20 (m, 1H), 2.04-1.83 (m, 3H), 1.82-1.63 (m, 4H). |
| 23a | 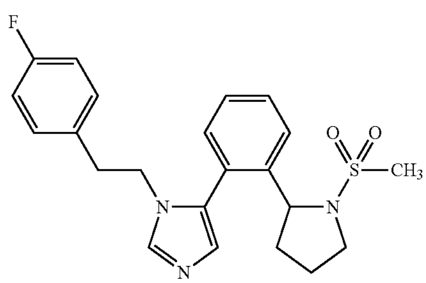 [SMILES: CS(=O)(=O)N1CCCC1c1ccccc1-c1cncn1CCc1ccc(F)cc1] | (R or S)-1-(4-fluorophenethyl)-5-(2-(1-(methylsulfonyl)pyrrolidin-2-yl)phenyl)-1H-imidazole | 414.2 | CD$_3$OD: δ 7.62 (d, J = 8.0 Hz, 2H), 7.47 (t, J = 7.6 Hz, 1H), 7.29 (t, J = 14.8 Hz, 1H), 7.01-6.89 (m, 6H), 4.61-4.58 (m, 1H), 3.79-3.48 (m, 2H), 2.78 (s, 1H), 2.25-2.15 (m, 1H), 2.08-1.96 (m, 1H), 1.88-1.81 (m, 1H), 1.76-1.22 (m, 1H), 2.25-2.15 (m, 1H), 3.42-3.30 (m, 4H), 3.15 (s, 3H), 3.04-2.90 (m, 2H), 2.02-1.88 (m, 2H), 1.72-1.62 (m, 1H), 1.60-1.48 (m, 1H). |
| 23b | 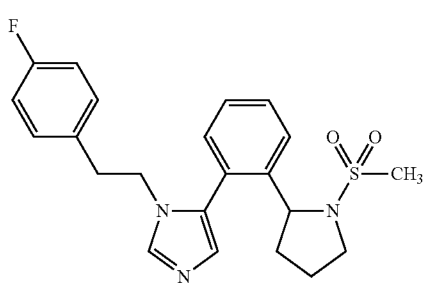 [SMILES: CS(=O)(=O)N1CCCC1c1ccccc1-c1cncn1CCc1ccc(F)cc1] | (R or S)-1-(4-fluorophenethyl)-5-(2-(1-(methylsulfonyl)pyrrolidin-2-yl)phenyl)-1H-imidazole | 414.2 | CD$_3$OD: δ 7.62 (d, J = 8.0 Hz, 2H), 7.47 (t, J = 7.6 Hz, 1H), 7.29 (t, J = 14.8 Hz, 1H), 7.01-6.89 (m, 6H), 4.61-4.58 (m, 1H), 3.79-3.48 (m, 2H), 2.78 (s, 1H), 2.25-2.15 (m, 1H), 2.08-1.96 (m, 1H), 1.88-1.81 (m, 1H), 1.76-1.22 (m, 1H), 2.25-2.15 (m, 1H), 3.42-3.30 (m, 4H), 3.15 (s, 3H), 3.04-2.90 (m, 2H), 2.02-1.88 (m, 2H), 1.72-1.62 (m, 1H), 1.60-1.48 (m, 1H). |

| Cmpd | Structure | IUPAC name | M + 1 | $^1$H NMR |
|---|---|---|---|---|
| 24 | 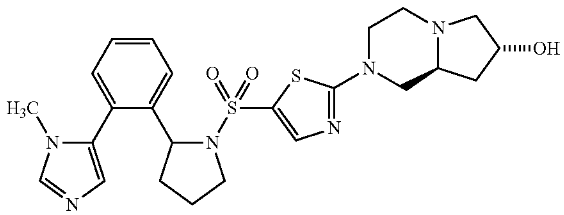 [SMILES: Cn1cncc1-c1ccccc1C1CCCN1S(=O)(=O)c1cnc(N2CCN3C[C@H](O)C[C@H]3C2)s1] | (7R,8aS)-2-(5-((2-(2-(1-methyl-1H-imidazol-5-yl)phenyl)pyrrolidin-1-yl)sulfonyl)thiazol-2-yl)octahydro-pyrrolo[1,2-a]pyrazin-7-ol | 515 | (DMSO-d6) δ 7.63-7.60 (m, 2H), 7.48-7.42 (m, 2H), 7.31 (t, J = 7.6 Hz, 1H), 7.17-7.15 (m, 1H), 6.94 (d, J = 2.8 Hz, 1H), 4.57-4.50 (m, 2H), 4.08-3.80 (m, 2H), 3.63-3.45 (m, 4H), 3.34-3.00 (m, 5H), 2.87-2.86 (m, 1H), 2.52-2.42 (m, 2H), 2.25-2.21 (m, 1H), 1.98-1.74 (m, 5H), 1.64-1.62 (m, 1H). |
| 25 | 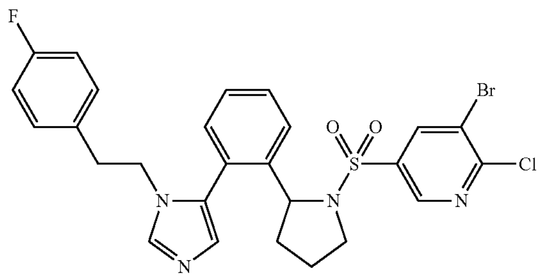 [SMILES: O=S(=O)(c1cnc(Cl)c(Br)c1)N1CCCC1c1ccccc1-c1cncn1CCc1ccc(F)cc1] | 3-bromo-2-chloro-5-((2-(2-(1-(4-fluoro-phenethyl)-1H-imidazol-5-yl)phenyl)pyrrolidin-1-yl)sulfonyl)pyridine | 591.2 | CD$_3$OD: δ 8.45 (s, 1H), 8.02 (s, 1H), 7.42 (s, 1H), 7.81 (m, 2H), 7.38-7.29 (m, 3H), 7.04-6.92 (m, 6H), 4.62-4.59 (m, 1H), 4.15-4.06 (m, 2H), 3.68-3.63 (m, 1H), 3.57-3.51 (m, 1H), 2.96-2.93 (m, 2H), 2.16-1.94 (m, 2H), 1.79-1.67 (m, 2H) |
| 26 | 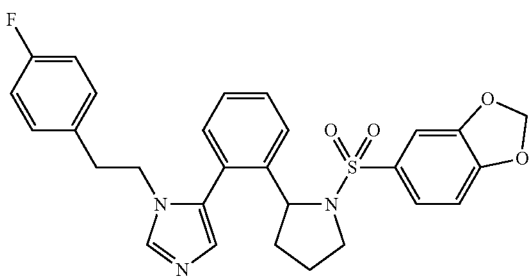 [SMILES: O=S(=O)(c1ccc2c(c1)OCO2)N1CCCC1c1ccccc1-c1cncn1CCc1ccc(F)cc1] | 5-(2-(1-(benzo[d][1,3]dioxol-5-ylsulfonyl)pyrrolidin-2-yl)phenyl)-1-(4-fluorophenethyl)-1H-imidazole | 520.2 | CD$_3$OD: δ 7.82 (s, 1H), 7.57 (d, J = 8.0 Hz, 1H), 7.47 (t, J = 7.2 Hz, 1H), 7.32-7.28 (m, 1H), 7.10 (d, J = 8.0 Hz, 1H), 7.2-6.88 (m, 8H), 6.06 (s, 2H), 4.50-4.47 (m, 1H), 4.11-4.08 (m, 1H), 3.57-3.53 (m, 1H), 3.40-3.34 (m, 1H), 2.97-2.92 (m, 2H), 1.95-1.84 (m, 2H), 1.69-1.61 (m, 1H), 1.47-1.43 (m, 1H) |
| 27 | 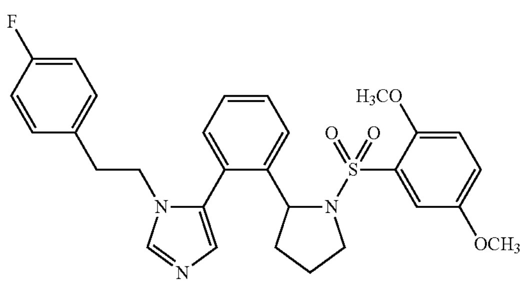 [SMILES: COc1ccc(OC)c(S(=O)(=O)N2CCCC2c2ccccc2-c2cncn2CCc2ccc(F)cc2)c1] | 5-(2-(1-((2,5-dimethoxyphenyl)sulfonyl)pyrrolidin-2-yl)phenyl)-1-(4-fluorophenethyl)-1H-imidazole | 536.2 | CD$_3$OD: δ 7.67 (s, 1H), 7.56 (d, J = 7.6 Hz, 1H), 7.42 (t, J = 7.6 Hz, 1H), 7.29-7.26 (m, 2H), 7.12-7.09 (m, 2H), 6.96-6.87 (m, 3H), 5.15-5.12 (m, 1H), 4.08 (t, J = 7.2 Hz, 2H), 3.71 (s, 3H), 3.70 (s, 3H), 3.66-3.55 (m, 1H), 3.19-3.13 (m, 1H), 2.88-2.84 (m, 2H), 2.04-1.89 (m, 2H), 1.69-1.64 (m, 2H) |
| 28a | 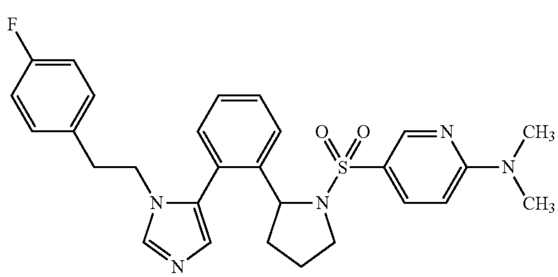 [SMILES: CN(C)c1ccc(S(=O)(=O)N2CCCC2c2ccccc2-c2cncn2CCc2ccc(F)cc2)cn1] | (R or S)-5-((2-(2-(1-(4-fluorophenethyl)-1H-imidazol-5-yl)phenyl)pyrrolidin-1-yl)sulfonyl)-N,N-dimethylpyridin-2-amine | 520.2 | CD$_3$OD: δ 8.23 (s, 1H), 7.72 (s, 1H), 7.58 (d, J = 7.6 Hz, 1H), 7.51-7.43 (m, 2H), 7.29 (t, J = 7.2 Hz, 1H), 7.01-6.90 (m, 6H), 6.60 (d, J = 9.2 Hz, 1H), 4.47-4.44 (m, 1H), 4.10-4.07 (m, 2H), 3.57-3.53 (m, 1H), 3.35-3.31 (m, 1H), 3.1 (s, 6H), 2.95-2.89 (m, 2H), 1.93-1.83 (m, 2H), 1.67-1.60 (m, 1H), 1.50-1.45 (m, 1H) |

| Cmpd | Structure | IUPAC name | M + 1 | 1H NMR |
| --- | --- | --- | --- | --- |
| 28b | 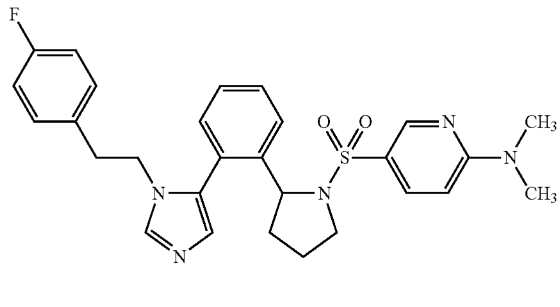 [SMILES: CN(C)c1ccc(S(=O)(=O)N2CCCC2c2ccccc2-c2cncn2CCc2ccc(F)cc2)cn1] | (R or S)-5-((2-(2-(1-(4-fluorophenethyl)-1H-imidazol-5-yl)phenyl)pyrrolidin-1-yl)sulfonyl)-N,N-dimethylpyridin-2-amine | 520.2 | CD3OD: δ 8.28 (s, 1H), 7.75 (s, 1H), 7.63 (d, J = 7.6, 1H), 7.58-7.48 (m, 2H),, 7.34 (t, J = 7.8, 1H), 7.09-6.92 (m, 6H), 6.65 (d, J = 9.2, 1H), 4.52-4.44 (m, 1H), 4.18-4.07 (m, 2H), 3.62-3.53 (m, 1H), 3.42-3.34 (m, 1H), 3.16 (s, 6H), 3.02-2.91 (m, 2H), 1.98-1.88 (m, 2H), 1.72-1.62 (m, 1H), 1.58-1.48 (m, 1H). |
| 29 | 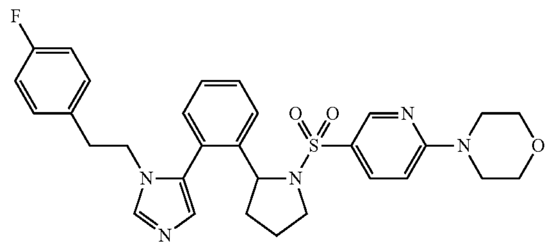 [SMILES: O=S(=O)(c1ccc(N2CCOCC2)nc1)N1CCCC1c1ccccc1-c1cncn1CCc1ccc(F)cc1] | 4-(5-((2-(2-(1-(4-fluorophenethyl)-1H-imidazol-5-yl)phenyl)pyrrolidin-1-yl)sulfonyl)pyridin-2-yl)morpholine | 562 | CD3OD: δ 8.25 (s, 1H), 7.71 (s, 1H), 7.57-7.51 (m, 2H), 7.46-7.42 (m, 1H),, 7.28 (t, J = 7.2 Hz, 1H), 7.01-6.90 (m, 6H), 6.75 (d, J = 9.2 Hz, 1H), 4.48-4.45 (m, 1H), 4.09-4.06 (m, 2H), 3.73-3.61 (m, 4H), 3.60-3.53 (m, 5H), 3.36-3.31 (m, 1H), 2.96-2.88 (m, 2H), 1.92-1.83 (m, 2H), 1.67-1.61 (m, 1H), 1.50-1.46 (m, 1H). |
| 30 | 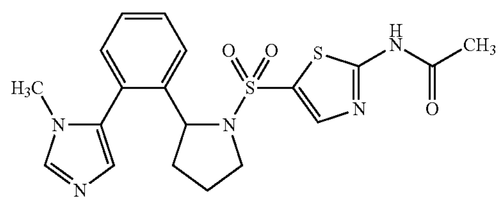 [SMILES: CC(=O)Nc1ncc(S(=O)(=O)N2CCCC2c2ccccc2-c2cncn2C)s1] | N-(5-((2-(2-(1-methyl-1H-imidazol-5-yl)phenyl)pyrrolidin-1-yl)sulfonyl)thiazol-2-yl)acetamide | 432.1 | (DMSO-d6) δ 7.78 (s, 1H), 7.62-7.59 (m, 2H), 7.48 (t, J = 7.2 Hz, 1H), 7.35 (t, J = 7.2 Hz, 1H), 7.25 (d, J = 7.2 Hz, 1H), 6.89 (s, 1H), 4.41 (t, J = 7.2 Hz, 1H), 3.66-3.60 (m, 1H), 3.37-3.30 (m, 5H), 2.20 (s, 3H), 2.01-1.82 (m, 2H), 1.71-1.63 (m, 1H), 1.44-1.37 (m, 1H). |
| 31 | 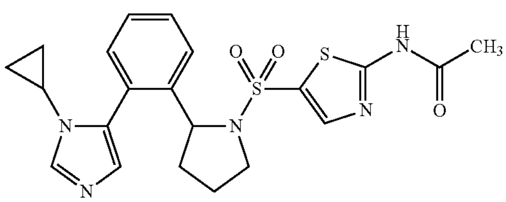 [SMILES: CC(=O)Nc1ncc(S(=O)(=O)N2CCCC2c2ccccc2-c2cncn2C2CC2)s1] | N-(5-((2-(2-(1-cyclopropyl-1H-imidazol-5-yl)phenyl)pyrrolidin-1-yl)sulfonyl)thiazol-2-yl)acetamide | 458.1 | (DMSO-d6) δ 7.78 (s, 1H), 7.59 (d, J = 7.6 Hz, 1H), 7.49-7.42 (m, 2H), 7.38-7.33 (m, 2H), 6.83 (s, 1H), 4.50 (t, J = 2.0 Hz, 1H), 3.62-3.58 (m, 2H), 3.30-3.25 (m, 2H), 2.08 (s, 3H), 1.94-1.83 (m, 2H), 1.65-1.61 (m, 1H), 1.49-1.44 (m, 1H), 1.05-1.01 (m, 1H), 0.89-0.85 (m, 1H), 0.80-0.68 (m, 2H). |
| 32 | 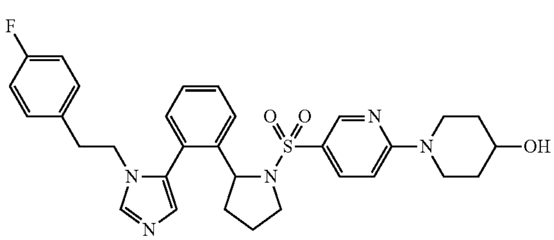 [SMILES: O=S(=O)(c1ccc(N2CCC(O)CC2)nc1)N1CCCC1c1ccccc1-c1cncn1CCc1ccc(F)cc1] | (R or S)-1-(5-((2-(2-(1-(4-fluorophenethyl)-1H-imidazol-5-yl)phenyl)pyrrolidin-1-yl)sulfonyl)pyridin-2-yl)piperidin-4-ol | 576.2 | CDCl3 δ 8.35 (s, 1H), 7.62-7.60 (d, J = 7.6 Hz, 1H), 7.47-7.43 (m, 3H), 7.29-7.25 (m, 1H), 6.99-6.92 (m, 6H), 6.55 (d, J = 9.2 Hz, 1H), 4.55-4.52 (m, 1H), 4.12-3.98 (m, 5H), 3.61-3.50 (m, 1H), 3.36-3.26 (m, 3H), 2.93-2.88 (m, 2H), 2.00-1.86 (m, 5H), 1.66-1.52 (m, 4H). |

| Cmpd | Structure | IUPAC name | M + 1 | 1H NMR |
| --- | --- | --- | --- | --- |
| 33 | 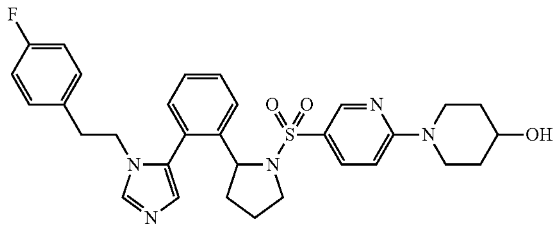 [SMILES: O=S(=O)(c1ccc(N2CCC(O)CC2)nc1)N1CCCC1c1ccccc1-c1cncn1CCc1ccc(F)cc1] | (R or S)-1-(5-((2-(2-(1-(4-fluorophenethyl)-1H-imidazol-5-yl)phenyl)pyrrolidin-1-yl)sulfonyl)pyridin-2-yl)piperidin-4-ol | 576.2 | CDCl$_3$ δ 8.35 (s, 1H), 7.62-7.60 (m, 1H), 7.49-7.44 (m, 3H), 7.29-7.26 (m, 1H), 6.99-6.92 (m, 6H), 6.56 (d, J = 9.2 Hz, 1H), 4.55-4.52 (m, 1H), 4.12-3.98 (m, 5H), 3.58-3.55 (m, 1H), 3.36-3.27 (m, 3H), 2.93-2.88 (m, 2H), 2.10-1.87 (m, 5H), 1.68-1.52 (m, 4H). |
| 34a | 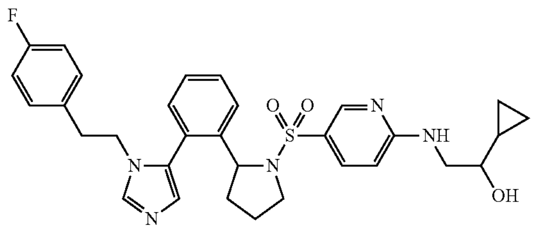 [SMILES: O=S(=O)(c1ccc(NCC(O)C2CC2)nc1)N1CCCC1c1ccccc1-c1cncn1CCc1ccc(F)cc1] | 1-cyclopropyl-2-((5-(((R or S)-2-(2-(1-(4-fluorophenethyl)-1H-imidazol-5-yl)phenyl)pyrrolidin-1-yl)sulfonyl)pyridin-2-yl)amino)ethanol | 576.2 | CDCl$_3$ δ 8.00 (s, 1H), 7.33-7.31 (m, 1H), 7.22-7.12 (m, 3H), 7.02-6.99 (m, 1H), 6.72-6.65 (m, 6H), 6.12 (d, J = 8.8 Hz, 1H), 5.36 (br, 1H), 4.27-4.24 (m, 1H), 3.80-3.76 (m, 2H), 3.28-2.85 (m, 5H), 2.66-2.61 (m, 2H), 1.73-1.61 (m, 3H), 1.41-1.26 (m, 2H), 0.71-0.69 (m, 1H), 0.31-0.26 (m, 2H), 0.11-0.09 (m, 1H), 0.02-0.01 (m, 1H). |
| 34b | 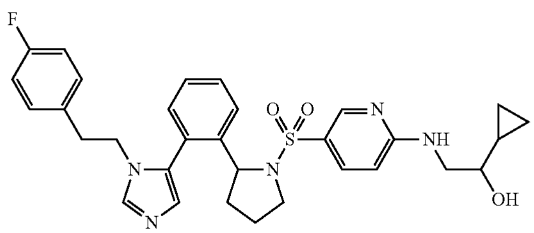 [SMILES: O=S(=O)(c1ccc(NCC(O)C2CC2)nc1)N1CCCC1c1ccccc1-c1cncn1CCc1ccc(F)cc1] | 1-cyclopropyl-2-((5-(((R or S)-2-(2-(1-(4-fluorophenethyl)-1H-imidazol-5-yl)phenyl)pyrrolidin-1-yl)sulfonyl)pyridin-2-yl)amino)ethanol | 576.2 | CDCl$_3$ δ 8.01 (s, 1H), 7.35-7.33 (m, 1H), 7.23-7.14 (m, 3H), 7.04-7.00 (m, 1H), 6.73-6.67 (m, 6H), 6.13 (d, J = 9.2 Hz, 1H), 5.51 (br, 1H), 4.91 (br, 1H), 4.28-4.25 (m, 1H), 3.81-3.77 (m, 2H), 3.42-2.87 (m, 5H), 2.67-2.63 (m, 2H), 1.70-1.62 (m, 2H), 1.43-1.28 (m, 2H), 0.72-0.70 (m, 1H), 0.30-0.27 (m, 2H), 0.13-0.11 (m, 1H), 0.03-0.01 (m, 1H). |
| 35a | 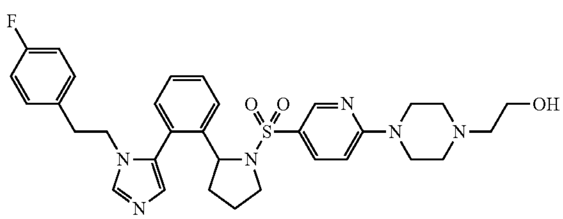 [SMILES: O=S(=O)(c1ccc(N2CCN(CCO)CC2)nc1)N1CCCC1c1ccccc1-c1cncn1CCc1ccc(F)cc1] | (R or S)-2-(4-(5-((2-(2-(1-(4-fluorophenethyl)-1H-imidazol-5-yl)phenyl)pyrrolidin-1-yl)sulfonyl)pyridin-2-yl)piperazin-1-yl)ethanol | 605.3 | CDCl$_3$ δ 8.36 (s, 1H), 7.61-7.59 (m, 1H), 7.48-7.44 (m, 3H), 7.29-7.25 (m, 1H), 6.99-6.89 (m, 6H), 6.55-6.52 (m, 1H), 4.56-4.52 (m, 1H), 4.06 (t, J = 7.2 Hz, 2H), 3.68-3.55 (m, 7H), 3.30-3.25 (m, 1H), 2.93-2.88 (m, 2H), 2.63-2.62 (m, 6H), 2.33-2.32 (br, 1H), 1.99-1.85 (m, 2H), 1.68-1.64 (m, 1H), 1.54-1.50 (m, 1H). |
| 35b | 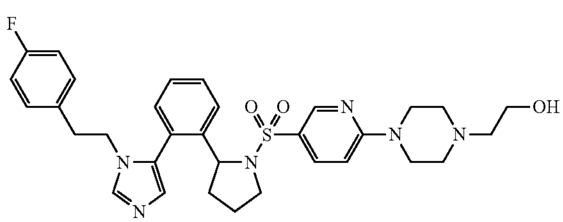 [SMILES: O=S(=O)(c1ccc(N2CCN(CCO)CC2)nc1)N1CCCC1c1ccccc1-c1cncn1CCc1ccc(F)cc1] | (R or S)-2-(4-(5-((2-(2-(1-(4-fluorophenethyl)-1H-imidazol-5-yl)phenyl)pyrrolidin-1-yl)sulfonyl)pyridin-2-yl)piperazin-1-yl)ethanol | 605.3 | CDCl$_3$ δ 8.33 (s, 1H), 7.59-7.57 (m, 1H), 7.45-7.41 (m, 3H), 7.26-7.23 (m, 1H), 6.97-6.89 (m, 6H), 6.52-6.50 (m, 1H), 4.54-4.50 (m, 1H), 4.04 (t, J = 7.2 Hz, 2H), 3.67-3.53 (m, 7H), 3.27-3.23 (m, 1H), 2.92-2.13 (m, 9H), 1.94-1.82 (m, 2H), 1.66-1.61 (m, 1H), 1.52-1.48 (m, 1H). |

-continued

| Cmpd | Structure | IUPAC name | M + 1 | ¹H NMR |
|---|---|---|---|---|
| 36 | 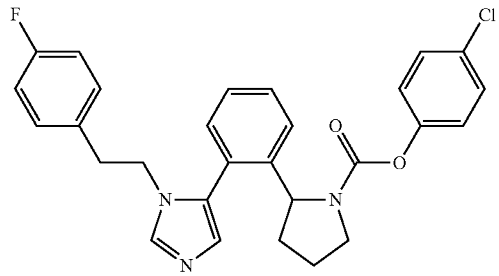 [SMILES: O=C(Oc1ccc(Cl)cc1)N1CCCC1c1ccccc1-c1cncn1CCc1ccc(F)cc1] | 4-chlorophenyl 2-(2-(1-(4-fluorophenethyl)-1H-imidazol-5-yl)phenyl)pyrrolidine-1-carboxylate | 490.2 | CD₃OD: δ 7.62 (s, 1H), 7.51-7.49 (m, 1H), 7.41-7.31 (m, 2H), 7.27-7.22 (m, 1H), 7.17 (d, J = 6.4 Hz, 1H), 7.03-7.01 (m, 2H), 6.95 (d, J = 6.8 Hz, 1H), 6.87-6.80 (m, 3H), 6.71 (t, J = 8.8 Hz, 1H), 6.59-6.52 (m, 1H), 6.50 (d, J = 2.0 Hz, 1H), 4.55-4.06 (m, 1H), 3.77-3.56 (m, 4H), 2.76-2.58 (m, 1H), 2.56-2.51 (m, 1H), 2.29-2.09 (m, 1H), 1.98-1.94 (m, 1H), 1.87-1.79 (m, 2H) |
| 37 | 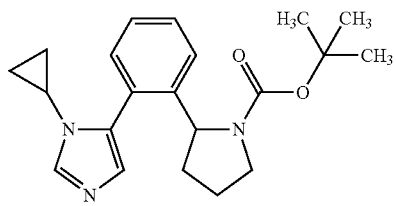 [SMILES: CC(C)(C)OC(=O)N1CCCC1c1ccccc1-c1cncn1C1CC1] | tert-butyl 2-(2-(1-cyclopropyl-1H-imidazol-5-yl)phenyl)pyrrolidine-1-carboxylate | 354.2 | CD₃OD δ 7.74 (s, 1H), 7.41-7.15 (m, 4H), 6.93 (s, 1H), 4.91 (s, 0.6H), 4.78-4.77 (m, 0.4H), 3.63-3.52 (m, 2H), 3.39 (br, 0.5H), 3.21 (br, 0.5H), 2.14-2.02 (m, 1H), 2.00-1.67 (m, 3H), 1.42-1.21 (m, 9H), 1.08 (br, 1H), 0.89-0.78 (m, 3H). |
| 38 | 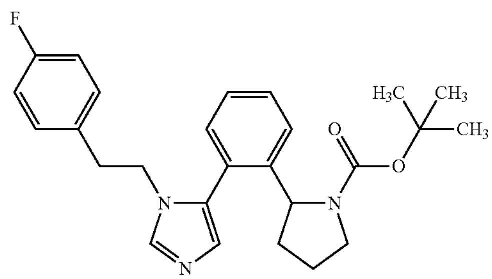 [SMILES: CC(C)(C)OC(=O)N1CCCC1c1ccccc1-c1cncn1CCc1ccc(F)cc1] | tert-butyl 2-(2-(1-(4-fluorophenethyl)-1H-imidazol-5-yl)phenyl)pyrrolidine-1-carboxylate | 436.2 | CDCl₃ δ 7.49-7.35 (m, 2H), 7.26-7.24 (m, 2H), 7.06-6.87 (m, 6H), 4.81-4.65 (m, 1H), 4.24-3.91 (m, 2H), 3.58-3.47 (m, 2H), 2.85 (br, 2H), 2.00-1.73 (m, 3H), 1.60 (br, 1H), 1.50-1.19 (m, 9H). |
| 39a | 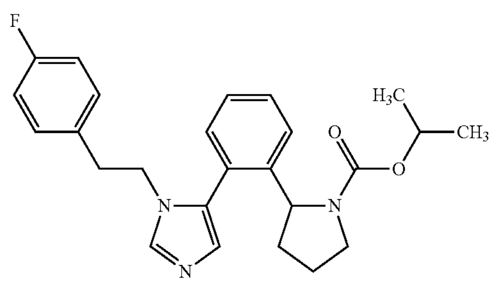 [SMILES: CC(C)OC(=O)N1CCCC1c1ccccc1-c1cncn1CCc1ccc(F)cc1] | (R or S)-isopropyl 2-(2-(1-(4-fluorophenethyl)-1H-imidazol-5-yl)phenyl)pyrrolidine-1-carboxylate | 422.2 | CD₃OD: δ 7.61-7.51 (m, 1H), 7.39-7.35 (m, 1H), 7.25-7.14 (m, 2H), 7.02-6.95 (m, 1H), 6.91-6.84 (m, 5H), 4.70-4.66 (m, 1H), 4.60-4.56 (m, 1H), 4.06-4.00 (m, 2H), 3.58-3.37 (m, 2H), 2.95-2.77 (m, 2H), 2.02-1.99 (m, 1H), 1.97-1.74 (m, 2H), 1.73-1.71 (m, 1H), 1.23-1.15 (m, 4H), 0.93 (d, J = 6.0 Hz, 1H), 0.67 (d, J = 6.4 Hz, 1H) |
| 39b | 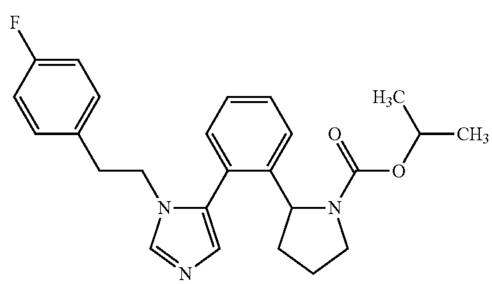 [SMILES: CC(C)OC(=O)N1CCCC1c1ccccc1-c1cncn1CCc1ccc(F)cc1] | (R or S)-isopropyl 2-(2-(1-(4-fluorophenethyl)-1H-imidazol-5-yl)phenyl)pyrrolidine-1-carboxylate | 422.2 | CD₃OD: δ 7.70 (d, J = 13.6 Hz, 1H), 7.44 (s, 1H), 7.31-7.20 (m, 2H), 7.03 (d, J = 5.2 Hz, 1H), 6.96-6.92 (m, 5H), 4.81-4.42 (m, 2H), 4.26-3.96 (m, 2H), 3.65-3.51 (m, 2H), 2.92-2.87 (m, 2H), 2.14-1.62 (m, 4H), 1.38-1.25 (m, 4H), 0.98 (d, J = 6.0 Hz, 1H), 0.72 (d, J = 6.0 Hz, 1H). |

-continued

| Cmpd | Structure | IUPAC name | M + 1 | ¹H NMR |
|---|---|---|---|---|
| 40 | 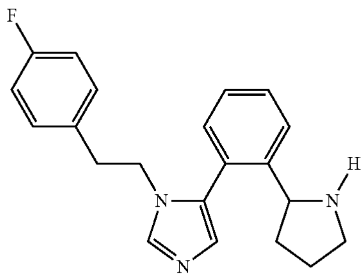 [SMILES: Fc1ccc(CCn2cncc2-c2ccccc2C2CCCN2)cc1] | 1-(4-fluorophenethyl)-5-(2-(pyrrolidin-2-yl)phenyl)-1H-imidazole | 336.2 | CD₃OD: δ 7.67-7.65 (m, 2H), 7.53 (t, J = 7.2 Hz, 1H), 7.32 (t, J = 6.4 Hz, 1H), 7.08 (dd, J₁ = 7.2 Hz, J₂ = 1.2 Hz, 1H), 6.97-6.94 (m, 5H), 4.07-4.03 (m, 2H), 3.93-3.89 (m, 1H), 3.21-3.16 (m, 1H), 2.90-2.82 (m, 3H), 2.03-1.93 (m, 2H), 1.80-1.74 (m, 1H), 1.65-1.60 (m, 1H). |
| 41 | 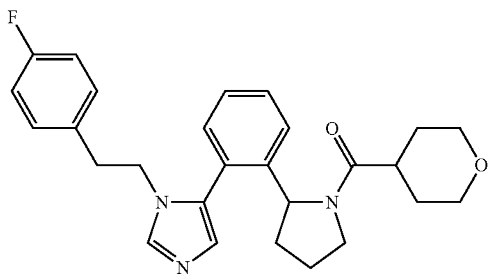 [SMILES: O=C(C1CCOCC1)N1CCCC1c1ccccc1-c1cncn1CCc1ccc(F)cc1] | (2-(2-(1-(4-fluorophenethyl)-1H-imidazol-5-yl)phenyl)pyrrolidin-1-yl)(tetrahydro-2H-pyran-4-yl)methanone | 448 | CD₃OD: δ 7.60 (s, 1H), 7.41-7.35 (m, 1H), 7.39 (t, J = 8.0 Hz, 1H), 7.21-7.18 (m, 1H), 7.00-6.90 (m, 6H), 4.80-4.78 (m, 1H), 4.35-4.28 (m, 1H), 4.18-4.10 (m, 1H), 3.99-3.90 (m, 1H), 3.81-3.60 (m, 2H), 3.55-3.45 (m, 2H), 2.91-2.82 (m, 2H), 2.08-1.98 (m, 2H), 1.90-1.61 (m, 6H). |
| 42a | 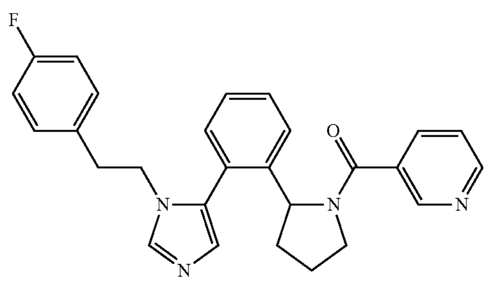 [SMILES: O=C(c1cccnc1)N1CCCC1c1ccccc1-c1cncn1CCc1ccc(F)cc1] | (R or S)-(2-(2-(1-(4-fluorophenethyl)-1H-imidazol-5-yl)phenyl)pyrrolidin-1-yl)(pyridin-3-yl)methanone | 441.2 | (CD₃OD): δ 8.80 (s, 1H), 8.79-8.68 (m, 1H), 8.09 (d, J = 7.2 Hz, 1H), 7.70 (s, 1H), 7.58-7.53 (m, 1H), 7.52-7.50 (m, 1H), 7.46-7.30 (m, 1H), 7.10-6.96 (m, 7H), 4.40-4.34 (m, 1H), 4.25-4.18 (m, 1H), 3.96-3.90 (m, 1H), 3.68-3.62 (m, 1H), 3.04-2.81 (m, 3H), 2.30-2.21 (m, 1H), 2.08-2.01 (m, 1H), 1.90-1.76 (m, 2H). |
| 42b | 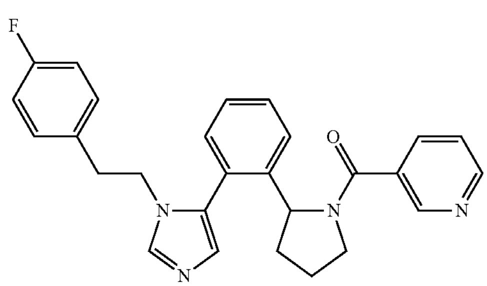 [SMILES: O=C(c1cccnc1)N1CCCC1c1ccccc1-c1cncn1CCc1ccc(F)cc1] | (R or S)-(2-(2-(1-(4-fluorophenethyl)-1H-imidazol-5-yl)phenyl)pyrrolidin-1-yl)(pyridin-3-yl)methanone | 441.2 | (CD₃OD): δ 8.80 (s, 1H), 8.79-8.68 (m, 1H), 8.09 (d, J = 7.2 Hz, 1H), 7.70 (s, 1H), 7.58-7.53 (m, 1H), 7.52-7.50 (m, 1H), 7.46-7.30 (m, 1H), 7.10-6.96 (m, 7H), 4.40-4.34 (m, 1H), 4.25-4.18 (m, 1H), 3.96-3.90 (m, 1H), 3.68-3.62 (m, 1H), 3.04-2.81 (m, 3H), 2.30-2.21 (m, 1H), 2.08-2.01 (m, 1H), 1.90-1.76 (m, 2H). |
| 43a | 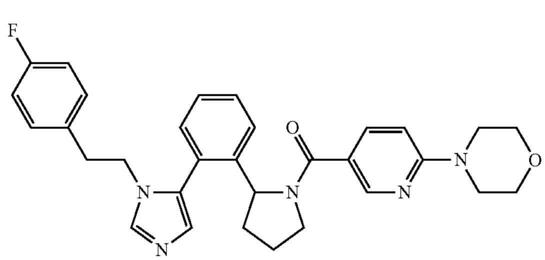 [SMILES: O=C(c1ccc(N2CCOCC2)nc1)N1CCCC1c1ccccc1-c1cncn1CCc1ccc(F)cc1] | (R or S)-(2-(2-(1-(4-fluorophenethyl)-1H-imidazol-5-yl)phenyl)pyrrolidin-1-yl)(6-morpholino-pyridin-3-yl)methanone | 526.2 | (CD₃OD): δ 8.41 (s, 1H), 7.79 (d, J = 7.6 Hz, 1H), 7.61 (s, 1H), 7.46 (s, 1H), 7.28-7.16 (m, 2H), 7.02-6.91 (m, 7H), 6.80 (d, J = 4.4 Hz, 1H), 4.29 (s, 1H), 4.15 (s, 1H), 3.93-3.91 (m, 1H), 3.76 (s, 6H), 3.57 (s, 4H), 2.91 (t, J = 6.4 Hz, 2H), 2.19 (d, J = 8.0 Hz, 1H), 1.96 (s, 1H), 1.73-1.70 (m, 2H). |

| Cmpd | Structure | IUPAC name | M + 1 | ¹H NMR |
|---|---|---|---|---|
| 43b | 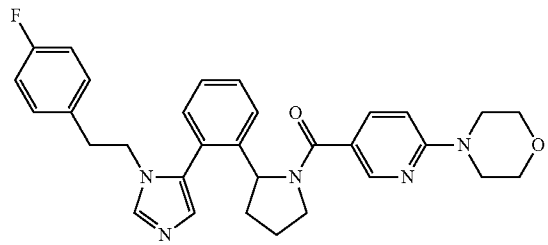 [SMILES: O=C(c1ccc(N2CCOCC2)nc1)N1CCCC1c1ccccc1-c1cncn1CCc1ccc(F)cc1] | (R or S)-(2-(2-(1-(4-fluorophenethyl)-1H-imidazol-5-yl)phenyl)pyrrolidin-1-yl)(6-morpholinopyridin-3-yl)methanone | 526.2 | (CD₃OD): δ 8.41 (s, 1H), 7.79 (d, J = 7.6 Hz, 1H), 7.61 (s, 1H), 7.46 (s, 1H),, 7.28-7.16 (m, 2H), 7.02-6.91 (m, 7H), 6.80 (d, J = 4.4 Hz, 1H), 4.29 (s, 1H), 4.15 (s, 1H), 3.93-3.91 (m, 1H), 3.76 (s, 6H), 3.57 (s, 4H), 2.91 (t, J = 6.4 Hz, 2H), 2.19 (d, J = 8.0 Hz, 1H), 1.96 (s, 1H), 1.73-1.70 (m, 2H). |
| 44a | 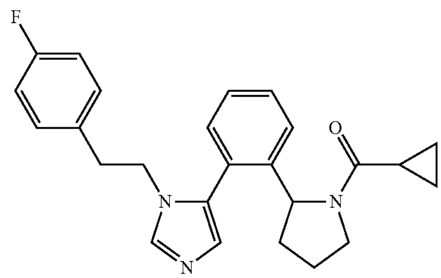 [SMILES: O=C(C1CC1)N1CCCC1c1ccccc1-c1cncn1CCc1ccc(F)cc1] | (R or S)-cyclopropyl(2-(2-(1-(4-fluorophenethyl)-1H-imidazol-5-yl)phenyl)pyrrolidin-1-yl)methanone | 404.2 | (CD₃OD): δ 7.48 (d, J = 4.8 Hz, 1H), 7.42-7.33 (m, 1H), 7.31-7.21 (m, 1H), 7.20-7.19 (m, 1H), 7.00-6.91 (m, 5H), 6.89 (d, J = 8.0 Hz, 1H), 4.79 (d, J = 8.0 Hz, 1H), 4.29-4.21 (m, 1H), 4.11-4.02 (m, 1H), 4.00-3.91 (m, 1H), 3.89-3.82 (m, 1H), 2.91-2.89 (m, 2H), 2.09-1.99 (m, 2H), 1.95-1.89 (m, 2H), 1.85-1.81 (m, 1H), 1.68-1.62 (m, 1H), 0.82 (d, J = 6.4 Hz, 3H). |
| 44b | 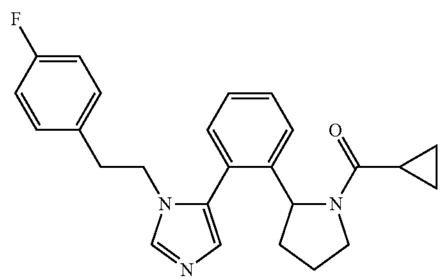 [SMILES: O=C(C1CC1)N1CCCC1c1ccccc1-c1cncn1CCc1ccc(F)cc1] | (R or S)-cyclopropyl(2-(2-(1-(4-fluorophenethyl)-1H-imidazol-5-yl)phenyl)pyrrolidin-1-yl)methanone | 404.2 | (CD₃OD): δ 7.49 (d, J = 4.8 Hz, 1H), 7.41-7.32 (m, 1H), 7.31-7.21 (m, 1H), 7.20-7.19 (m, 1H), 7.00-6.91 (m, 5H), 6.89 (d, J = 8.0 Hz, 1H), 4.79 (d, J = 8.0 Hz, 1H), 4.29-4.21 (m, 1H), 4.11-4.02 (m, 1H), 4.00-3.91 (m, 1H), 3.89-3.82 (m, 1H), 2.91-2.89 (m, 2H), 2.09-1.99 (m, 2H), 1.95-1.89 (m, 2H), 1.85-1.81 (m, 1H), 1.68-1.62 (m, 1H), 0.82 (d, J = 6.4 Hz, 3H). |
| 45a | 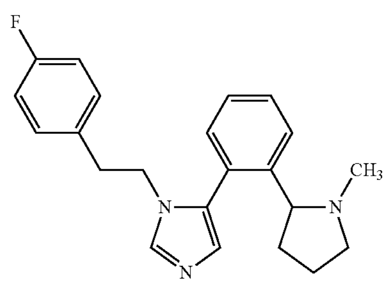 [SMILES: CN1CCCC1c1ccccc1-c1cncn1CCc1ccc(F)cc1] | (R or S)-1-(4-fluorophenethyl)-5-(2-(1-methylpyrrolidin-2-yl)phenyl)-1H-imidazole | 349.2 | (CD₃OD): δ 7.55 (d, J = 7.6 Hz, 1H), 7.47 (s, 1H), 7.37 (t, J = 4.0 Hz, 1H), 7.16 (t, J = 6.0 Hz, 1H), 6.87 (d, J = 0.8 Hz, 1H), 6.85-6.73 (m, 4H), 6.68 (s, 1H), 3.82 (s, 2H), 3.02-2.98 (m, 1H), 2.86-2.81 (m, 1H), 2.68-2.64 (m, 2H), 2.05-2.01 (m, 1H), 1.98-1.90 (m, 4H), 1.77-1.72 (m, 1H), 1.63-1.55 (m, 2H). |
| 45b | 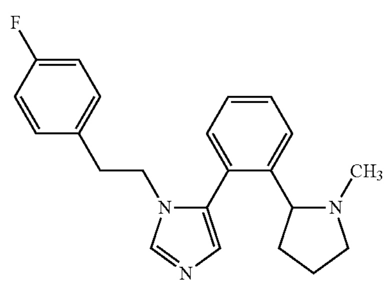 [SMILES: CN1CCCC1c1ccccc1-c1cncn1CCc1ccc(F)cc1] | (R or S)-1-(4-fluorophenethyl)-5-(2-(1-methylpyrrolidin-2-yl)phenyl)-1H-imidazole | 349.2 | (CD₃OD): δ 7.63 (d, J = 8.0 Hz, 1H), 7.55 (s, 1H), 7.45 (t, J = 7.6 Hz, 1H), 7.24 (t, J = 7.6 Hz, 1H), 6.95 (d, J = 7.6 Hz, 1H), 6.91-6.81 (m, 3H), 6.77 (s, 1H), 3.95-3.91 (m, 2H), 3.19 (t, J = 8.0 Hz, 1H), 2.91 (t, J = 4.0 Hz, 1H), 2.75 (t, J = 4.0 Hz, 2H), 2.39-2.32 (m, 1H), 2.14-2.08 (m, 1H), 1.90-1.85 (m, 1H), 1.74-1.64 (m, 2H), 1.42-1.25 (m, 1H). |

-continued

| Cmpd | Structure | IUPAC name | M + 1 | ¹H NMR |
|---|---|---|---|---|
| 46a | 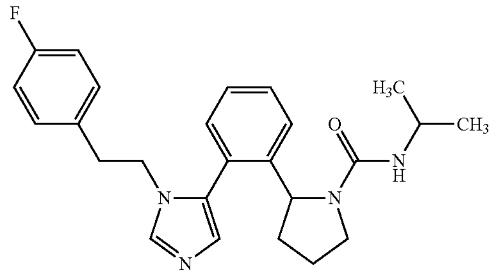 [SMILES: CC(C)NC(=O)N1CCCC1c1ccccc1-c1cncn1CCc1ccc(F)cc1] | (R or S)-2-(2-(1-(4-fluorophenethyl)-1H-imidazol-5-yl)phenyl)-N-isopropyl-pyrrolidine-1-carboxamide | 421.2 | (CD₃OD): δ 7.63 (s, 1H), 7.45 (t, J = 4.0 Hz, 1H), 7.32-7.26 (m, 2H), 7.05-7.00 (m, 3H), 6.99-6.95 (m, 3H), 4.81-4.79 (m, 1H), 4.31-4.12 (m, 2H), 3.89-3.82 (m, 1H), 3.68-3.62 (m, 1H), 3.48-3.41 (m, 1H), 2.99-2.85 m, 2H), 2.09-1.95 (m, 2H), 1.90-1.84 (m, 1H), 1.65-1.60 (m, 1H), 1.17-1.12 (d, J = 13.2 Hz, 6H). |
| 46b | 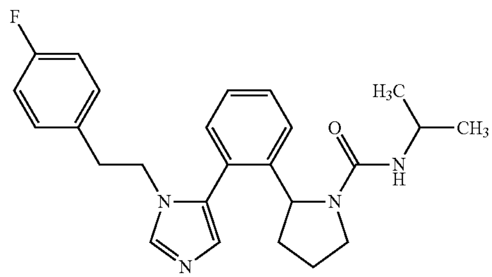 [SMILES: CC(C)NC(=O)N1CCCC1c1ccccc1-c1cncn1CCc1ccc(F)cc1] | (R or S)-2-(2-(1-(4-fluorophenethyl)-1H-imidazol-5-yl)phenyl)-N-isopropyl-pyrrolidine-1-carboxamide | 421.2 | (CD₃OD): δ 7.63 (s, 1H), 7.45 (t, J = 4.0 Hz, 1H), 7.32-7.26 (m, 2H), 7.05-7.00 (m, 3H), 6.99-6.95 (m, 3H), 4.81-4.79 (m, 1H), 4.31-4.12 (m, 2H), 3.89-3.82 (m, 1H), 3.68-3.62 (m, 1H), 3.48-3.41 (m, 1H), 2.99-2.85 (m, 2H), 2.09-1.95 (m, 2H), 1.90-1.84 (m, 1H), 1.65-1.60 (m, 1H), 1.17-1.12 (d, J = 13.2 Hz, 6H). |
| 47 | 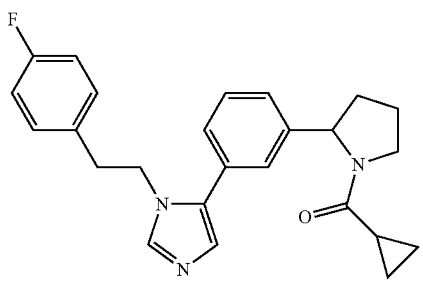 [SMILES: O=C(C1CC1)N1CCCC1c1cccc(-c2cncn2CCc2ccc(F)cc2)c1] | cyclopropyl(2-(3-(1-(4-fluorophenethyl)-1H-imidazol-5-yl)phenyl) pyrrolidin-1-yl)methanone | 404.2 | (CD₃OD): δ 7.56-7.39 (m, 2H), 7.32-7.13 (m, 3H), 6.97-6.89 (m, 5H), 5.39-5.36 (m, 1H), 4.34-4.28 (m, 2H), 4.12-3.92 (m, 1H), 3.75-3.68 (m, 1H), 2.81-2.77 (m, 2H), 2.61-2.35 (m, 1H), 2.05-1.89 (m, 3H), 1.75-1.46 (m, 1H), 0.89-0.39 (m, 4H). |
| 48a | 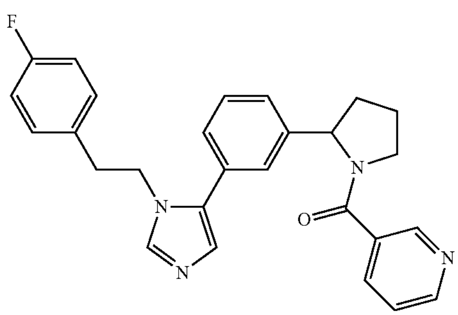 [SMILES: O=C(c1cccnc1)N1CCCC1c1cccc(-c2cncn2CCc2ccc(F)cc2)c1] | (R or S)-(2-(3-(1-(4-fluorophenethyl)-1H-imidazol-5-yl)phenyl) pyrrolidin-1-yl) (pyridin-3-yl) methanone | 441.2 | (CD₃OD): δ 8.76-8.61 (m, 1H), 8.33-8.04 (m, 1H), 7.61-7.32 (m, 4H), 7.30-7.09 (m, 2H), 7.07-6.78 (m, 6H), 5.24-4.99 (m, 1H), 4.29-4.16 (m, 2H), 3.91-3.62 (m, 2H), 2.72-2.71 (m, 12H), 2.49-2.46 (m, 1H), 2.05-1.88 (m, 3H). |
| 48b | 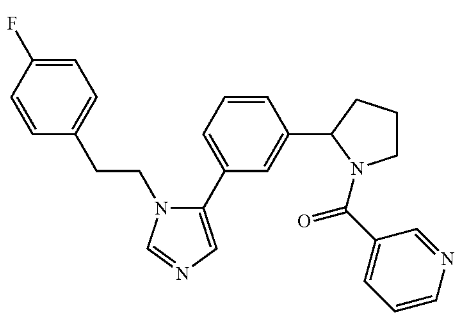 [SMILES: O=C(c1cccnc1)N1CCCC1c1cccc(-c2cncn2CCc2ccc(F)cc2)c1] | (R or S)-(2-(3-(1-(4-fluorophenethyl)-1H-imidazol-5-yl)phenyl) pyrrolidin-1-yl) (pyridin-3-yl) methanone | 441.2 | (CD₃OD): δ 8.77-8.62 (m, 1H), 8.33-8.04 (m, 1H), 7.61-7.41 (m, 4H), 7.34-7.09 (m, 2H), 7.07-6.78 (m, 6H), 5.24-4.99 (m, 1H), 4.29-4.16 (m, 2H), 3.91-3.62 (m, 2H), 2.72-2.71 (m, 12H), 2.49-2.46 (m, 1H), 2.05-1.88 (m, 3H). |

-continued

| Cmpd | Structure | IUPAC name | M + 1 | ¹H NMR |
|---|---|---|---|---|
| 49a | 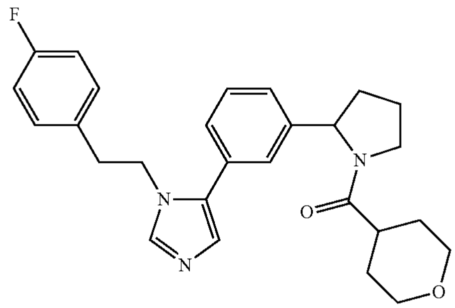 [SMILES: O=C(C1CCOCC1)N1CCCC1c1cccc(-c2cncn2CCc2ccc(F)cc2)c1] | (R or S)-(2-(3-(1-(4-fluorophenethyl)-1H-imidazol-5-yl)phenyl)pyrrolidin-1-yl)(tetrahydro-2H-pyran-4-yl)methanone | 448.2 | (CD$_3$OD): δ 7.57 (s, 1H), 7.47-7.35 (m, 1H), 7.30-7.26 (m, 1H), 7.21-7.09 (m, 2H), 6.96-6.87 (m, 5H), 5.24-5.11 (m, 1H), 4.31-4.26 (m, 2H), 3.93-3.88 (m, 2H), 3.86-3.79 (m, 1H), 3.79-3.62 (m, 1H), 3.49-3.47 (m, 1H), 3.26-3.24 (m, 0.5H), 2.90-2.87 (m, 1H), 2.79-2.74 (m, 2H), 2.52-2.49 (m, 1H), 2.41-2.29 (m, 0.5H), 1.99-1.94 (m, 3H), 1.73-1.62 (m, 1H) |
| 49b | 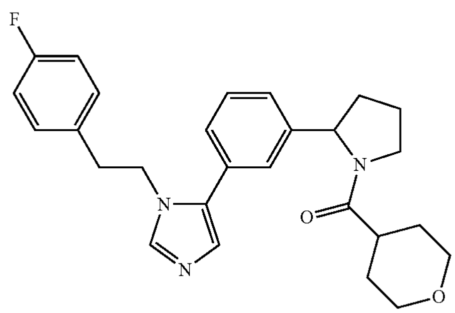 [SMILES: O=C(C1CCOCC1)N1CCCC1c1cccc(-c2cncn2CCc2ccc(F)cc2)c1] | (R or S)-(2-(3-(1-(4-fluorophenethyl)-1H-imidazol-5-yl)phenyl)pyrrolidin-1-yl)(tetrahydro-2H-pyran-4-yl)methanone | 448.2 | (CD$_3$OD): δ 7.54 (d, J = 9.6 Hz, 1H), 7.47-7.35 (m, 1H), 7.30-7.25 (m, 1H), 6.96-6.87 (m, 5H), 5.24-5.11 (m, 1H), 4.31-4.26 (m, 2H), 3.93-3.88 (m, 2H), 3.86-3.79 (m, 1H), 3.79-3.62 (m, 1H), 3.49-3.47 (m, 1H), 3.26-3.24 (m, 0.5H), 2.90-2.87 (m, 1H), 2.79-2.74 (m, 2H), 2.52-2.49 (m, 1H), 2.41-2.29 (m, 0.5H), 1.99-1.94 (m, 3H), 1.73-1.62 (m, 1H). |
| 50 | 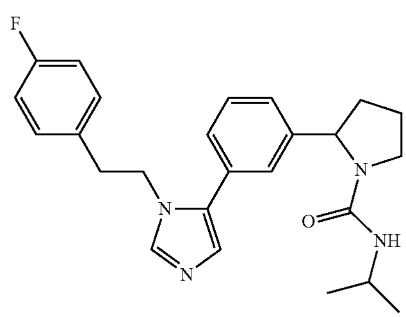 [SMILES: CC(C)NC(=O)N1CCCC1c1cccc(-c2cncn2CCc2ccc(F)cc2)c1] | 2-(3-(1-(4-fluorophenethyl)-1H-imidazol-5-yl)phenyl)-N-isopropyl-pyrrolidine-1-carboxamide | 421.2 | (CD$_3$OD): δ 7.54 (s, 1H), 7.44 (t, J = 8.0 Hz, 1H), 7.29-7.19 (m, 3H), 6.93 (t, J = 7.2 Hz, 5H), 5.07-5.04 (m, 1H), 4.32 (t, J = 6.8 Hz, 2H), 3.86-3.80 (m, 1H), 3.69-3.64 (m, 1H), 3.55-3.44 (m, 1H), 2.81 (t, J = 6.8 Hz, 2H), 2.43-2.35 (m, 1H), 1.98-1.84 (m, 3H), 1.11 (d, J = 6.8 Hz, 3H), 1.08 (d, J = 6.8 Hz, 3H). |
| 51 | 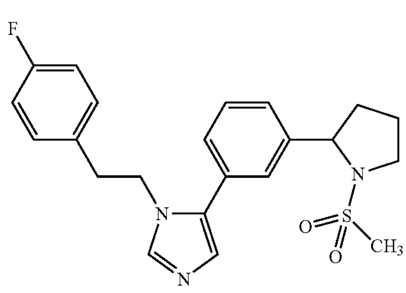 [SMILES: CS(=O)(=O)N1CCCC1c1cccc(-c2cncn2CCc2ccc(F)cc2)c1] | 1-(4-fluorophenethyl)-5-(3-(1-(methylsulfonyl)pyrrolidin-2-yl)phenyl)-1H-imidazole | 414.2 | (CD$_3$OD): δ 7.70 (s, 1H), 7.45 (d, J = 4.8 Hz, 2H), 7.39 (s, 2H), 7.25-7.23 (m, 1H), 7.02 (s, 1H), 6.93-6.90 (m, 4H), 4.94-4.91 (m, 1H), 4.38-4.34 (m, 2H), 3.65-3.56 (m, 2H), 2.93 (s, 3H), 2.81 (t, J = 6.8 Hz, 2H), 2.49-2.43 (m, 1H), 2.03-1.93 (m, 3H). |

-continued

| Cmpd | Structure | IUPAC name | M + 1 | ¹H NMR |
|---|---|---|---|---|
| 52 | 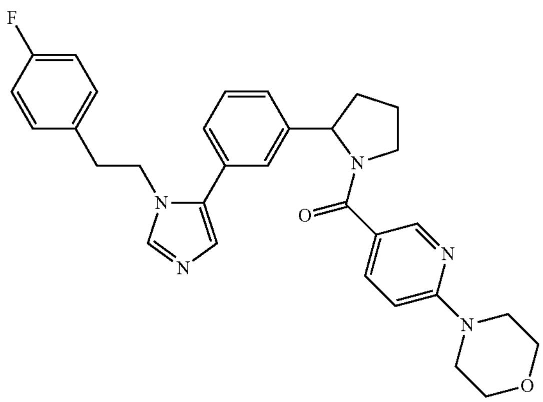 [SMILES: O=C(c1ccc(N2CCOCC2)nc1)N1CCCC1c1cccc(-c2cncn2CCc2ccc(F)cc2)c1] | (2-(3-(1-(4-fluorophenethyl)-1H-imidazol-5-yl)phenyl)pyrrolidin-1-yl)(6-morpholino-pyridin-3-yl)methanone | 526.2 | (CD$_3$OD): δ 8.40-7.79 (m, 2H), 7.52-7.16 (m, 5H), 6.90-6.80 (m, 6H), 5.23-5.13 (m, 1H), 4.25 (s, 2H), 3.95-3.32 (m, 10H), 2.70 (s, 2H), 2.48 (s, 1H), 2.09-1.91 (m, 3H). |
| 53a | 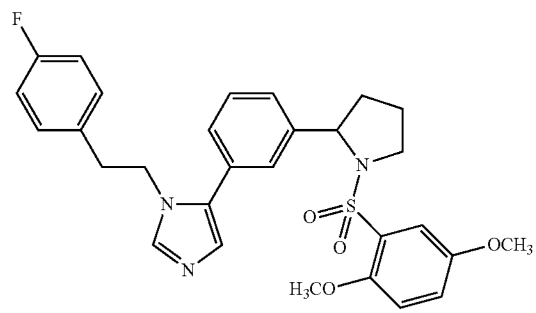 [SMILES: COc1ccc(OC)c(S(=O)(=O)N2CCCC2c2cccc(-c3cncn3CCc3ccc(F)cc3)c2)c1] | (R or S)-5-(3-(1-((2,5-dimethoxyphenyl)sulfonyl)pyrrolidin-2-yl)phenyl)-1-(4-fluorophenethyl)-1H-imidazole | 536.2 | (CD$_3$OD): δ 7.53 (s, 1H), 7.34-7.23 (m, 4H), 7.14-7.08 (m, 4H), 7.14-7.08 (m, 3H), 6.91-6.83 (m, 5H), 5.06-5.03 (m, 1H), 4.35-4.32 (m, 2H), 3.90 (s, 3H), 3.68 (s, 3H), 3.63-3.60 (m, 1H), 3.59-3.47 (m, 1H), 2.76 (d, J = 6.8 Hz, 2H), 2.30-2.23 (m, 1H), 1.92-1.79 (m, 1H) |
| 53b | 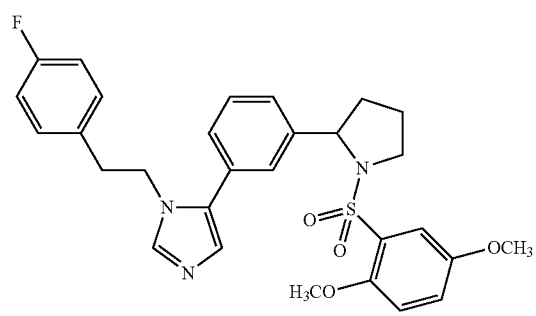 [SMILES: COc1ccc(OC)c(S(=O)(=O)N2CCCC2c2cccc(-c3cncn3CCc3ccc(F)cc3)c2)c1] | (R or S)-5-(3-(1-((2,5-Dimethoxy-phenyl)sulfonyl)pyrrolidin-2-yl)phenyl)-1-(4-fluorophenethyl)-1H-imidazole | 536.2 | (CD$_3$OD): δ 7.53 (s, 1H), 7.34-7.23 (m, 4H), 7.14-7.08 (m, 4H), 7.14-7.08 (m, 3H), 6.91-6.83 (m, 5H), 5.06-5.03 (m, 1H), 4.35-4.32 (m, 2H), 3.90 (s, 3H), 3.68 (s, 3H), 3.63-3.60 (m, 1H), 3.59-3.47 (m, 1H), 2.76 (d, J = 6.8 Hz, 2H), 2.30-2.23 (m, 1H), 1.92-1.79 (m, 1H) |
| 54 | 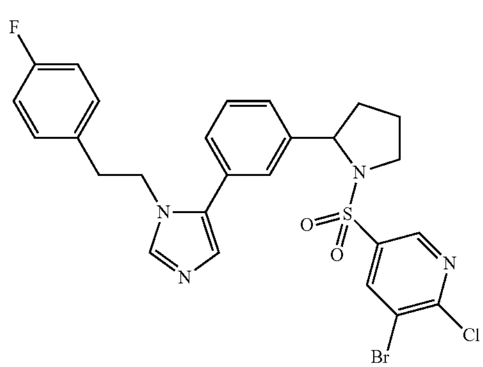 [SMILES: O=S(=O)(c1cnc(Cl)c(Br)c1)N1CCCC1c1cccc(-c2cncn2CCc2ccc(F)cc2)c1] | 3-Bromo-2-chloro-5-((2-(3-(1-(4-fluorophenethyl)-1H-imidazol-5-yl)phenyl)pyrrolidin-1-yl)sulfonyl)pyridine | 591.2 | (CD$_3$OD): δ 8.59 (s, 1H), 8.19 (s, 1H), 7.57 (s, 1H), 7.36-7.18 (m, 4H), 6.95-6.84 (m, 5H), 4.90-4.86 (m, 1H), 4.35-4.26 (m, 2H), 3.72-3.58 (m, 2H), 2.78 (t, J = 6.8 Hz, 2H), 2.36-2.22 (m, 1H), 2.01-1.82 (m, 3H). |

-continued

| Cmpd | Structure | IUPAC name | M + 1 | ¹H NMR |
|---|---|---|---|---|
| 55a | 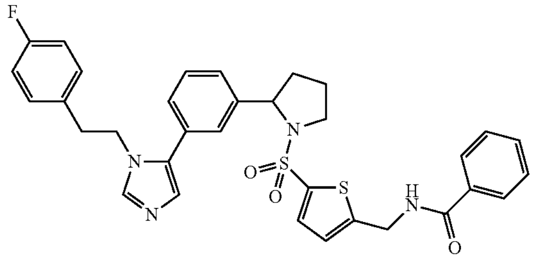 [SMILES: O=C(NCc1ccc(S(=O)(=O)N2CCCC2c2cccc(-c3cncn3CCc3ccc(F)cc3)c2)s1)c1ccccc1] | (R or S)-N-((5-((2-(3-(1-(4-fluorophenethyl)-1H-imidazol-5-yl)phenyl)pyrrolidin-1-yl)sulfonyl)thiophen-2-yl)methyl)benzamide | 615.2 | (CD$_3$OD): δ 7.83 (d, J = 7.2 Hz, 2H), 7.54-7.49 (m, 3H), 7.48-7.41 (m, 2H), 7.40-7.31 (m, 3H), 7.20-7.11 (m, 2H), 6.90-6.81 (m, 5H), 4.75-4.72 (m, 3H), 4.25-4.23 (m, 2H), 3.68-3.59 (m, 1H), 3.49-3.40 (m, 1H), 2.74 (t, J = 6.8 Hz, 2H), 2.10-2.01 (m, 1H), 1.89-1.75 (m, 2H), 1.68-7.57 (m, 1H). |
| 55b | 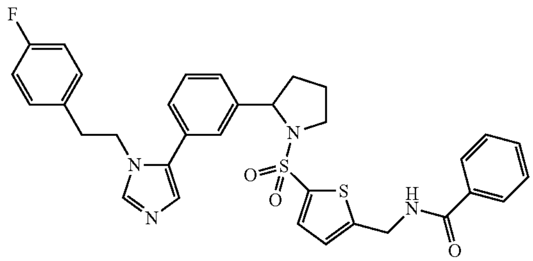 [SMILES: O=C(NCc1ccc(S(=O)(=O)N2CCCC2c2cccc(-c3cncn3CCc3ccc(F)cc3)c2)s1)c1ccccc1] | (R or S)-N-((5-((2-(3-(1-(4-fluorophenethyl)-1H-imidazol-5-yl)phenyl)pyrrolidin-1-yl)sulfonyl)thiophen-2-yl)methyl)benzamide | 615.2 | (CD$_3$OD): δ 7.83 (d, J = 7.2 Hz, 2H), 7.54-7.49 (m, 3H), 7.48-7.41 (m, 2H), 7.40-7.31 (m, 3H), 7.20-7.11 (m, 2H), 6.90-6.81 (m, 5H), 4.75-4.72 (m, 3H), 4.25-4.23 (m, 2H), 3.68-3.59 (m, 1H), 3.49-3.40 (m, 1H), 2.74 (t, J = 6.8 Hz, 2H), 2.10-2.01 (m, 1H), 1.89-1.75 (m, 2H), 1.68-7.57 (m, 1H). |
| 56 | 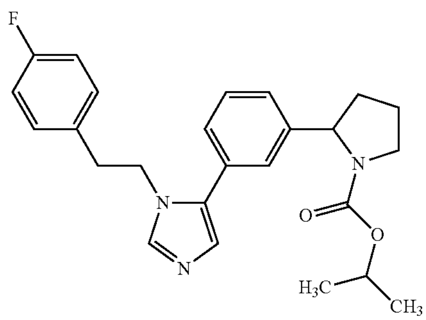 [SMILES: CC(C)OC(=O)N1CCCC1c1cccc(-c2cncn2CCc2ccc(F)cc2)c1] | Isopropyl 2-(3-(1-(4-fluorophenethyl)-1H-imidazol-5-yl)phenyl)pyrrolidine-1-carboxylate | 422.2 | (CD$_3$OD): δ 7.51 (s, 1H), 7.44-7.40 (m, 1H), 7.28-7.17 (m, 3H), 6.96-6.92 (m, 5H), 4.97-4.93 (m, 1H), 4.79-4.65 (m, 1H), 4.27 (t, J = 6.8 Hz, 2H), 3.66-3.58 (m, 2H), 2.81 (t, J = 6.8 Hz, 2H), 2.50-2.35 (m, 1H), 1.96-1.89 (m, 3H), 1.32-1.21 (m, 3H), 1.19-1.10 (m, 1.5H), 0.79-0.77 (m, 1.5H). |
| 57a | 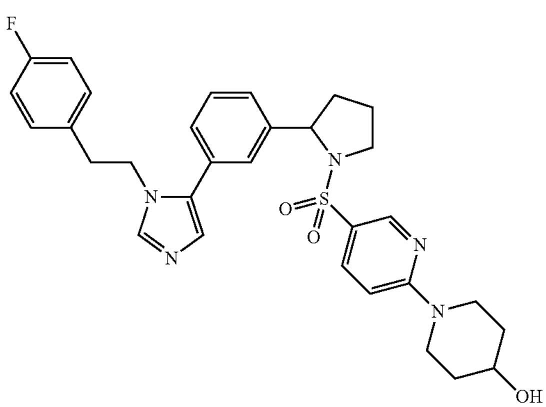 [SMILES: O=S(=O)(c1ccc(N2CCC(O)CC2)nc1)N1CCCC1c1cccc(-c2cncn2CCc2ccc(F)cc2)c1] | (R or S)-1-(5-((2-(3-(1-(4-fluorophenethyl)-1H-imidazol-5-yl)phenyl)pyrrolidin-1-yl)sulfonyl)pyridin-2-yl)piperidin-4-ol | 576.2 | (CD$_3$OD): δ 8.44 (s, 1H), 7.80 (t, J = 9.2 Hz, 1H), 7.56 (s, 1H), 7.41-7.34 (m, 3H), 7.23-7.21 (m, 1H), 6.94-6.84 (m, 6H), 4.79-4.77 (m, 1H), 4.41-4.29 (m, 2H), 4.28-4.15 (m, 2H), 3.92-3.86 (m, 1H), 3.69-3.59 (m, 1H), 3.51-3.41 (m, 1H), 3.28 (s, 1H), 2.82 (d, J = 6.8 Hz, 2H), 2.21-2.11 (m, 1H), 1.98-1.69 (m, 6H), 1.54-1.47 (m, 2H). |

| Cmpd | Structure | IUPAC name | M + 1 | ¹H NMR |
|---|---|---|---|---|
| 57b | (structure shown) | (R or S)-1-(5-((2-(3-(1-(4-fluorophenethyl)-1H-imidazol-5-yl)phenyl)pyrrolidin-1-yl)sulfonyl)pyridin-2-yl)piperidin-4-ol | 576.2 | (CD₃OD): δ 8.44 (s, 1H), 7.80 (t, J = 9.2 Hz, 1H), 7.56 (s, 1H), 7.41-7..34 (m, 3H), 7.23-7.21 (m, 1H), 6.94-6.84 (m, 6H), 4.79-4.77 (m, 1H), 4.41-4.29 (m, 2H), 4.28-4.15 (m, 2H), 3.92-3.86 (m, 1H), 3.69-3.59 (m, 1H), 3.51-3.41 (m, 1H), 3.28 (s, 1H), 2.82 (d, J = 6.8 Hz, 2H), 2.21-2.11 (m 1H), 1.98-1.69 (m, 6H), 1.54-1.47 (m, 2H). |

Example 58

5-((5-(1-(4-fluorophenethyl)-1H-imidazol-5-yl)-3,4-dihydroisoquinolin-2(1H)-yl)sulfonyl)-2-(4-methylpiperazin-1-yl)thiazole (Compound 58)

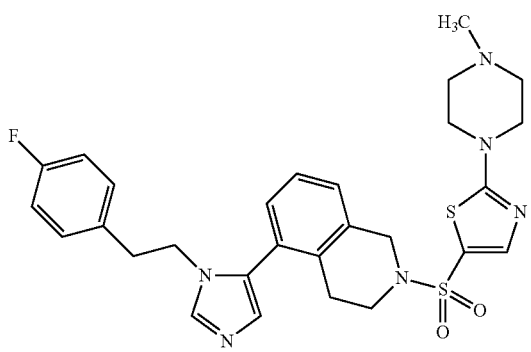 [SMILES: CN1CCN(c2ncc(S(=O)(=O)N3CCc4c(cccc4-c4cncn4CCc4ccc(F)cc4)C3)s2)CC1]

Step A—Preparation of Int 58-1

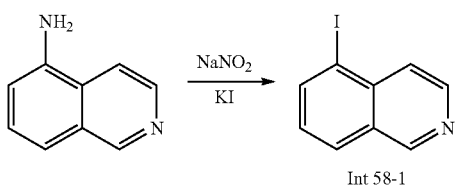

To a solution of 5-aminoisoquinoline (14 g, 97.2 mmol) in HCl/H₂O (40 mL/40 mL) was added NaNO₂ (8 g, 116 mmol) by portions at 0° C. The mixture was stirred at 0° C. for 1 hour then KI (32 g, 194 mmol) was added slowly and the mixture was refluxed overnight. After cooling to room temperature, the mixture was poured into NH₄OH (40 mL) and extracted with DCM (50 mL×3). The combined organic layers were washed with brine (40 mL), dried and concentrated. The residue was purified by column chromatography (EtOAc:Petroleum Ether=1:10) to give Int 58-1 (6.5 g). MS (ESI): m/z (M+H)⁺ 256.

Step B—Preparation of Int 58-2

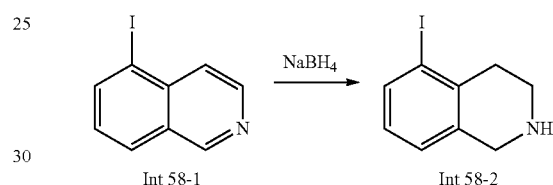

To a solution of Int 58-1 (3 g, 11.8 mmol) in AcOH (20 mL) was added NaBH₄ (1.3 g, 35.3 mmol) by portions at 0° C. The mixture was stirred at room temperature for 3 h, poured into NH₄OH (40 mL) and extracted with DCM (50 mL*3). The combined organic layers were washed with brine (40 mL), dried and concentrated. The residue was purified by column chromatography (EtOAc:Petroleum Ether=1:3) to give Int 58-2. ¹H NMR (CDCl₃): δ 7.67 (d, J=7.6 Hz, 1H), 6.98 (d, J=7.6 Hz, 1H), 6.84 (t, J=7.6 Hz, 1H), 3.94 (s, 2H), 3.14 (t, J=6.0 Hz, 2H), 2.65 (d, J=4.8 Hz, 2H). MS (ESI): m/z (M+H)⁺ 260.

Step C—Preparation of Int 58-3

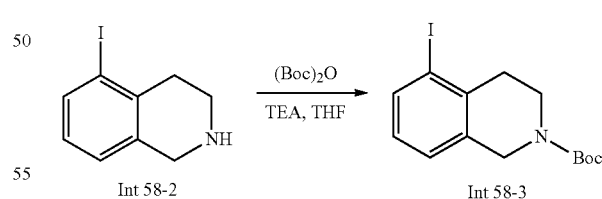

To a solution of Int 58-2 (3 g, 11.8 mmol) and TEA (3.5 g, 34.7 mmol) in THF (20 mL) was added (Boc)₂O (3.7 g, 17.25 mmol) at 0° C. The mixture was stirred at room temperature overnight, diluted with water (20 mL) and extracted with DCM (20 mL*3). The combined organic extracts were washed with brine (20 mL) and concentrated. The residue was purified by column chromatography (EtOAc:Petroleum Ether=1:10) to give Int 58-3 (4 g). MS (ESI): m/z (M+H)⁺ 360.

Step D—Preparation of Int 58-4

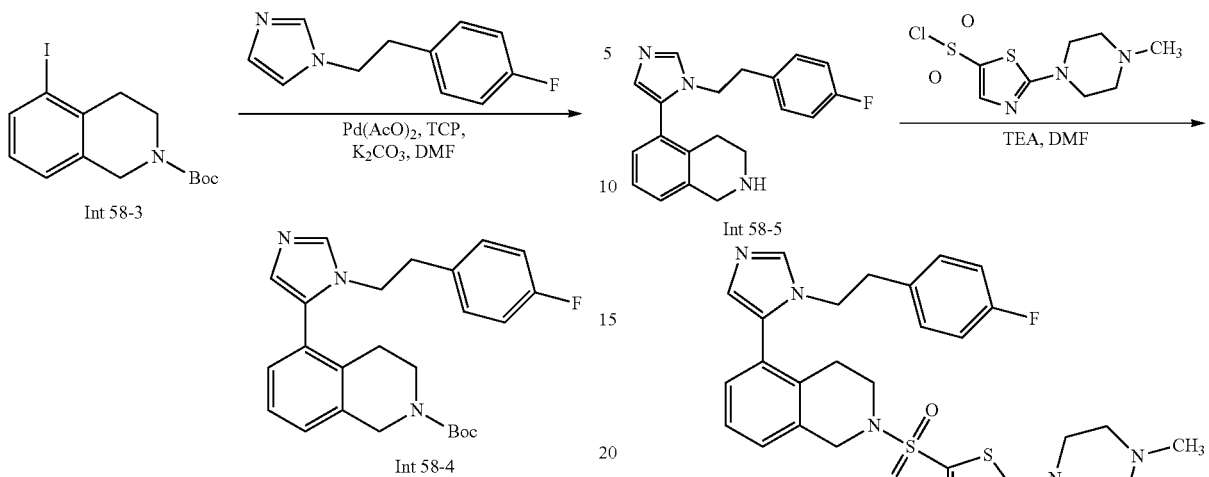

To a degassed solution of Int 58-3 (200 mg, 0.56 mmol), Cy₃P (33 mg, 0.12 mmol), Int 3-1 (106 mg, 0.56 mmol) and K₂CO₃ (232 mg, 1.68 mmol) in DMF (5 mL) was added Pd(OAc)₂ (13 mg, 0.06 mmol) under N₂ protection. The mixture was heated to 130° C. overnight then cooled and filtered through celite pad. The filtrate was extracted with EtOAc (3×10 mL) and the combined organic extracts were washed with water (15 mL) and brine (20 mL), dried over Na₂SO₄, filtered and concentrated. The residue was purified by silica gel column chromatography (EtOAc:Petroleum Ether=1:3) to Int 58-4 (100 mg). $^1$H NMR (CD₃OD): 7.69 (s, 1H), 7.26 (q, J=4.4 Hz, 2H), 7.06-7.10 (m, 1H), 6.94-6.98 (m, 1H), 6.84-6.92 (m, 4H), 4.59 (d, J=0.4 Hz, 2H), 4.04 (t, J=6.8 Hz, 2H), 3.50 (t, J=5.6 Hz, 2H), 2.78 (t, J=6.8 Hz, 2H), 2.47 (t, J=6.0 Hz, 2H), 1.46 (s, 9H). MS (ESI): m/z (M+H)⁺ 422.

Step E—Preparation of Int 58-5

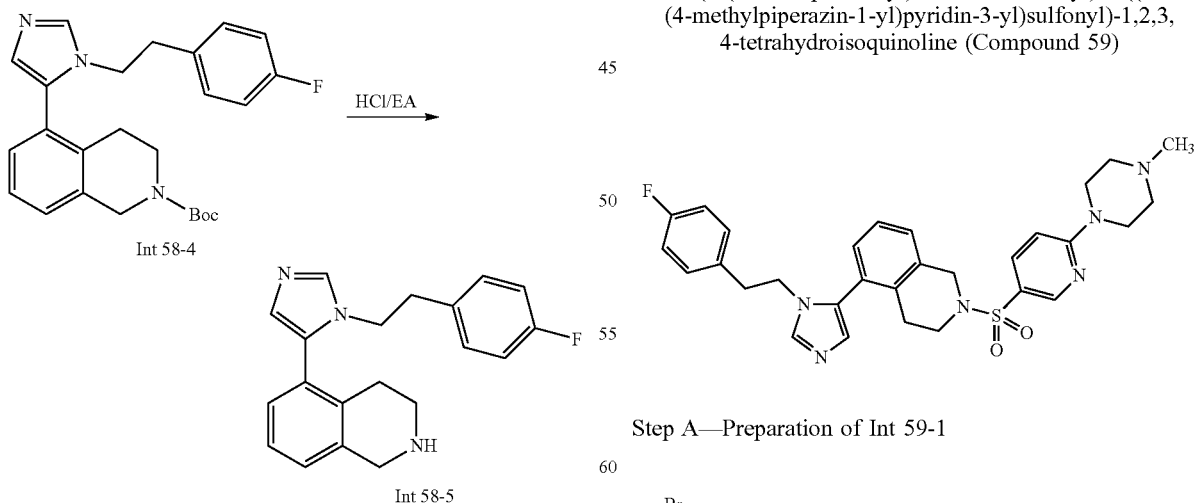

A solution of Int 58-4 (100 mg, 0.24 mmol) in HCl/EtOAc (4N, 6 mL) was stirred at room temperature overnight, concentrated in vacuum to give the product Int 58-5 (76 mg). MS (ESI): m/z (M+H)⁺ 322.

Step F—Preparation of Compound 58

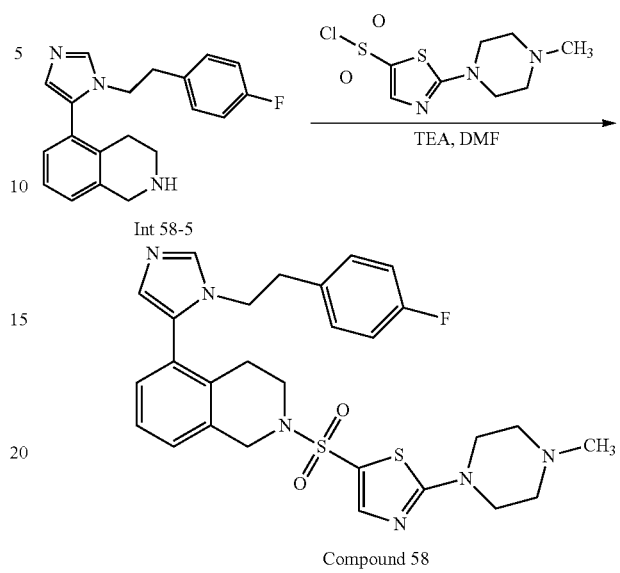

To a solution of Int 58-5 (76.3 mg, 0.237 mmol) and TEA (50.5 mg, 0.5 mmol) in DMF (4 mL) was added 2-(4-methylpiperazin-1-yl)thiazole-5-sulfonyl chloride (66 mg, 0.237 mmol) at 0° C. The reaction mixture was stirred at room temperature for 2 h then concentrated. The reaction mixture was purified by HPLC to give Compound 58 (80 mg). $^1$H NMR (CD₃OD): 7.63 (t, J=0.8 Hz, 2H), 7.21-7.27 (m, 2H), 6.80-6.95 (m, 6H), 4.35 (s, 2H), 4.00 (t, J=6.8 Hz, 2H), 3.53 (t, J=5.2 Hz, 4H), 3.29-3.32 (m, 2H), 2.77 (t, J=6.4 Hz, 2H), 2.50-2.55 (m, 6H), 2.31 (s, 3H). MS (ESI): m/z (M+H)⁺ 567.

Example 59

5-(1-(4-fluorophenethyl)-1H-imidazol-5-yl)-2-((6-(4-methylpiperazin-1-yl)pyridin-3-yl)sulfonyl)-1,2,3,4-tetrahydroisoquinoline (Compound 59)

Step A—Preparation of Int 59-1

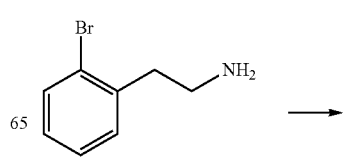

-continued

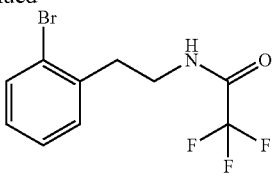

Int 59-1

To a stirred solution of 2-bromophenethylamine (20 g, 0.1 mol) in dichloromethane (200 mL) was added 2,6-lutidine (11.8 g, 0.11 mol) and 2,2,2-trifluoroacetic anhydride (23.1 g, 0.11 mol) at room temperature. The solution was stirred at room temperature for 3 hrs. The solution was washed with 1N hydrochloric acid. The organic layer were washed with brine, dried over anhydrous sodium sulfate then filtered. The filtrate was concentrated in vacuum to give the crude product Int 59-1 which was used directly without further purification. MS-ESI (m/z): 295 (M+H)$^+$.

Step B—Preparation of Int 59-2

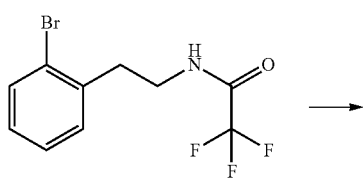

Int 59-1

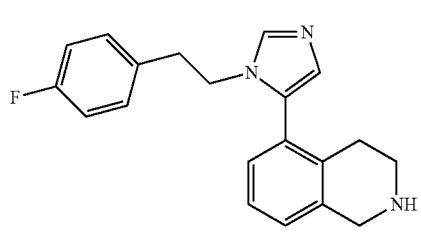

Int 59-2

To a stirred solution of compound Int 59-1 (2 g, 6.7 mmol) in acetic acid was added (CHO)$_n$ (406 mg, 13.6 mg) and conc H$_2$SO$_4$ (3.28 g, 33.5 mmol) at 0° C. The mixture was allowed to stir to room temperature overnight. The reaction mixture was poured into ice-water and the aqueous layer was extracted with ethyl acetate (3×10 mL). The combined organic layer was washed with brine, dried over anhydrous sodium sulfate then filtered. The filtrate was concentrated in vacuum to give the crude product compound Int 59-2 (1.1 g) as yellow oil which was used to next step directly without purification. MS-ESI (m/z): 309 (M+H)$^+$.

Step C—Preparation of Int 59-3

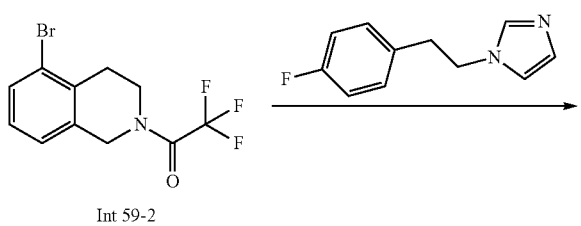

-continued

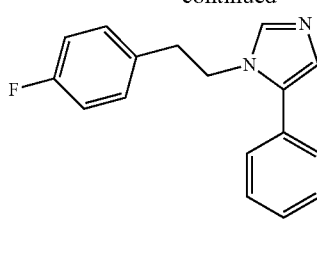

Int 59-3

To a solution of compound Int 59-2 (1.1 g, 5.8 mmol) in N,N-dimethylacetamide (10 mL) was added Int 3-1 (1.8 g, 5.8 mmol), P($^n$Bu)Ad$_2$(207 mg, 0.58 mmol), potassium carbonate (1.6 g, 116 mmol) and palladium acetate (150 mg, 0.58 mmol). The solution was stirred at 120° C. for 3 h. The mixture was cooled to room temperature and then filtered. The filtrate was concentrated and the residue was purified by HPLC to afford the product Int 59-3 (700 mg) as colorless oil. MS-ESI (m/z): 418 (M+H)$^+$.

Step D—Preparation of Int 59-4

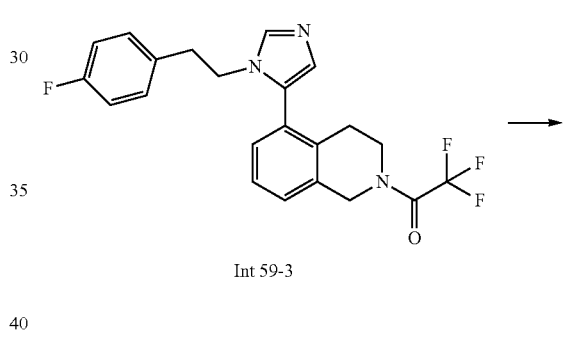

Int 59-3

Int 59-4

To a solution of compound Int 59-3 (500 mg, 1.2 mmol) in methanol (8 mL) was added potassium carbonate (496 mg, 3.6 mmol) at room temperature. The solution was stirred at 80° C. for 30 min. The mixture was cooled to room temperature and then filtered. The filtrate was concentrated and the residue was purified by HPLC to afford the product Int 59-4 (340 mg) as a colorless oil. MS-ESI (m/z): 322 (M+H)$^+$ Step E—Preparation of Int 11-5

Step F—Preparation of Compound 59

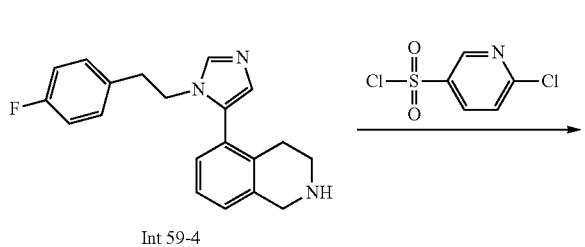
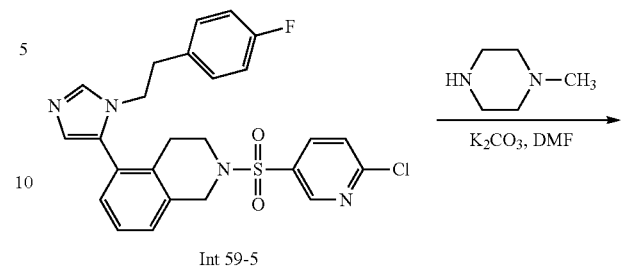

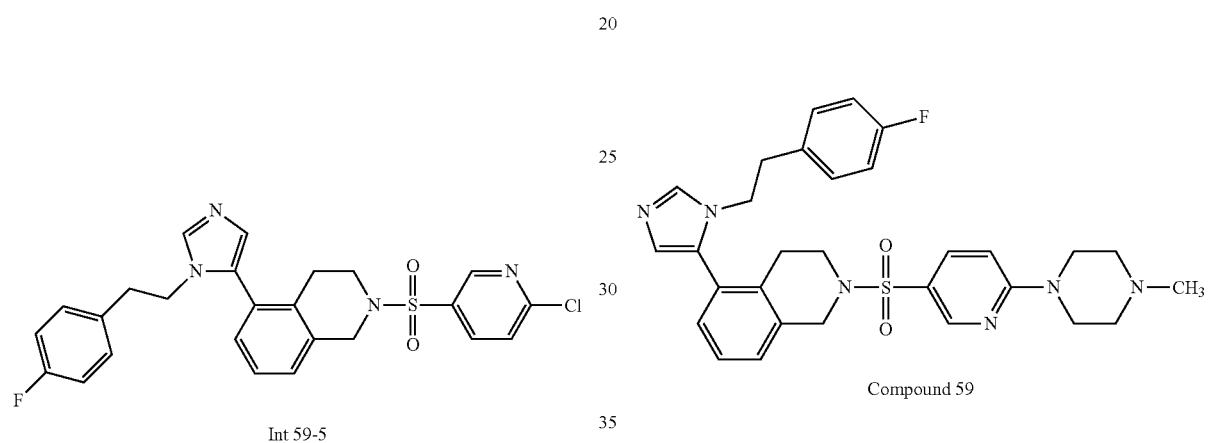

To a solution of compound Int 59-4 (300 mg, 9.3 mmol) in dichloromethane (5 mL) was added triethylamine (280 mg, 0.28 mmol) and 2-chloropyridine-5-sulfonylchloride (218 mg, 0.10 mmol). The mixture was stirred at room temperature for 30 mins. The suspension was filtered and the filtrate was concentrated and the residue was purified by HPLC to afford the product Int 59-5 (300 mg) as colorless oil. MS-ESI (m/z): 497 (M+H)$^+$ A solution of Int 59-5 (90 mg, 0.18 mmol), N-methyl piperazine (54 mg, 0.54 mmol) and K$_2$CO$_3$ (90 mg, 0.7 mmol) in DMF (5 mL) was heated to 130° C. for 2 h. The reaction mixture was filtered and purified by HPLC to give Compound 59 (200 mg). $^1$H NMR (CD$_3$OD): δ 8.44 (d, J=2.4 Hz, 1H), 7.79 (q, J=1.6 Hz, 1H), 7.61 (s, 1H), 7.20 (d, J=6.4 Hz, 2H), 6.79-6.88 (m, 6H), 6.74 (s, 1H), 4.28 (s, 2H), 3.94 (t, J=6.8 Hz, 2H), 3.68 (t, J=4.8 Hz, 4H), 3.22-3.29 (m, 2H), 2.73 (t, J=6.8 Hz, 2H), 2.44-2.50 (m, 6H), 2.30 (s, 3H).

The following compounds 60-62 can be prepared using a method similar to that described in Example 59 above.

| Cmpd | Structure | IUPAC name | M + 1 | $^1$H NMR |
|---|---|---|---|---|
| 60 | 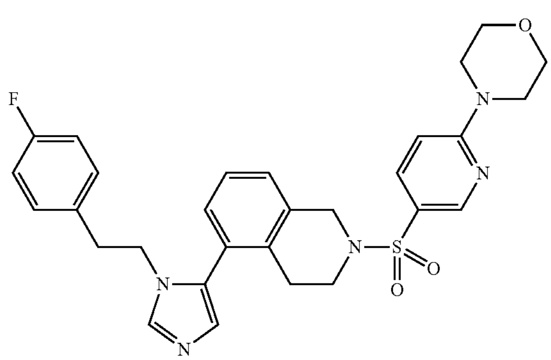 [SMILES: O=S(=O)(c1ccc(N2CCOCC2)nc1)N1CCc2c(cccc2-c2cncn2CCc2ccc(F)cc2)C1] | 4-(5-((5-(1-(4-fluorophenethyl)-1H-imidazol-5-yl)-3,4-dihydroisoquinolin-2(1H)-yl)sulfonyl)pyridin-2-yl)morpholine | 548.2 | CDCl$_3$: δ: 8.60 (d, J = 2.4 Hz, 1H), 7.79 (dd, J$_1$ = 2.4 Hz, J$_2$ = 2.4 Hz, 1H), 7.41 (s, 1H), 7.18 (t, J = 7.6 Hz, 1H), 7.09 (d, J = 7.2 Hz, 1H), 6.89-6.84 (m, 4H), 6.78-6.75 (m, 2H), 6.59 (d, J = 8.8 Hz, 1H), 4.27 (s, 2H), 3.86 (t, J = 7.2 Hz, 2H), 3.78-3.76 (m, 4H), 3.63-3.61 (m, 4H), 3.21 (t, J = 6 Hz, 2H), 2.72 (t, J = 7.2 Hz, 2H), 2.57 (t, J = 5.6 Hz, 2H). |

| Cmpd | Structure | IUPAC name | M + 1 | ¹H NMR |
|---|---|---|---|---|
| 61 | 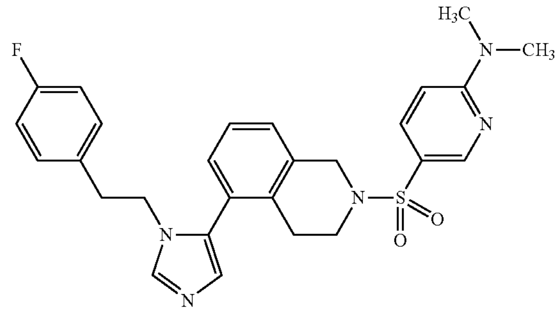 [SMILES: CN(C)c1ccc(S(=O)(=O)N2CCc3c(cccc3-c3cncn3CCc3ccc(F)cc3)C2)cn1] | 5-((5-(1-(4-fluorophenethyl)-1H-imidazol-5-yl)-3,4-dihydroisoquinolin-2(1H)-yl)sulfonyl)-N,N-dimethyl-pyridin-2-amine | 506.2 | CDCl₃: δ: 8.55 (d, J = 1.6 Hz, 1H), 7.74 (dd, J1 = 2.4 Hz, J1 = 2.8 Hz, 1H), 7.40 (s, 1H), 7.18 (t, J = 7.6 Hz, 1H), 7.09 (d, J = 7.2 Hz, 1H), 6.88-6.84 (m, 4H), 6.78-6.76 (m, 2H), 6..47 (d, J = 9.2 Hz, 1H), 4.26 (s, 2H), 3.86 (t, J = 6.8 Hz, 2H), 3.21 (t, J = 6.0 Hz, 2H), 3.13 (s, 6H), 2.71 (t, J = 6.8 Hz, 2H), 2.57 (t, J = 5.6 Hz, 2H). |
| 62 | 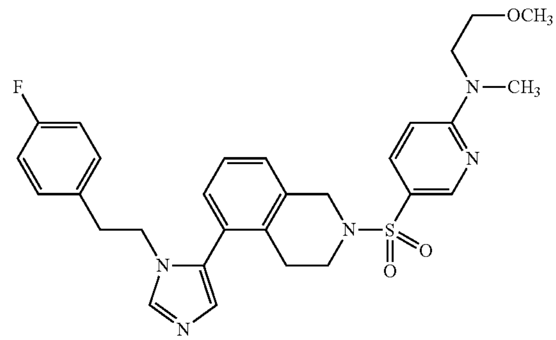 [SMILES: COCCN(C)c1ccc(S(=O)(=O)N2CCc3c(cccc3-c3cncn3CCc3ccc(F)cc3)C2)cn1] | 5-((5-(1-(4-fluorophenethyl)-1H-imidazol-5-yl)-3,4-dihydroisoquinolin-2(1H)-yl)sulfonyl)-N-(2-methoxy-ethyl)-N-methylpyridin-2-amine | 550.2 | CDCl₃: δ: 8.52 (d, J = 2.8 Hz, 1H), 7.72 (dd, J1 = 2.4 Hz, J2 = 2.4 Hz, 1H), 7.41 (s, 1H), 7.42 (s, 1H), 7.18 (t, J = 7.6 Hz, 1H), 7.10 (d, J = 7.6 Hz, 1H), 6.88-6.85 (m, 4H), 6.78-6.75 (m, 2H), 6.50 (d, J = 9.2 Hz, 2H), 4.26 (s, 2H), 3.86 (t, J = 7.2 Hz, 2H), 3.77 (t, J = 5.2 Hz, 2H), 3.55 (t, J = 5.6 Hz, 2H), 3.31 (s, 2H), 3.21 (t, J = 5.6 Hz, 2H), 3.11 (s, 3H), 2.72 (t, J = 6.8 Hz, 2H), 2.57 (t, J = 6.0 Hz, 2H). |

Example 63

(7R,8aS)-2-(5-((5-(1-((R)-1-(4-fluorophenyl)ethyl)-1H-imidazol-5-yl)-3,4-dihydroisoquinolin-2(1H)-yl)sulfonyl)thiazol-2-yl)octahydropyrrolo[1,2-a]pyrazin-7-ol (Compound 63)

Step A—Preparation of Int 63-1

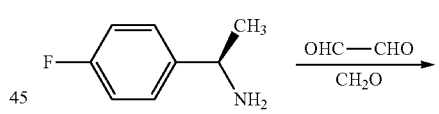

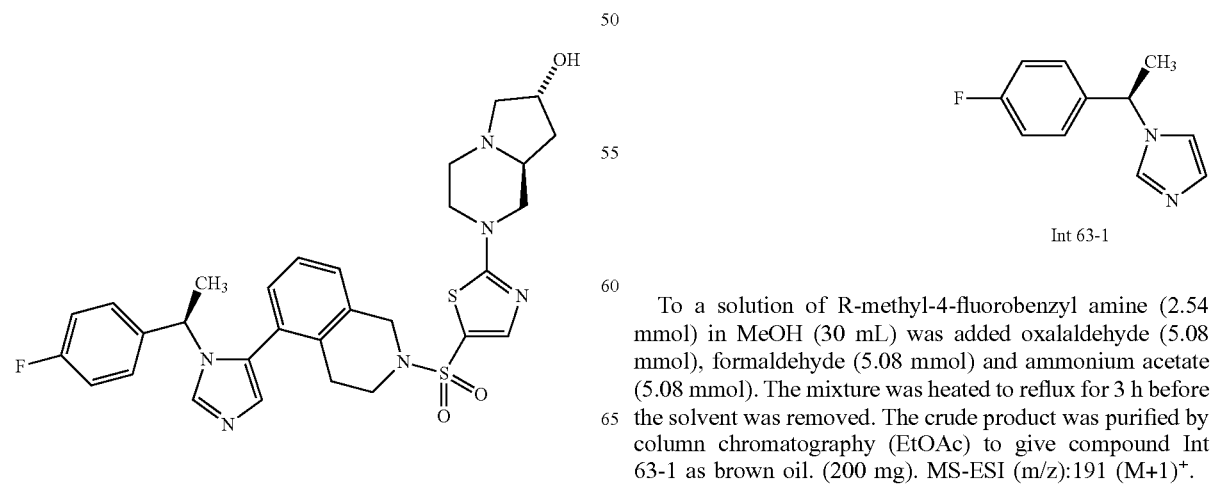

To a solution of R-methyl-4-fluorobenzyl amine (2.54 mmol) in MeOH (30 mL) was added oxalaldehyde (5.08 mmol), formaldehyde (5.08 mmol) and ammonium acetate (5.08 mmol). The mixture was heated to reflux for 3 h before the solvent was removed. The crude product was purified by column chromatography (EtOAc) to give compound Int 63-1 as brown oil. (200 mg). MS-ESI (m/z):191 (M+1)⁺.

Step B—Preparation of Int 63-2

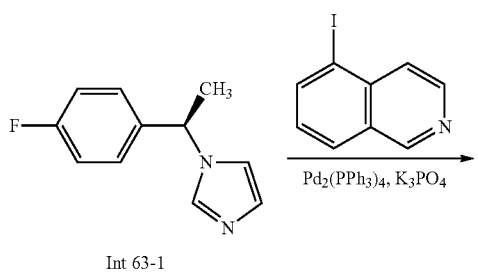

Step D—Preparation of Int 63-4

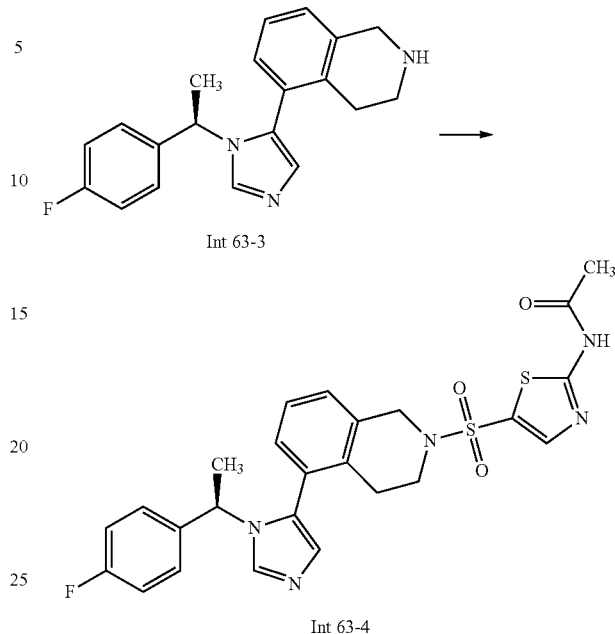

To a solution of 5-iodoisoquinoline (670 mg, 2.6 mmol) and compound Int 63-1 (500 mg, 2.6 mmol) in CH$_3$CN (20 mL) was added Pd$_2$(PPh$_3$)$_4$ (50 mg) and K$_3$PO$_4$ (100 mg). The mixture was stirred at 90° C. for 3 h under N$_2$ atmosphere. Water was added and the mixture was extracted with EtAOc. The organic extract was dried and evaporated to give crude product Int 63-2 which was purified by HPLC. (250 mg). MS-ESI (m/z): 318 (M+1)$^+$.

Step C—Preparation of Int 63-3

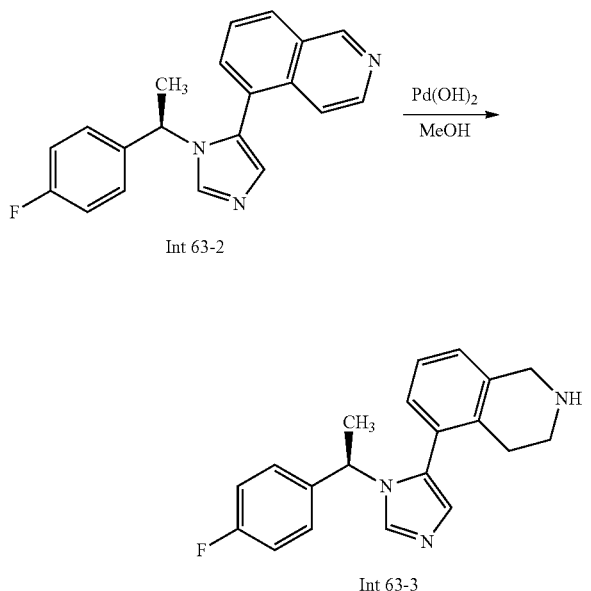

To a solution of compound Int 63-2 (250 mg, 0.79 mmol) in MeOH (50 mL) was added Pd(OH)$_2$/C (50 mg). The mixture was charged with H$_2$ (50 psi) and then stirred at 40° C. for 16 h. The result mixture was filtered and the filtrate was concentrated to dryness to give the crude product which was used in next step directly. MS-ESI (m/z): 322 (M+H)$^-$.

To a solution of compound Int 63-3 (60 mg, 0.17 mmol) in DMF (5 mL) was added Et$_3$N (0.5 mL) and 2-acetamidothiazole-5-sulfonyl chloride (48 mg, 0.2 mmol). The mixture was stirred for 10 mins at ambient temperature. The mixture was then filtered and evaporated to dryness. The crude product was purified by silica gel chromatography eluting with EtOAc:MeOH (5:1) to afford compound Int 63-4 (80 mg) as white solid. MS-ESI (m/z): 526 (M+H)$^+$.

Step E—Preparation of Int 63-5

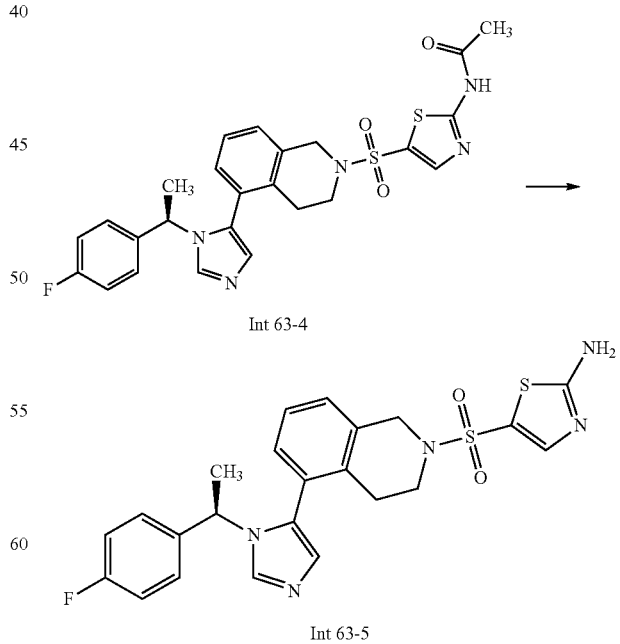

To a solution of compound Int 63-4 (80 mg, 0.15 mmol) in MeOH:H$_2$O (2:1) was added HCl (5 mL) and the mixture was stirred at reflux for 5 h. The solvent was removed and the crude product was purified by HPLC to afford compound Int 63-5 (20 mg). $^1$H-NMR (CD$_3$OD) δ 8.09 (s, 1H), 7.39 (s, 1H), 7.06 (d, J=8.0 Hz, 1H), 6.98 (s, 1H), 6.92-6.83 (m, 6H), 5.37 (q, J=7.6 Hz, 1H), 4.13 (q, J=16 Hz, 2H), 3.30 (t, J=5.6 Hz, 2H), 2.86 (t, J=5.6 Hz, 2H), 1.74 (d, J=7.2 Hz, 3H). MS-ESI (m/z): 484 (M+H)$^-$.

Step F—Preparation of Int 63-6

To a solution of compound Int 63-6 (80 mg, 0.15 mmol) in CH$_3$CN (5 mL) was added (7S,8R)-octahydropyrrolo[1,2-a]pyrazin-7-ol (42 mg, 0.3 mmol) and K$_2$CO$_3$ (104 mg, 0.75 mmol) and the mixture was stirred at 90° C. for 3 h. Water was added and mixture was extracted with EtOAc, dried and concentrated. The crude product was purified by HPLC to give Compound 63 (30 mg). $^1$H NMR: (CD$_3$OD): δ 8.11 (s, 1H), 7.61 (s, 1H), 7.22-7.18 (m, 2H), 6.88-6.86 (m,

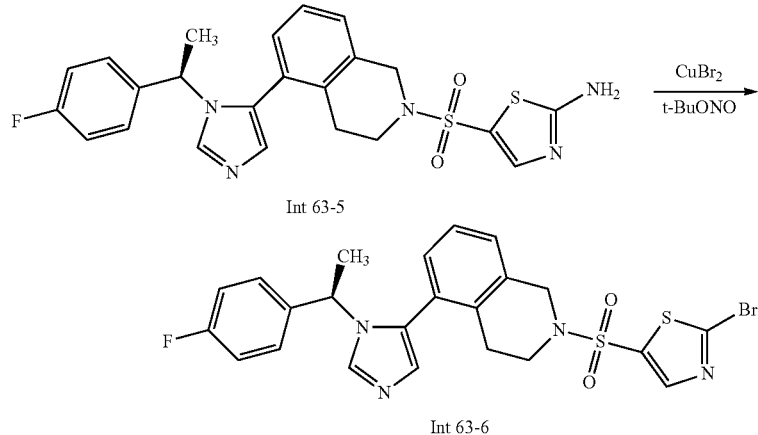

To a stirred mixture of CuBr$_2$ (93 mg, 0.42 mmol) in DMF (5 mL) was added tert-butyl nitrite (43 mg, 0.42 mmol) in drops at 0° C. A solution of Int 63-5 (100 mg, 0.21 mmol) (dissolved in DMF) was then added in drops at 0° C. and the reaction was stirred for another 20 mins. The mixture was warmed to 50° C. and stirred for 1 hour. The reaction was cooled and ammonium hydroxide was added to the stirred mixture and the solids were filtered. The solvent was removed and the residue (crude product) was purified by preparative TLC to afford compound Int 63-6 as a white solid. (80 mg). MS-ESI (m/z): 547, 549 (M+H)$^+$.

Step G—Preparation of Compound 63

4H), 6.80 (s, 2H), 5.06 (s, 1H), 4.42-4.38 (m, 2H), 4.06 (d, J=12.4 Hz, 2H), 3.92 (d, J=12.4 Hz, 1H), 3.45 (t, J=9.6 Hz, 1H), 3.37 (s, 1H), 3.21 (t, J=12 Hz, 1H), 3.05 (d, J=11.6 Hz, 1H), 2.85 (t, J=10.8 Hz, 1H), 2.59-2.35 (m, 4H), 2.15 (q, J=5.2 Hz, 1H), 1.82-1.76 (m, 6H). MS-ESI (m/z): 547 (M+H)$^+$.

The following compound 64 was prepared using a protocol similar to that described in Example 63 above.

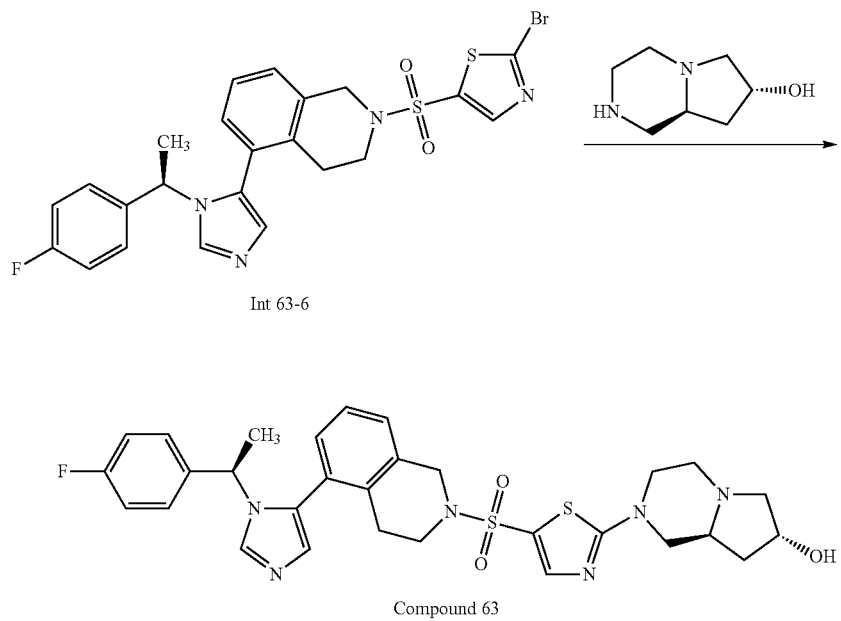 [SMILES: C[C@H](c1ccc(F)cc1)n1cncc1-c1cccc2c1CCN(S(=O)(=O)c1cnc(Br)s1)C2 ; O[C@@H]1C[C@H]2CNCCN2C1 ; C[C@H](c1ccc(F)cc1)n1cncc1-c1cccc2c1CCN(S(=O)(=O)c1cnc(N3CCN4C[C@H](O)C[C@H]4C3)s1)C2]

| Cmpd | Structure | IUPAC name | M + 1 | ¹H NMR |
|---|---|---|---|---|
| 64 | 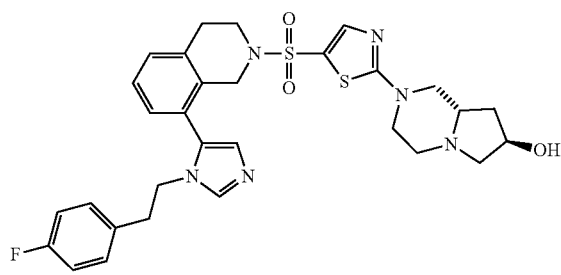 [SMILES: O=S(=O)(c1cnc(N2CCN3C[C@H](O)C[C@H]3C2)s1)N1CCc2cccc(-c3cncn3CCc3ccc(F)cc3)c2C1] | (7R,8aS)-2-(5-((5-(1-(4-fluorophenethyl)-1H-imidazol-5-yl)-3,4-dihydroisoquinolin-2(1H)-yl)sulfonyl)thiazol-2-yl)octahydropyrrolo[1,2-a]pyrazin-7-ol | 609 | (CD₃OD): δ 7.62 (s, 1H), 7.21-7.26 (m, 2H), 6.79-6.94 (m, 6H), 4.37 (d, J = 11.6 Hz, 3H), 3.88-4.03 (m, 4H), 3.44 (q, J = 6.8 Hz, 1H), 3.31 (d, J = 6.0 Hz, 1H), 3.20 (q, J = 3.2 Hz, 1H), 3.03 (d, J = 11.6 Hz, 1H), 2.75-2.84 (m, 3H), 2.53 (t, J = 5.6 Hz, 2H), 2.34-2.42 (m, 2H), 2.11 (q, J = 5.2 Hz, 1H), 1.72-1.76 (m, 2H). |

Example 65

(7R,8aS)-2-(5-((8-(1-(4-fluorophenethyl)-1H-imidazol-5-yl)-3,4-dihydroisoquinolin-2(1H)-yl)sulfonyl)thiazol-2-yl)octahydropyrrolo[1,2-a]pyrazin-7-ol (Compound 65)

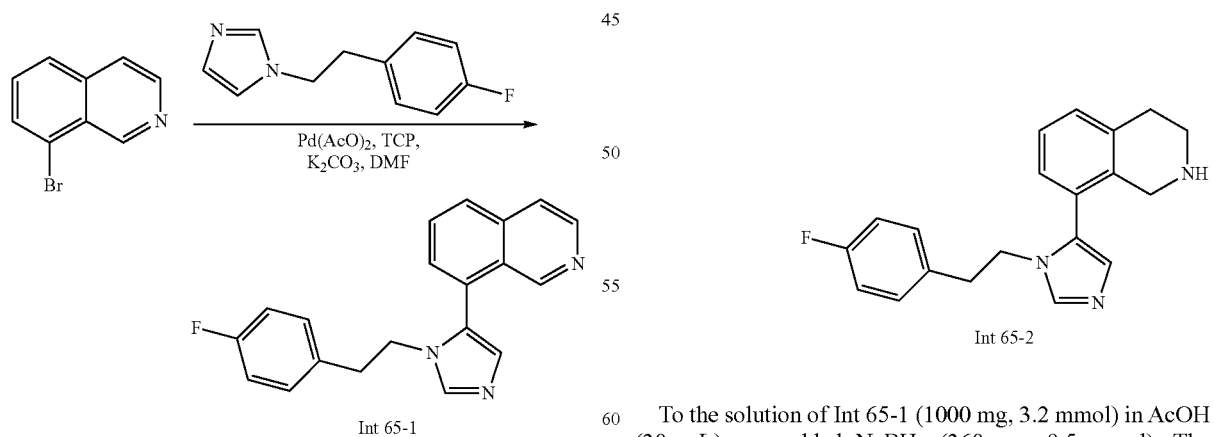

Step A—Preparation of Int 65-1

To a solution of Int 3-1 (219 mg, 1.15 mmol) and 3-bromoisoquinoline (200 mg, 0.96 mmol) in DMF (5 mL) was added potassium carbonate (391 mg, 2.88 mmol), TCP (53 mg, 0.19 mmol) and Pd(OAc)₂ (21 mg, 0.10 mmol). The mixture was stirred at 130° C. for 14 hours. The mixture was cooled and poured into H₂O (10 mL) and extracted with EtOAc (10 mL×3), the combined organic layer was washed with brine (10 mL), dried over sodium sulfate and concentrated. The crude mixture was and purified by TLC to give Int 65-1 (100 mg). ¹H NMR (CDCl₃): δ 9.05 (s, 1H), 8.57 (d, J=6.4 Hz, 1H), 7.87 (d, J=8.0 Hz, 1H), 7.66-7.70 (m, 2H), 7.53 (s, 1H), 7.31 (d, J=6.8 Hz, 1H), 6.93-6.95 (m, 1H), 6.77-6.81 (m, 2H), 6.66-6.69 (m, 2H), 4.00 (t, J=7.2 Hz, 2H), 2.68 (t, J=7.2 Hz, 2H). MS (ESI): m/z (M+H)⁺ 318.

Step B—Preparation of Int 65-2

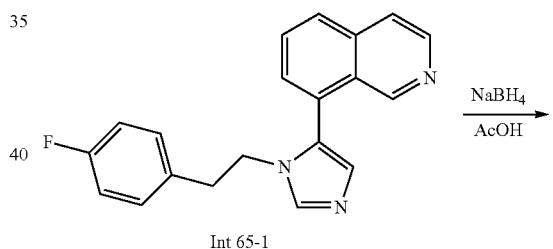

To the solution of Int 65-1 (1000 mg, 3.2 mmol) in AcOH (30 mL) was added NaBH₄ (360 mg, 9.5 mmol). The mixture was stirred at 0° C. for 20 mins. The mixture was poured into H₂O (100 mL) and extracted with EtOAc (50 mL×3) and the combined organic layer were washed with brine (100 mL), dried over sodium sulfate and concentrated. The crude mixture was and purified by TLC to give Int 65-2 (500 mg). MS (ESI): m/z (M+H)⁺ 322.

Step C—Preparation of Int 65-3

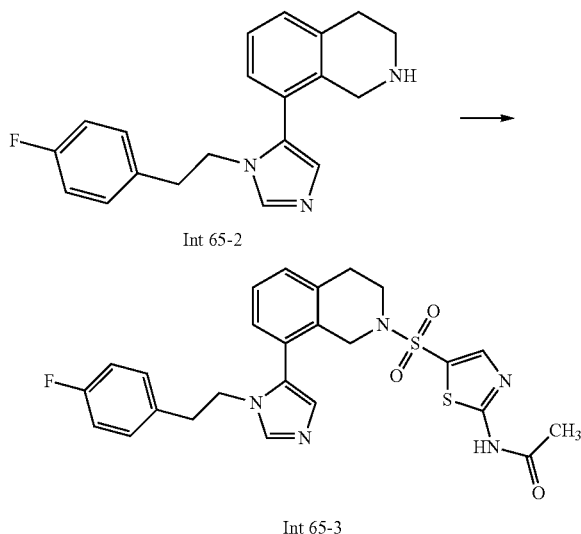

To a solution of Int 65-2 (500 mg, 1.4 mmol) and Et₃N (810 mg, 8.0 mmol) in DMF (30 mL) at 0° C. was added 2-acetamidothiazole-5-sulfonyl chloride (770 mg, 3.2 mmol) and the mixture was stirred at 0° C. for 30 mins, filtered and the filtrate was purified by HPLC to give Int 65-3. $^1$H NMR (CD$_3$OD): δ 7.78 (s, 1H), 7.61 (s, 1H), 7.24-7.25 (m, 2H), 6.86-6.94 (m, 6H), 4.03-4.06 (m, 4H), 3.43-3.46 (m, 2H), 3.02-3.03 (m, 2H), 2.71-2.75 (m, 2H), 2.17 (s, 3H). MS (ESI): m/z (M+H)$^+$ 526.

Step D—Preparation of Int 65-4

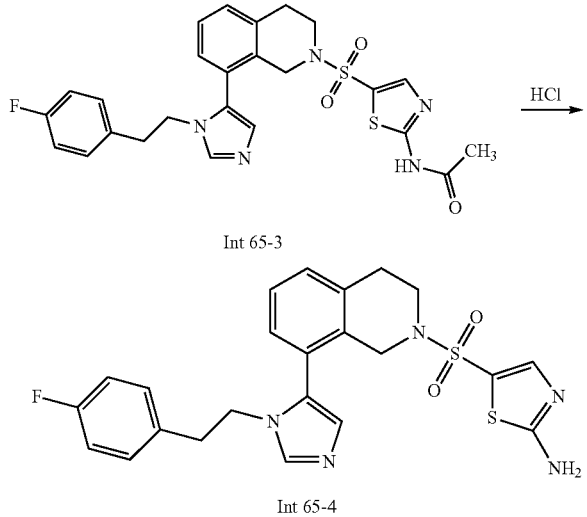

To a solution of Int 65-3 (600 mg, 0.46 mmol) in 4M HCl/MeOH (20 mL) was stirred at 60° C. for 3 h. The reaction mixture was concentrated and diluted with saturated NaHCO$_3$ (20 mL), extracted with DCM (20 mL×3). The combined organic extracts were washed with brine (20 mL), dried over sodium sulfate and concentrated to give crude Int 65-4 (320 mg). MS (ESI): m/z (M+H)$^+$ 484.

Step E—Preparation of Int 65-5

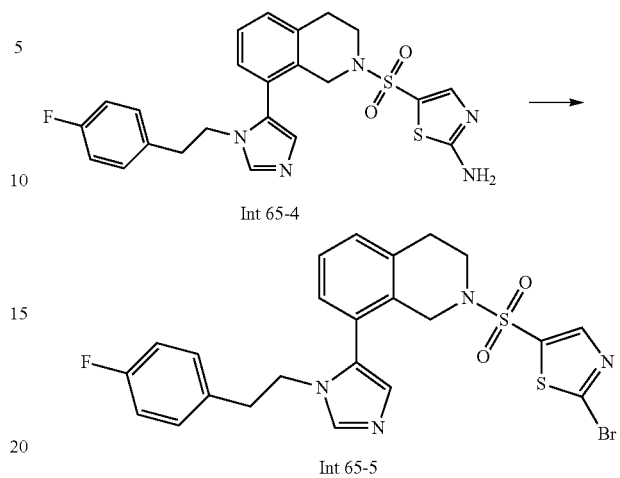

To the solution of CuBr$_2$ (294 mg, 1.32 mmol) in DMF (3 mL) was added n-BuONO$_2$ (136 mg, 1.32 mmol) and Int 65-4 (320 mg, 0.66 mmol). The mixture was stirred at 50° C. for 3 h. The mixture was poured into H$_2$O (10 mL) and extracted with EtOAc (10 mL×3). The combined organic extracts were washed with brine (10 mL), dried over sodium sulfate and concentrated. The crude mixture was and purified by HPLC to give Int 65-5 (250 mg). MS (ESI): m/z (M+H)$^+$ 547.

Step F—Preparation of Int 65-6

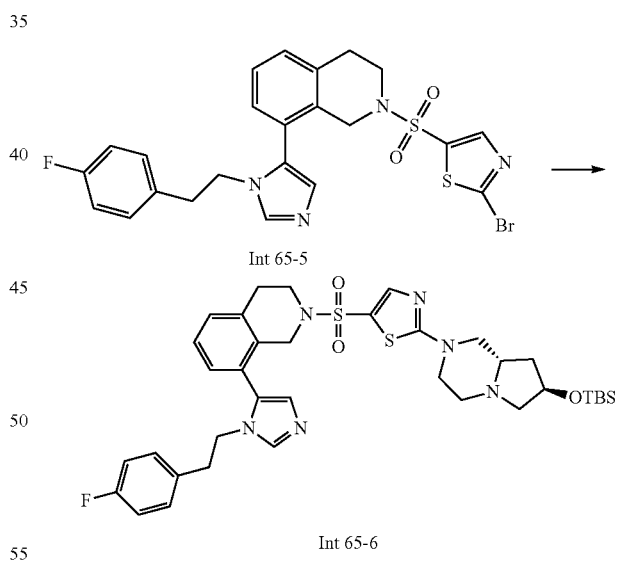

To a solution of Int 65-5 (250 mg, 0.46 mmol) in DMF (5 mL) was added K$_2$CO$_3$ (190 mg, 1.38 mmol) and (7R,8aS)-7-((tert-butyldimethylsilyl)oxy)octahydropyrrolo[1,2-a]pyrazine (81 mg, 0.46 mmol). The mixture was stirred at 120° C. for 12 h then cooled and filtered. The filtrate was poured into H$_2$O (10 mL) and extracted with EtOAc (10 mL×3). The combined organic extracts were washed with brine (10 mL), dried over sodium sulfate and concentrated. The crude mixture was and purified by HPLC to give Int 65-6 (220 mg). MS (ESI): m/z (M+H)$^+$ 723.

Step G—Preparation of Compound 65

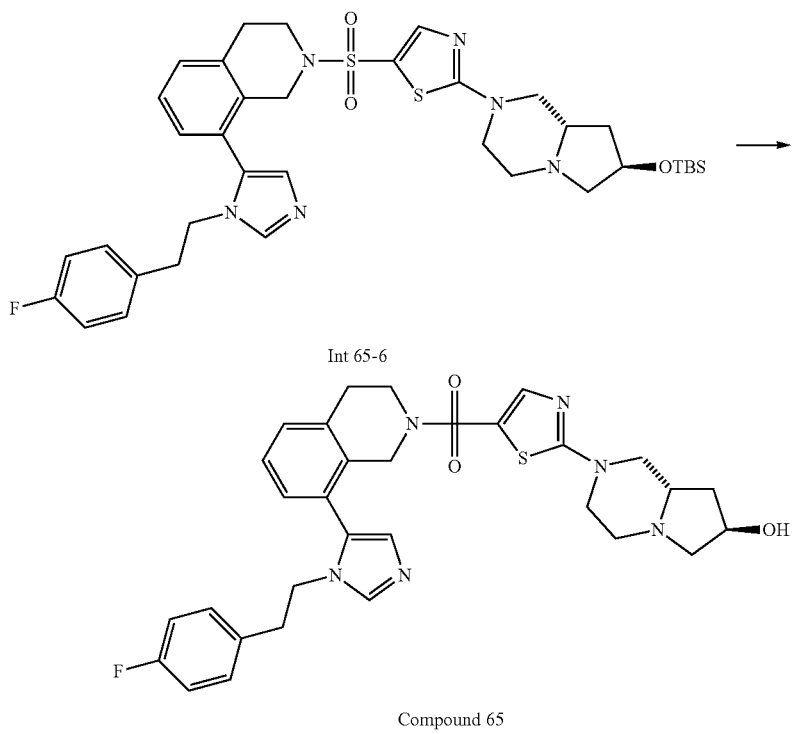

Int 65-6

Compound 65

To a solution of Int 65-6 (200 mg, 0.28 mmol) in THF (5 mL) was added TBAF (358 mg, 1.38 mmol) at room temperature. The mixture was stirred at room temperature for 1 hour, filtered and the filtrate was purified by HPLC to give Compound 65 (78 mg). $^1$H NMR (CD$_3$OD): δ 8.33 (s, 1H), 7.95 (s, 1H), 7.28-7.35 (m, 3H), 7.05-7.07 (m, 1H), 6.93-6.97 (m, 4H), 4.48-4.49 (m, 1H), 4.11-4.22 (m, 3H), 4.04 (s, 2H), 3.83-3.84 (m, 1H), 3.44-3.52 (m, 4H), 3.33-3.39 (m, 2H), 3.22-3.25 (m, 41H), 3.04-3.12 (m, 3H), 2.81-2.89 (m, 3H), 2.00-2.05 (m, 1H), 1.90-1.94 (m, 1H). MS (ESI): m/z (M+H)$^+$ 609.

Example 66

5-((4-(1-(4-fluorophenethyl)-1H-imidazol-5-yl)-5,6-dihydro-1,7-naphthyridin-7(8H)-yl)sulfonyl)-2-(4-methylpiperazin-1-yl)thiazole (Compound 66)

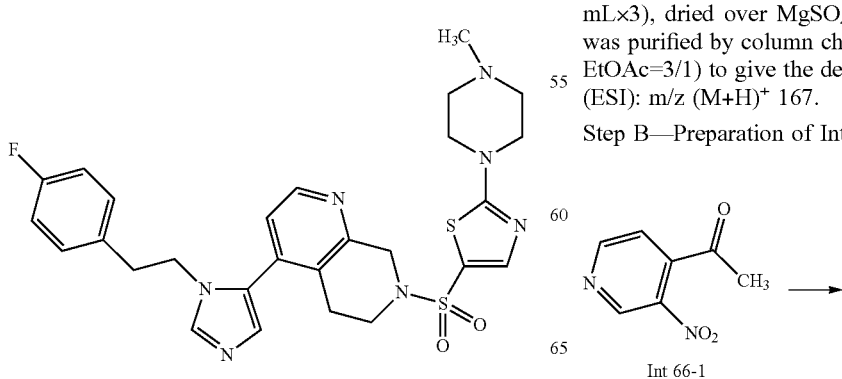

Step A—Preparation of Int 66-1

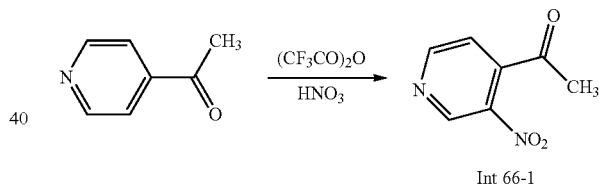

Int 66-1

A solution of 1-(pyridin-4-yl)ethanone (5.0 g, 41.3 mmol) in 24 mL of (CF$_3$CO)$_2$O was stirred at 0° C. for 2 h before 4.5 mL of HNO$_3$ was added dropwise. The mixture was stirred at room temperature overnight. The mixture was added to a cold solution of Na$_2$S$_2$O$_5$ (7.85 g, 41.3 mmol) in 25 mL of water. The mixture was then stirred at room temperature for 16 hours, extracted with EtOAc (150 mL×3), dried over MgSO$_4$ and concentrated. The residue was purified by column chromatography (Petroleum Ether/EtOAc=3/1) to give the desired product Int 66-1 (3 g). MS (ESI): m/z (M+H)$^+$ 167.

Step B—Preparation of Int 14-2

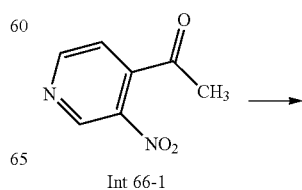

Int 66-1

-continued

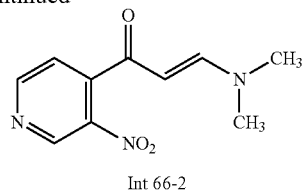

Int 66-2

To a solution of Int 66-1 (2.0 g, 12.0 mmol) in 20 mL of toluene was added dimethylformamide diethyl acetal (3.3 mL, 20 mmol). The mixture was stirred at 85° C. for 4 hours then cooled to room temperature and concentrated. The residue was purified by column chromatography (Petroleum Ether/EtOAc=1/1) to give the desired product Int 66-2 (1.5 g). MS (ESI): m/z (M+H)$^+$ 222.

Step C—Preparation of Int 66-3

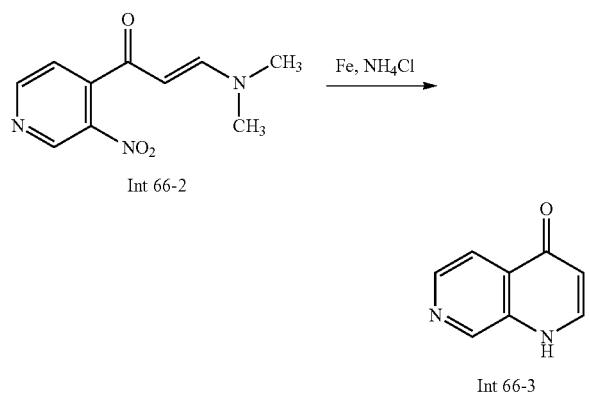

To a solution of Int 66-2 (2.0 g, 9.0 mmol) in EtOH/H$_2$O (30 mL/3 mL) was added Fe (powder) (2.02 g, 36 mmol) and NH$_4$Cl (1.9 g, 36 mmol). The mixture was stirred at 85° C. overnight. The solution was cooled to room temperature, filtered and concentrated. The residue was purified by column chromatography (MeOH/DCM=1/10) to give the desired product Int 66-3 (580 mg).

$^1$H NMR (Methanol-d$_4$): δ 8.98 (s, 1H), 8.46 (d, J=5.2 Hz, 1H), 8.05-8.09 (m, 2H), 6.39 (d, J=8.4 Hz, 1H). MS (ESI): m/z (M+H)$^+$ 147.

Step D—Preparation of Int 66-4

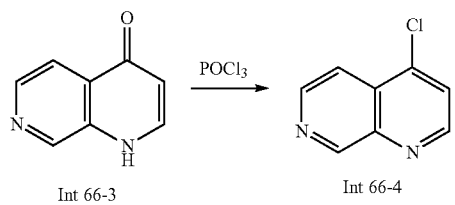

To a solution of Int 66-3 (500 mg, 2.37 mmol) in toluene (10 mL) was added POCl$_3$ (370 mg, 2.4 mmol) at room temperature. The mixture was stirred at 85° C. for 2 h then cooled to room temperature and concentrated to give the desired crude product Int 66-4 (500 mg). MS (ESI): m/z (M+H)$^+$ 165.

Step D—Preparation of Int 66-4

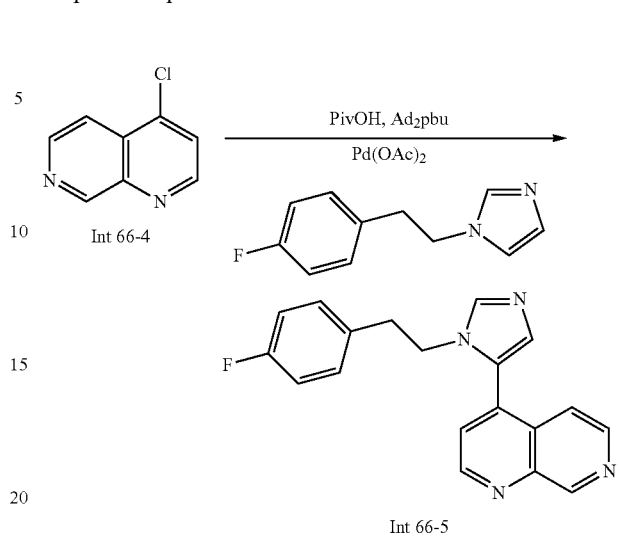

To a solution of compound Int 66-4 (350 mg, 2.13 mmol) and 1-(4-fluorophenethyl)-1H-imidazole (417 mg, 2.2 mmol) in DMA/H$_2$O (10 mL/0.5 mL) was added K$_2$CO$_3$ (580 mg, 4.2 mmol), PivOH (70 mg), Ad$_2$pbu (70 mg) and Pd(OAc)$_2$ (35 mg) at room temperature. The mixture was stirred at 130° C. overnight under N$_2$ then cooled to room temperature and diluted with 50 mL of water. The resulting mixture was extracted with EtOAc (50 mL×3) and the combined organic extracts were washed with brine (30 mL×3), dried with MgSO$_4$ and concentrated. The residue was purified by TLC (Petroleum Ether/EtOAc=1/1) to give Int 66-5 (350 mg, 51.7%). MS (ESI): m/z (M+H)$^+$ 319.

Step E—Preparation of Int 66-6

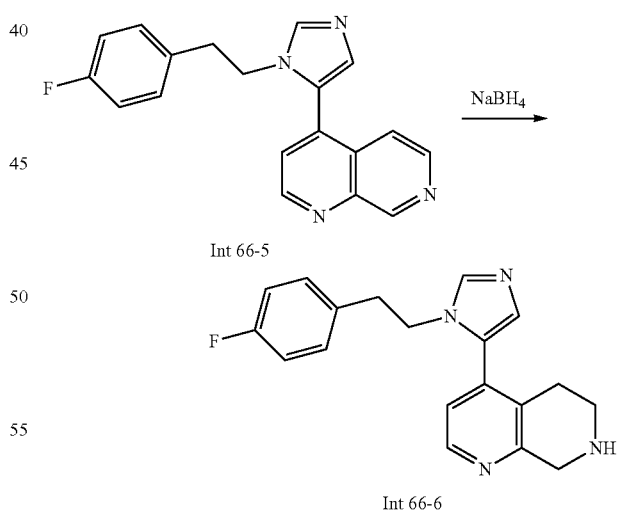

To a solution of compound Int 66-5 (180 mg, 0.57 mmol) in AcOH (10 mL) was added NaBH$_4$ (76 mg, 2 mmol) at 0° C. The mixture was stirred at 0° C. for 1 h then diluted with water (10 mL) and extracted with EtOAc (10 mL×3). The combined organic extracts were dried with MgSO$_4$ and concentrated to give Int 66-6 (100 mg). MS (ESI): m/z (M+H)$^+$ 323.

Step F—Preparation of Compound 66

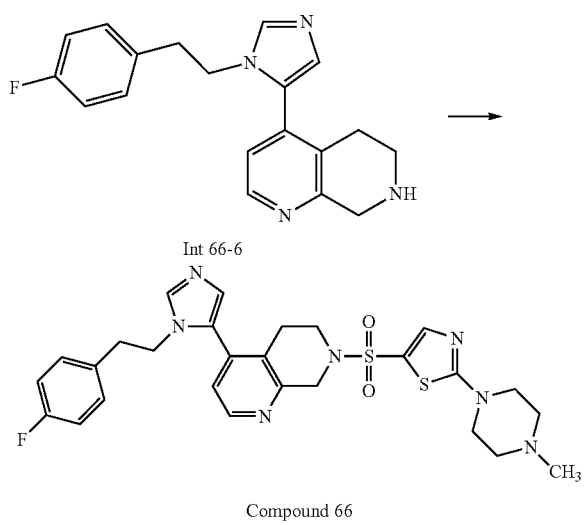

Int 66-6

Compound 66

To a solution of Int 66-6 (100 mg, 0.31 mmol) and TEA (101 mg, 1 mmol) in DMF (4 mL) was added 2-(4-methyl-piperazin-1-yl)-thiazole-5-sulfonyl chloride (200 mg, 0.69 mmol) at 0° C. The mixture was stirred for 20 mins then concentrated and purified by HPLC to give Compound 66 (4 mg). $^1$H NMR (CD$_3$OD): δ 8.37 (d, J=5.2 Hz, 1H), 7.77 (s, 1H), 7.66 (s, 1H), 7.00 (d, J=4.8 Hz, 1H), 6.95 (s, 1H), 6.82 (d, J=7.2 Hz, 4H), 4.35 (s, 2H), 4.18 (t, J=6.0 Hz, 2H), 3.54 (t, J=5.2 Hz, 4H), 3.32 (t, J=6.0 Hz, 2H), 2.80 (t, J=6.4 Hz, 2H), 2.61 (t, J=5.6 Hz, 2H), 2.51 (t, J=5.2 Hz, 4H), 2.30 (s, 3H). MS (ESI): m/z (M+H)$^+$ 568.

Example 67

5-((4-(1-(4-fluorophenethyl)-1H-imidazol-5-yl)-5,6-dihydropyrido[3,4-d]pyrimidin-7(8H)-yl)sulfonyl)-2-(4-methylpiperazin-1-yl)thiazole (Compound 67)

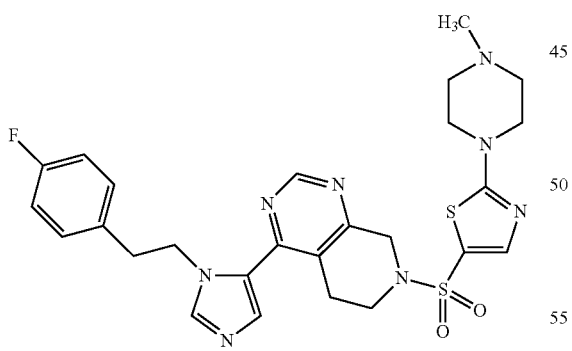

Step A—Preparation of Int 67-1

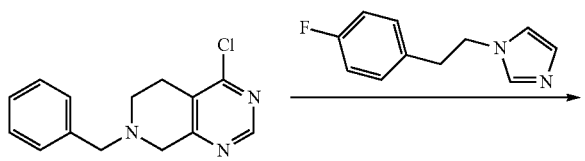

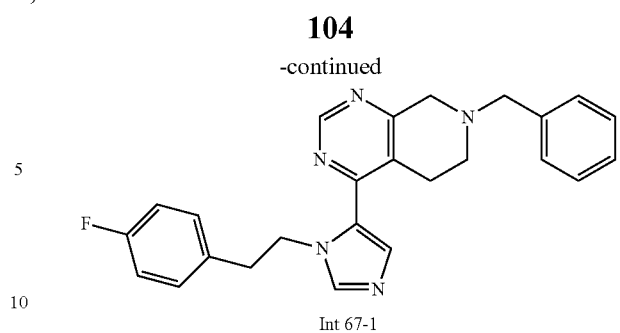

Int 67-1

To a solution of 4-chloro-5,6,7,8-tetrahydro-7-(phenylmethyl)pyrido[3,4-d]pyrimidine, [CAS No. 192869-80-0] (2 g, 7.7 mmol) in DMAc/H$_2$O (30 mL/2.7 mL) was added Int 3-1 (1.46 g, 7.7 mmol), potassium carbonate (3.7 g, 26.9 mmol), Ad$_2$PBu (826 mg, 2.3 mmol), PivOH (864 mg, 8.47 mmol) and Pd(OAc)$_2$ (172 mg, 0.77 mmol). The mixture was stirred at 130° C. overnight under a nitrogen atmosphere. The reaction mixture was cooled and water (15 mL) was added. The reaction mixture was extracted with EtOAc (50 mL×3) and the combined organic extracts were dried over sodium sulfate and concentrated. The crude mixture was purified by column chromatography (Petroleum Ether/EtOAc=1:2) to give Int 67-1. $^1$H NMR (CD$_3$OD): δ 8.86 (s, 1H), 7.79 (s, 1H), 6.73-7.10 (m, 8H), 4.21-4.25 (m, 2H), 4.05-4.11 (m, 2H), 3.01-3.06 (m, 2H), 2.87-2.90 (m, 2H), 2.74-2.77 (m, 4H). MS (ESI): m/z (M+H)$^+$ 414.

Step B—Preparation of Int 67-2

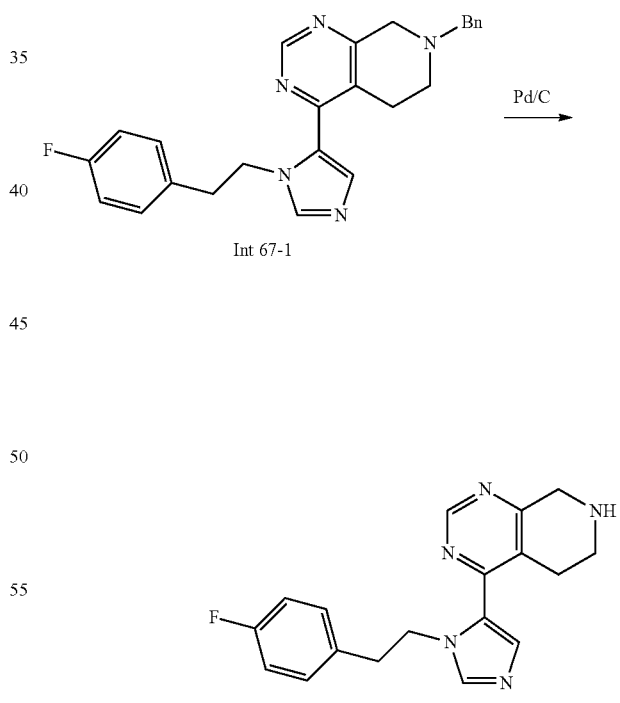

Int 67-1

Int 67-2

To a solution Int 67-1 (300 mg, 0.726 mmol) in 30 mL of MeOH was added Pd/C (30 mg). The reaction mixture was stirred under H$_2$ (40 psi) atmosphere at room temperature overnight. The mixture was filtered and concentrated to give the product Int 67-2 (200 mg). MS (ESI): m/z (M+H)$^+$ 324.

Step B—Preparation of Compound 67

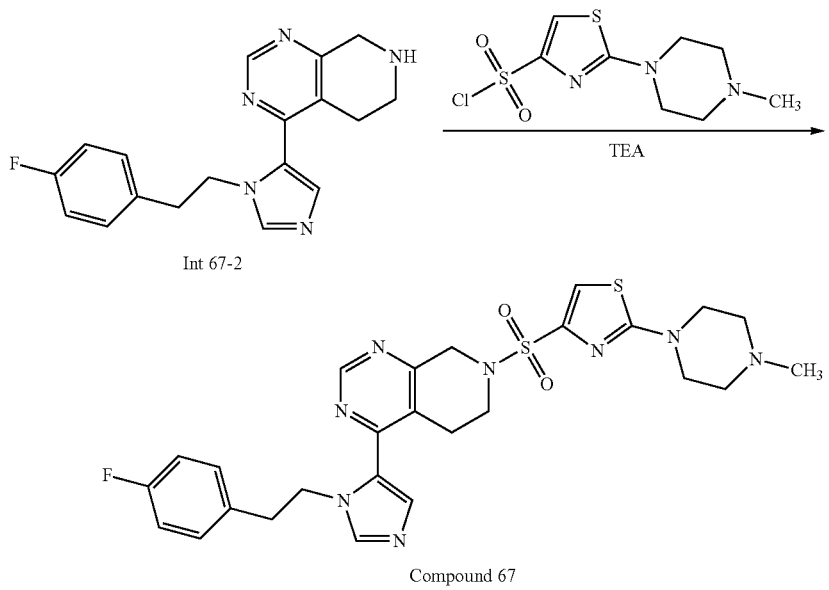

Int 67-2

Compound 67

To a solution of Int 67-2 (100 mg, 0.31 mmol) and TEA (101 mg, 1 mmol) in DMF (4 mL) was added 2-(4-methyl-piperazin-1-yl)-thiazole-5-sulfonyl chloride (200 mg, 0.69 mmol) at 0° C. The mixture was stirred for 20 mins then concentrated and purified by HPLC to give Compound 67. $^1$H NMR (CD$_3$OD): δ 8.92 (s, 1H), 7.84 (s, 1H), 7.71 (s, 1H), 7.38 (s, 1H), 6.79-6.82 (m, 2H), 6.68-6.72 (m, 2H), 4.80-4.83 (m, 2H), 4.26 (s, 2H), 3.61-3.62 (m, 4H), 3.34-3.37 (m, 2H), 22.83-2.89 (m, 4H), 2.64-2.66 (m, 4H), 2.39 (s, 3H). MS (ESI): m/z (M+H)$^+$ 569.

Example 68

Determination of IC$_{50}$ vs CYP3A by Measurement of Inhibition of Lopinavir Metabolism This assay was performed in a standard 96-well plate design. IC$_{50}$ values were calculated from the percent inhibition observed for each test compound at 6 concentrations (for example, 0.098, 0.391, 1.56, 6.25, 25 and 100 nM). The incubation substrate mix contains 1.5 µM lopinavir, 0.01 mg/mL protein human liver microsomes (BD Gentest), 1 mM NAPDH, 3.3 mM MgCl$_2$ and 100 mM potassium phosphate buffer (pH 7.4). The production of the sum of three hydroxylated metabolites (M2: 6-hydroxy lopinavir, M3: 4-hydroxy lopinavir, M4: 4-hydroxy lopinavir (epimer of M3), Kumar et al., 1999) was determined after incubation for 8 min at 37° C. Quantitation of the metabolite peak area ratio against an internal standard (tolbutamide) was determined by LC/MS/MS analysis following acetonitrile treatment of the incubations.

Samples were analyzed in the MRM mode with a SCIEX API-4000 mass spectrometer (Applied Biosystems, Foster City, Calif.), with a Shimadzu LC-20 AD pump (Shimadzu corporation, Kyoto, JP) and a CTC PAL autosampler (Agilent Technologies, Switzerland). A Phenomenex, Luna, 5 µm, 100 A, 2.00×30 mm HPLC column was used for the separation. The mobile phases were: (A) 0.1% formic acid in water and (B) 0.1% formic acid in acetonitrile. The binary gradient was as follows.

| AutoSampler: CTC PAL | |
|---|---|
| Loop Volume 1 (user entered) | 100 µL |
| Loop Volume 2 (user entered) | 100 µL |
| Actual Injection Volume | 10.0 µL |

| Binary Gradient | | |
|---|---|---|
| Total Flow: 700 µL/min | | |
| Time (min) | A (%) | B (%) |
| 0.01 | 95 | 5 |
| 0.50 | 2 | 98 |
| 0.70 | 2 | 98 |
| 0.71 | 95 | 5 |
| 1.00 | System Controller | Stop |

The mass spectrum parameters were as follows:

| MS Parameters: | |
|---|---|
| CUR Curtain gas (psi): | 20 |
| GS1 Ion source gas1(psi): | 55 |
| GS2 Ion source gas2(psi): | 60 |
| IS IonSpray voltage (V): | 5500 |
| TEM Temperature (° C.): | 600 |
| ihe Interface heater (on/off): | ON |
| CAD Collision Activated Dissociation (psi): | 10 |
| EP Entrance Potential (V): | 10 |
| CXP Collision Cell Exit Potential (V) | 12 |

The LC/MS/MS parameters for the analytes were as follows.

LC/MS/MS Analysis

| Compound | Ion Transition | | DP | CE | RT |
|---|---|---|---|---|---|
| | Q1 Mass (m/z) | Q3 Mass (m/z) | Declustering Potential (V) | Collission Energy (V) | Retention Time (min) |
| M2-4 | 645.2 | 447.2 | 30 | 25 | 0.51 |
| Lopinavir | 629.2 | 183.1 | 80 | 63 | 0.56 |
| IS (Tolbutamide) | 271.1 | 155.3 | 52 | 25 | 0.49 |

The peak area ratio of the analyte to the internal standard was used to quantify the metabolite. The values of peak area ratios in the presence of test compound were compared to those of maximum or minimum controls and were expressed as % inhibition by interpolating between the maximum and minimum peak area ratios. Incubations with no inhibitor were defined as the maxima and with 5 µM ketoconazole were defined as the minima.

The following equation was used to calculate the % inhibition:

$$[1-[(X-\text{Low control})/(\text{High control}-\text{Low control})]] *100$$

For the $IC_{50}$ calculation, SigmaPlot was used to plot the mean % inhibition versus the test compound concentrations and for non-linear regression analysis of the data. Depending on the range of data points defining the inhibition curve, the data may have been fit to the 4-parameter logistic equation.

Example 69

Determination of $IC_{50}$ in a Cocktail Assay for CYPs 1A2, 2C9, 2C19, 2D6 and 3A4:

This assay was performed in a standard 96-well plate design. $IC_{50}$ values were calculated from the percent inhibition observed for each test compound at 6 concentrations (for example, 0.0032, 0.016, 0.08, 0.4, 2 and 10 µM). The incubation substrate mix contains 10 µM phenacetin (1A2), 5 µM diclofenac (2C9), 30 µM mephenytoin (2C19), 5 µM dextromethorphan (2D6) and 2 µM midazolam (3A4), 0.1 mg/mL protein human liver microsomes (BD Gentest), 1 mM NAPDH, 3.3 mM $MgCl_2$ and 100 mM potassium phosphate buffer (pH 7.4). The production of the metabolite of each probe substrate was determined after incubation for 10 min at 37° C. Quantitation of the metabolite peak area ratio against an internal standard (tolbutamide) was determined by LC/MS/MS analysis following acetonitrile treatment of the incubations.

| Probe Substrate | Reaction (isoform) | Metabolite Detected |
|---|---|---|
| Phenacetin | O-deethylation (CYP1A2) | Acetaminophen |
| Diclofenac | 4'-hydroxylation (CYP2C9) | 4'-Hydroxydiclofenac |
| Mephenytoin | 4'-hydroxylation (CYP2C19) | 4'-Hydroxymephenytoin |
| Dextromethorphan | O-demethylation (CYP2D6) | Dextrorphan |
| Midazolam | 1'-hydroxylation (CYP3A4) | 1'-Hydroxymidazolam |

Samples were analyzed in the MRM mode with a SCIEX API-4000 mass spectrometer (Applied Biosystems, Foster City, Calif.), with a Shimadzu LC-20 AD pump (Shimadzu corporation, Kyoto, JP) and a CTC PAL autosampler (Agilent Technologies, Switzerland). A Phenomenex, Luna, 5 nm, 100 A, 2.00×30 mm HPLC column was used for the separation. The mobile phases were: (A) 0.1% formic acid in water and (B) 0.1% formic acid in acetonitrile. The binary gradient was as follows.

| AutoSampler: CTC PAL | |
|---|---|
| Loop Volume 1 (user entered) | 100 µL |
| Loop Volume 2 (user entered) | 100 µL |
| Actual Injection Volume | 10.0 µL |

Binary Gradient
Total Flow: 700 µL/min

| Time (min) | A (%) | B (%) |
|---|---|---|
| 0.01 | 98 | 2 |
| 0.40 | 30 | 70 |
| 0.80 | 2 | 98 |
| 1.00 | System Controller | Stop |

The mass spectrum parameters were as follows:

| MS Parameters: | |
|---|---|
| CUR Curtain gas (psi): | 20 |
| GS1 Ion source gas1(psi): | 50 |
| GS2 Ion source gas2(psi): | 60 |
| IS IonSpray voltage (V): | 5500 |
| TEM Temperature (° C.): | 600 |
| ihe Interface heater (on/off): | ON |
| CAD Collision Activated Dissociation (psi): | 10 |
| EP Entrance Potential (V): | 10 |
| CXP Collision Cell Exit Potential (V) | 12 |

The LC/MS/MS parameters for the analytes were as follows.

LC/MS/MS Analysis

| Compound | Ion Transition | | DP Declustering Potential (V) | CE Collission Energy (V) | RT Retention Time (min) |
|---|---|---|---|---|---|
| | Q1 Mass (m/z) | Q3 Mass (m/z) | | | |
| Acetaminophen | 152.2 | 110 | 40 | 23 | 0.36 |
| 4'-Hydroxy-diclofenac | 312 | 231 | 32 | 29 | 0.72 |
| 4'-Hydroxy-mephenytoin | 235.3 | 150.3 | 45 | 25 | 0.49 |
| Dextrorphan | 258.2 | 157.2 | 40 | 55 | 0.42 |
| 1'-hydroxy-midazolam | 342.2 | 203.2 | 40 | 30 | 0.53 |
| IS | 271.1 | 155.3 | 69 | 25 | 0.71 |

The peak area ratio of the analyte to the internal standard was used to quantify the metabolite. The values of peak area ratios in the presence of test compound were compared to those of maximum or minimum controls and were expressed as % inhibition by interpolating between the maximum and minimum peak area ratios. Incubations with no inhibitor were defined as the maxima.

The following equation was used to calculate the % inhibition:

$$[1-[(X-\text{Low control})/(\text{High control}-\text{Low control})]]*100$$

For the $IC_{50}$ calculation, SigmaPlot was used to plot the mean % inhibition versus the test compound concentrations and for non-linear regression analysis of the data. Depending on the range of data points defining the inhibition curve, the data may have been fit to the 4-parameter logistic equation.

Example 70

The table below provides data for compounds of Formula (I) obtained using the assays described in Examples 68 and 69, above.

| Cmpd | CYP $IC_{50}$ (nM) | | | | | |
|---|---|---|---|---|---|---|
| | 3A4 (LPV) | 3A4 (MDZ) | 1A2 | 2C9 | 2C19 | 2D6 |
| 1 | 2.3 | 11 | 1454 | 10 | 44 | 765 |
| 2 | 17 | 39 | 2612 | 505 | 121 | 288 |
| 3 | 14 | 22 | >10000 | 4300 | >10000 | 2530 |
| 4 | 9 | 12 | >10000 | 2200 | 6700 | 5110 |
| 5 | 80 | 65 | >10000 | >10000 | >10000 | >10000 |
| 6a | 8.6 | 7.5 | >10000 | 4550 | 8700 | 2540 |
| 6b | 40.3 | 30 | >10000 | 5450 | >10000 | 3500 |
| 7 | 10.6 | 22.9 | 6068 | 5994 | 3182 | 2876 |
| 8 | 1.9 | 4.4 | 8561 | 565 | 281 | 1197 |
| 9 | 2.4 | 9.0 | >10000 | 684 | 148 | 2099 |
| 10 | >100 | 192 | 8483 | >10000 | >10000 | 9202 |
| 11 | >100 | 197 | >10000 | 7473 | 912 | 8391 |
| 12 | 5.0 | 8.7 | 2401 | 49 | 300 | 675 |
| 13 | 5.3 | 5.9 | 99 | 65 | 357 | 348 |
| 14 | 54.0 | 137.0 | >10000 | 7408 | >10000 | 1097 |
| 15 | 8.0 | 6.4 | >10000 | 1227 | 155 | 1399 |
| 16 | 9.5 | 13.2 | 3102 | 486 | 1257 | 360 |
| 17 | 35.9 | 10.5 | >10000 | >10000 | >10000 | 5204 |
| 18 | 18.6 | 15.8 | >10000 | >10000 | 2935 | 7179 |
| 19 | 16.4 | 9.5 | >10000 | 6273 | >10000 | 3204 |
| 20 | 100 | 38.5 | >10000 | >10000 | >10000 | >10000 |
| 21 | 5.6 | 13.7 | 5889 | 4406 | 4191 | 4046 |
| 22a | 1.4 | 5.3 | 7025 | 6299 | >10000 | 3941 |
| 22b | 4.5 | 9.6 | >10000 | 1688 | >10000 | 4621 |
| 23a | 58.5 | 36.4 | >10000 | >10000 | 6916 | 6715 |
| 23b | 17.2 | 17.0 | >10000 | >10000 | >10000 | >10000 |
| 24 | 29.5 | 32.5 | >10000 | >10000 | >10000 | >10000 |
| 25 | 23.0 | 50.3 | 9492 | 2217 | 1895 | 2143 |
| 26 | 1.0 | 3.8 | 5024 | 1159 | 1362 | 1646 |
| 27 | 41.0 | 36.1 | 2649 | 1914 | 3796 | 3479 |
| 28a | 0.7 | 3.5 | >10000 | 1523 | 2389 | 6988 |
| 28b | 10.1 | 11.8 | >10000 | 1149 | 4976 | >10000 |
| 29 | 7.6 | 8.3 | 3820 | 1862 | 3259 | 2933 |
| 30 | 37.7 | 18.8 | >10000 | >10000 | >10000 | >10000 |
| 31 | 25.4 | 25.4 | >10000 | >10000 | >10000 | >10000 |
| 32 | 0.7 | 4.2 | >10000 | 3718 | 3411 | 5817 |
| 33 | 12.6 | 22.5 | >10000 | 2892 | >10000 | 6500 |
| 34a | 4.5 | 10.4 | 7016 | 2623 | 2685 | 1675 |
| 34b | 1.0 | 5.5 | >10000 | 1901 | 4398 | 2419 |
| 35a | 4.2 | 8.1 | >10000 | 8604 | >10000 | 4595 |
| 35b | 0.9 | 4.0 | >10000 | 6930 | 9717 | 3056 |
| 36 | 7.0 | 19.4 | 7692 | 1896 | 1683 | 3697 |
| 37 | 35.2 | 17.8 | >10000 | >10000 | 5807 | >10000 |
| 38 | 5.5 | 6.7 | 3351 | 1765 | 2299 | 6861 |
| 39a | 4.3 | 7.6 | 3839 | 2205 | 2734 | 9041 |
| 39b | 28.2 | 34.5 | >10000 | 6384 | 4738 | 8582 |
| 40 | 27.4 | 43.4 | >10000 | 4562 | >10000 | 3301 |
| 41 | 11.1 | 10.7 | >10000 | >10000 | >10000 | >10000 |
| 42a | 100 | 64.4 | >10000 | >10000 | >10000 | 1835 |
| 42b | 9.3 | 13.1 | >10000 | >10000 | >10000 | >10000 |
| 43a | 35.2 | 36.3 | >10000 | >10000 | 3270 | >10000 |
| 43b | 2.0 | 5.8 | 4489 | 7946 | >10000 | 5356 |
| 44a | 20.1 | 46.6 | >10000 | >10000 | 6521 | >10000 |
| 44b | 6.4 | 6.7 | >10000 | 5902 | 7126 | >10000 |
| 45a | nd | 14.3 | >10000 | >10000 | 7792 | 4224 |
| 45b | nd | 22.8 | >10000 | >10000 | >10000 | 2479 |
| 46a | 45.3 | 58.5 | >10000 | >10000 | >10000 | >10000 |
| 46b | 6.2 | 6.1 | >10000 | >10000 | >10000 | >10000 |
| 47 | 16.7 | 14.9 | 2079 | 2328 | 1008 | 2499 |
| 48a | 32.3 | 24.2 | 9300 | >10000 | 5427 | 6803 |
| 48b | >100 | 41.2 | >10000 | 9843 | 4805 | 3880 |
| 49a | 29.6 | 30.1 | >10000 | 9744 | 3830 | 4700 |
| 49b | >100 | 58.6 | >10000 | >10000 | 6910 | >10000 |
| 50 | 14.2 | 9.4 | 5753 | 4179 | 2069 | 10000 |
| 51 | 34.7 | 22.6 | 1161 | 4643 | 2111 | 6776 |

-continued

| | CYP IC$_{50}$ (nM) | | | | | |
|---|---|---|---|---|---|---|
| Cmpd | 3A4 (LPV) | 3A4 (MDZ) | 1A2 | 2C9 | 2C19 | 2D6 |
| 52 | 6.0 | 5.761 | 6501 | 1966 | 248.6 | 2458 |
| 53a | 2.0 | 8.649 | 1077 | 165.4 | 78.6 | 1371 |
| 53b | 2.1 | 5.467 | 1466 | 216 | 149 | 2330 |
| 54 | 3.2 | 13.9 | 1240 | 422.1 | 108.9 | 1150 |
| 55a | 0.84 | 6.626 | 1077 | 61.65 | 219.3 | 139 |
| 55b | 0.92 | 5.099 | 158.1 | 63.77 | 55.97 | 163.2 |
| 56 | 11.8 | 18.76 | 3398 | 797.9 | 452.1 | 4154 |
| 57a | 3.7 | 10.37 | 367.2 | 365.2 | 331.2 | 2205 |
| 57b | 1.4 | 4.519 | 190.3 | 209.4 | 393.4 | 2233 |
| 58 | 1.9 | 4.5 | >10000 | 1353 | 2829 | 2174 |
| 59 | 1.5 | 4.0 | >10000 | 4526 | 5613 | 1978 |
| 60 | 1.8 | 6.2 | >10000 | 1352 | 53 | 2212 |
| 61 | 1.4 | 7.6 | 4621 | 1050 | 65 | 3246 |
| 62 | 1.3 | 5.2 | >10000 | 575 | 238 | 2718 |
| 63 | 5.0 | 7.5 | 2504 | 4947 | 2613 | 3679 |
| 64 | 1.6 | 4.7 | >10000 | 3546 | 4230 | 3133 |
| 65 | 8.9 | 18.5 | >10000 | 1265 | 9227 | 4900 |
| 66 | 23.8 | 22.4 | 2679 | >10000 | >10000 | >10000 |
| 67 | >100 | 123.0 | >10000 | >10000 | >10000 | 6514 |

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound of formula (I):

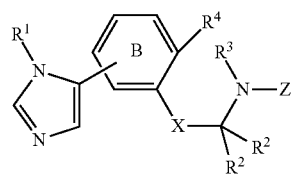
(I)

or a pharmaceutically acceptable salt thereof, wherein:

Z is selected from

H, (1)

$C_1$-$C_6$ alkyl, (2)

—$SO_2$—($C_1$-$C_6$alkyl), (3)

—C(O)—O—($C_1$-$C_6$alkyl), (4)

—C(O)—NH—($C_1$-$C_6$alkyl), (5)

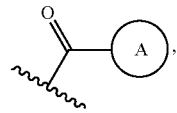, (6)

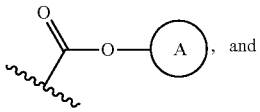, and (8)

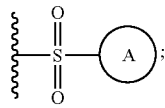; (9)

A is selected from: cyclopropyl, phenyl, benxo[d][1,3]dioxol-5-yl, tetrahydro-2H-pyran-2-yl, thiazolyl, pyridyl and pyrazinyl, each of which can be optionally substituted with up to two $R^5$ groups;

X is a bond or —$CH_2$—;

$R^1$ is

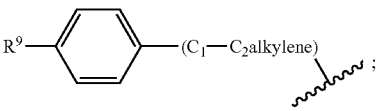

each occurrence of $R^2$ is independently selected from H and $C_1$-$C_6$ alkyl, or two $R^2$ groups on the same carbon atom can be joined together to form a cyclopropyl group;

$R^3$ is selected from H and $C_1$-$C_6$ alkyl, or $R^3$ and an $R^2$ group, together with the atoms to which they are attached, can combine to form a $C_3$-$C_6$ heterocyclic ring;

$R^4$ is H, or $R^3$ and $R^4$ can join together to form a linker group selected from —$CH_2$— and —$CH_2$—$CH_2$, thereby forming a fused bicyclic ring with ring B;

each occurrence of $R^5$ is independently selected from halo, —$OR^8$, —$N(R^6)_2$—, 5 or 6-membered monocyclic heterocycloalkyl or 9 or 10-membered bicyclic heterocycloalkyl, wherein said 5 or 6-membered monocyclic heterocycloalkyl group and said 9 or 10-membered bicyclic heterocycloalkyl group can be optionally substituted on one or more ring carbon atoms with up to two R⁷ groups, which can be the same or different;

each occurrence of R⁶ is independently selected from H, $C_1$-$C_6$ alkyl, —C(O)—$C_1$-$C_6$ alkyl, and —O—($C_1$-$C_6$ alkyl);

each occurrence of R⁷ is independently selected from $C_1$-$C_6$ alkyl, $C_1$-$C_6$ haloalkyl, OR⁸, and —NHCHCH(cyclopropyl)OH;

each occurrence of R⁸ is independently H or $C_1$-$C_6$ alkyl; and

R⁹ is F.

2. The compound of claim 1, having the formula (Ia):

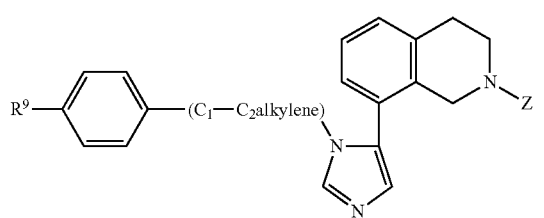

(Ia)

or a pharmaceutically acceptable salt thereof.

3. The compound of claim 2, or a pharmaceutically acceptable salt thereof, wherein:

Z is

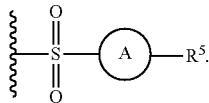

4. The compound of claim 3, or a pharmaceutically acceptable salt thereof, wherein A is thiazol-2-yl or pyridin-3-yl, and R⁵ is selected from —N(H)—C(O)—$C_1$-$C_4$alkyl, 4-methylpiperazin-1-yl, 4-(2-hydroxyethyl)piperazin-1-yl, 4-hydroxypiperidin-1-yl and 7-hydroxyhexadydropyrrolo[1,2-a]pyrazin-2(1H)-yl.

5. The compound of claim 1, having the formula (Ib):

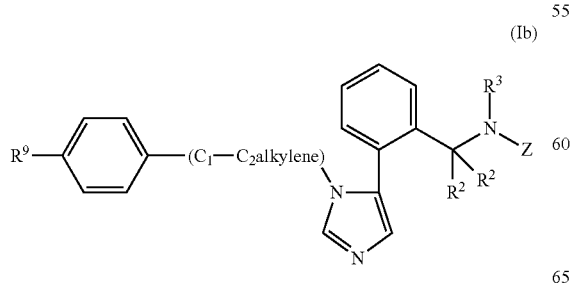

(Ib)

or a pharmaceutically acceptable salt thereof.

6. The compound of claim 5, or a pharmaceutically acceptable salt thereof, wherein:

Z is

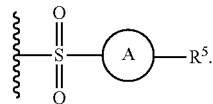

7. The compound of claim 6, or a pharmaceutically acceptable salt thereof, wherein A is thiazol-2-yl or pyridin-3-yl, and R⁵ is selected from —N(H)—C(O)—$C_1$-$C_4$alkyl, 4-methylpiperazin-1-yl, 4-(2-hydroxyethyl)piperazin-1-yl, 4-hydroxypiperidin-1-yl and 7-hydroxyhexadydropyrrolo[1,2-a]pyrazin-2(1H)-yl.

8. The compound of claim 1, having the formula (Ic):

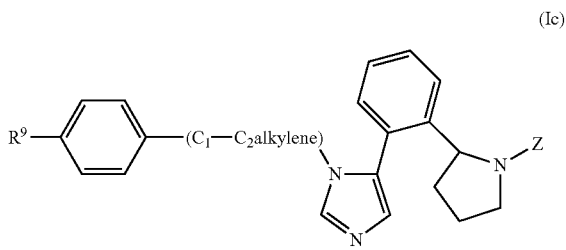

(Ic)

or a pharmaceutically acceptable salt thereof.

9. The compound of claim 8, or a pharmaceutically acceptable salt thereof, wherein:

Z is

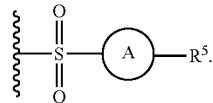

10. The compound of claim 9, or a pharmaceutically acceptable salt thereof, wherein:

A is thiazol-2-yl or pyridin-3-yl, and

R⁵ is selected from —N(H)—C(O)—$C_1$-$C_4$alkyl, 4-methylpiperazin-1-yl, 4-(2-hydroxyethyl)piperazin-1-yl, 4-hydroxypiperidin-1-yl and 7-hydroxyhexadydropyrrolo[1,2-a]pyrazin-2(1H)-yl.

11. The compound of claim 1, having the formula (Id):

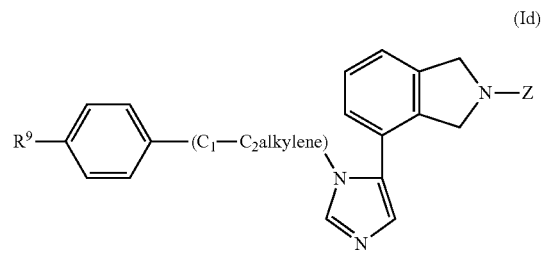

(Id)

or a pharmaceutically acceptable salt thereof.

12. The compound of claim 11, or a pharmaceutically acceptable salt thereof, wherein:
Z is

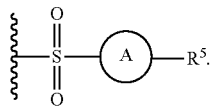

13. The compound of claim 12, or a pharmaceutically acceptable salt thereof, wherein:
A is thiazol-2-yl or pyridin-3-yl, and
$R^5$ is selected from —N(H)—C(O)—$C_1$-$C_4$alkyl, 4-methylpiperazin-1-yl, 4-(2-hydroxyethyl)piperazin-1-yl, 4-hydroxypiperidin-1-yl and 7-hydroxyhexadydropyrrolo[1,2-a]pyrazin-2(1H)-yl.

14. A compound selected from the following:
N-(5-((6-(1-(4-fluorophenethyl)-1H-imidazol-5-yl)-3,4-dihydroisoquinolin-2(1H)-yl)sulfonyl)thiazol-2-yl)acetamide;
(R)-5-((7-(1-(1-(4-fluorophenyl)ethyl)-1H-imidazol-5-yl)-3,4-dihydroisoquinolin-2(1H)-yl)sulfonyl)thiazol-2-amine;
N-(1-(4-(1-(4-fluorophenethyl)-1H-imidazol-5-yl)phenyl)ethyl)-2-(4-methylpiperazin-1-yl)thiazole-5-sulfonamide;
N-(1-(2-(1-(4-fluorophenethyl)-1H-imidazol-5-yl)phenyl)ethyl)-N-methyl-2-(4-methylpiperazin-1-yl)thiazole-5-sulfonamide;
N-((2-(1-(4-fluorophenethyl)-1H-imidazol-5-yl)phenyl)(phenyl)methyl)-2-(4-methylpiperazin-1-yl)thiazole-5-sulfonamide;
N—((R)-1-(2-(1-(4-fluorophenethyl)-1H-imidazol-5-yl)phenyl)ethyl)-2-((7R,8aS)-7-hydroxyhexahydropyrrolo[1,2-a]pyrazin-2(1H)-yl)thiazole-5-sulfonamide;
N—((S)-1-(2-(1-(4-fluorophenethyl)-1H-imidazol-5-yl)phenyl)ethyl)-2-((7R,8aS)-7-hydroxyhexahydropyrrolo[1,2-a]pyrazin-2(1H)-yl)thiazole-5-sulfonamide;
N-(5-(N-(2-(2-(1-(4-fluorophenethyl)-1H-imidazol-5-yl)phenyl)propan-2-yl)sulfamoyl)thiazol-2-yl)acetamide;
N-(5-((2-(4-(1-(4-fluorophenethyl)-1H-imidazol-5-yl)phenyl)pyrrolidin-1-yl)sulfonyl)thiazol-2-yl)acetamide;
5-((2-(4-(1-(4-fluorophenethyl)-1H-imidazol-5-yl)phenyl)pyrrolidin-1-yl)sulfonyl)-2-(4-methylpiperazin-1-yl)thiazole;
(R)—N-(5-(N-(1-(4-(1-(1-(4-fluorophenyl)ethyl)-1H-imidazol-5-yl)phenyl)cyclopropyl)sulfamoyl)thiazol-2-yl)acetamide;
N-(5-(N-((5-(1-(4-fluorophenethyl)-1H-imidazol-5-yl)pyridin-2-yl)methyl)sulfamoyl)thiazol-2-yl)acetamide;
N-(5-(N-(4-(1-(4-fluorophenethyl)-1H-imidazol-5-yl)benzyl)sulfamoyl)thiazol-2-yl)acetamide;
N-(5-(N-(3-(1-(4-fluorophenethyl)-1H-imidazol-5-yl)benzyl)sulfamoyl)thiazol-2-yl)acetamide;
N-(2-(1-(4-fluorophenethyl)-1H-imidazol-5-yl)phenethyl)pyridine-3-sulfonamide;
N-(5-((4-(1-(4-fluorophenethyl)-1H-imidazol-5-yl)isoindolin-2-yl)sulfonyl)thiazol-2-yl)acetamide;
5-((4-(1-(4-fluorophenethyl)-1H-imidazol-5-yl)isoindolin-2-yl)sulfonyl)-2-(4-methylpiperazin-1-yl)thiazole;
N-(2-(1-(4-fluorophenethyl)-1H-imidazol-5-yl)benzyl)pyridine-3-sulfonamide;
N-(5-(N-(2-(1-(4-fluorophenethyl)-1H-imidazol-5-yl)benzyl)sulfamoyl)thiazol-2-yl)acetamide;
N-(2-(1-(4-fluorophenethyl)-1H-imidazol-5-yl)benzyl)-2-((7R,8aS)-7-hydroxyhexahydropyrrolo[1,2-a]pyrazin-2(1H)-yl)thiazole-5-sulfonamide;
N-(5-((2-(2-(1-(2-methoxyethyl)-1H-imidazol-5-yl)phenyl)pyrrolidin-1-yl)sulfonyl)thiazol-2-yl)acetamide;
N-(5-((2-(2-(1-(4-fluorophenethyl)-1H-imidazol-5-yl)phenyl)pyrrolidin-1-yl)sulfonyl)thiazol-2-yl)acetamide;
(7R,8aS)-2-(5-((2-(2-(1-(4-fluorophenethyl)-1H-imidazol-5-yl)phenyl)pyrrolidin-1-yl)sulfonyl)thiazol-2-yl)octahydropyrrolo[1,2-a]pyrazin-7-ol;
1-(4-fluorophenethyl)-5-(2-(1-(methylsulfonyl)pyrrolidin-2-yl)phenyl)-1H-imidazole;
(7R,8aS)-2-(5-((2-(2-(1-methyl-1H-imidazol-5-yl)phenyl)pyrrolidin-1-yl)sulfonyl)thiazol-2-yl)octahydropyrrolo[1,2-a]pyrazin-7-ol;
3-bromo-2-chloro-5-((2-(2-(1-(4-fluorophenethyl)-1H-imidazol-5-yl)phenyl)pyrrolidin-1-yl)sulfonyl)pyridine;
5-(2-(1-(benzo[d][1,3]dioxol-5-ylsulfonyl) pyrrolidin-2-yl)phenyl)-1-(4-fluorophenethyl)-1H-imidazole;
5-(2-(1-((2,5-dimethoxyphenyl)sulfonyl)pyrrolidin-2-yl) phenyl)-1-(4-fluorophenethyl)-1H-imidazole;
5-((2-(2-(1-(4-fluorophenethyl)-1H-imidazol-5-yl)phenyl)pyrrolidin-1-yl)sulfonyl)-N,N-dimethylpyridin-2-amine;
4-(5-((2-(2-(1-(4-fluorophenethyl)-1H-imidazol-5-yl)phenyl)pyrrolidin-1-yl)sulfonyl)pyridin-2-yl)morpholine;
N-(5-((2-(2-(1-methyl-1H-imidazol-5-yl)phenyl)pyrrolidin-1-yl)sulfonyl)thiazol-2-yl)acetamide;
N-(5-((2-(2-(1-cyclopropyl-1H-imidazol-5-yl)phenyl)pyrrolidin-1-yl)sulfonyl)thiazol-2-yl)acetamide;
1-(5-((2-(2-(1-(4-fluorophenethyl)-1H-imidazol-5-yl)phenyl)pyrrolidin-1-yl)sulfonyl)pyridin-2-yl)piperidin-4-ol;
1-cyclopropyl-2-((5-((2-(2-(1-(4-fluorophenethyl)-1H-imidazol-5-yl)phenyl)pyrrolidin-1-yl) sulfonyl)pyridin-2-yl)amino)ethanol;
2-(4-(5-((2-(2-(1-(4-fluorophenethyl)-1H-imidazol-5-yl)phenyl)pyrrolidin-1-yl)sulfonyl)pyridin-2-yl)piperazin-1-yl)ethanol;
4-chlorophenyl 2-(2-(1-(4-fluorophenethyl)-1H-imidazol-5-yl)phenyl)pyrrolidine-1-carboxylate
tert-butyl 2-(2-(1-cyclopropyl-1H-imidazol-5-yl)phenyl) pyrrolidine-1-carboxylate;
tert-butyl 2-(2-(1-(4-fluorophenethyl)-1H-imidazol-5-yl) phenyl)pyrrolidine-1-carboxylate;
isopropyl 2-(2-(1-(4-fluorophenethyl)-1H-imidazol-5-yl) phenyl)pyrrolidine-1-carboxylate;
1-(4-fluorophenethyl)-5-(2-(pyrrolidin-2-yl)phenyl)-1H-imidazole;
(2-(2-(1-(4-fluorophenethyl)-1H-imidazol-5-yl)phenyl) pyrrolidin-1-yl)(tetrahydro-2H-pyran-4-yl)methanone;
(2-(2-(1-(4-fluorophenethyl)-1H-imidazol-5-yl)phenyl) pyrrolidin-1-yl)(pyridin-3-yl)methanone;
(2-(2-(1-(4-fluorophenethyl)-1H-imidazol-5-yl)phenyl) pyrrolidin-1-yl)(6-morpholinopyridin-3-yl)methanone;
cyclopropyl(2-(2-(1-(4-fluorophenethyl)-1H-imidazol-5-yl)phenyl)pyrrolidin-1-yl)methanone;
1-(4-fluorophenethyl)-5-(2-(1-methylpyrrolidin-2-yl) phenyl)-1H-imidazole;
2-(2-(1-(4-fluorophenethyl)-1H-imidazol-5-yl)phenyl)-N-isopropylpyrrolidine-1-carboxamide;
cyclopropyl(2-(3-(1-(4-fluorophenethyl)-1H-imidazol-5-yl)phenyl)pyrrolidin-1-yl)methanone;

(2-(3-(1-(4-fluorophenethyl)-1H-imidazol-5-yl)phenyl)pyrrolidin-1-yl)(pyridin-3-yl)methanone;
(2-(3-(1-(4-fluorophenethyl)-1H-imidazol-5-yl)phenyl)pyrrolidin-1-yl)(tetrahydro-2H-pyran-4-yl)methanone;
2-(3-(1-(4-fluorophenethyl)-1H-imidazol-5-yl)phenyl)-N-isopropylpyrrolidine-1-carboxamide;
1-(4-fluorophenethyl)-5-(3-(1-(methylsulfonyl)pyrrolidin-2-yl)phenyl)-1H-imidazole;
(2-(3-(1-(4-fluorophenethyl)-1H-imidazol-5-yl)phenyl)pyrrolidin-1-yl)(6-morpholinopyridin-3-yl)methanone;
5-(3-(1-((2,5-dimethoxyphenyl)sulfonyl)pyrrolidin-2-yl)phenyl)-1-(4-fluorophenethyl)-1H-imidazole;
3-Bromo-2-chloro-5-((2-(3-(1-(4-fluorophenethyl)-1H-imidazol-5-yl)phenyl)pyrrolidin-1-yl)sulfonyl)pyridine;
N-((5-((2-(3-(1-(4-fluorophenethyl)-1H-imidazol-5-yl)phenyl)pyrrolidin-1-yl)sulfonyl)thiophen-2-yl)methyl)benzamide;
Isopropyl 2-(3-(1-(4-fluorophenethyl)-1H-imidazol-5-yl)phenyl)pyrrolidine-1-carboxylate;
1-(5-((2-(3-(1-(4-fluorophenethyl)-1H-imidazol-5-yl)phenyl)pyrrolidin-1-yl)sulfonyl)pyridin-2-yl)piperidin-4-ol;
5-((5-(1-(4-fluorophenethyl)-1H-imidazol-5-yl)-3,4-dihydroisoquinolin-2(1H)-yl)sulfonyl)-2-(4-methylpiperazin-1-yl)thiazole;
5-(1-(4-fluorophenethyl)-1H-imidazol-5-yl)-2-((6-(4-methylpiperazin-1-yl)pyridin-3-yl)sulfonyl)-1,2,3,4-tetrahydroisoquinoline;
4-(5-((5-(1-(4-fluorophenethyl)-1H-imidazol-5-yl)-3,4-dihydroisoquinolin-2(1H)-yl)sulfonyl)pyridin-2-yl)morpholine;
5-((5-(1-(4-fluorophenethyl)-1H-imidazol-5-yl)-3,4-dihydroisoquinolin-2(1H)-yl)sulfonyl)-N,N-dimethylpyridin-2-amine;
5-((5-(1-(4-fluorophenethyl)-1H-imidazol-5-yl)-3,4-dihydroisoquinolin-2(1H)-yl)sulfonyl)-N-(2-methoxyethyl)-N-methylpyridin-2-amine;
(7R,8aS)-2-(5-((5-(1-((R)-1-(4-fluorophenyl)ethyl)-1H-imidazol-5-yl)-3,4-dihydroisoquinolin-2(1H)-yl)sulfonyl)thiazol-2-yl)octahydropyrrolo[1,2-a]pyrazin-7-ol;
(7R,8aS)-2-(5-((5-(1-(4-fluorophenethyl)-1H-imidazol-5-yl)-3,4-dihydroisoquinolin-2(1H)-yl)sulfonyl)thiazol-2-yl)octahydropyrrolo[1,2-a]pyrazin-7-ol;
(7R,8aS)-2-(5-((8-(1-(4-fluorophenethyl)-1H-imidazol-5-yl)-3,4-dihydroisoquinolin-2(1H)-yl)sulfonyl)thiazol-2-yl)octahydropyrrolo[1,2-a]pyrazin-7-ol;
5-((4-(1-(4-fluorophenethyl)-1H-imidazol-5-yl)-5,6-dihydro-1,7-naphthyridin-7(8H)-yl)sulfonyl)-2-(4-methylpiperazin-1-yl)thiazole; and
5-((4-(1-(4-fluorophenethyl)-1H-imidazol-5-yl)-5,6-dihydropyrido[3,4-d]pyrimidin-7(8H)-yl)sulfonyl)-2-(4-methylpiperazin-1-yl)thiazole;
or a pharmaceutically acceptable salt of any of the foregoing compounds.

15. A pharmaceutical composition comprising an effective amount of a compound of claim 1, or a pharmaceutically acceptable salt thereof, and a pharmaceutically acceptable carrier.

16. The pharmaceutical composition of claim 15, further comprising an anti-HIV drug.

17. A method for improving the pharmacokinetics of a therapeutic compound that is metabolized by a CYP3A enzyme in subject, said method comprising administering to said subject in need of such treatment a combination of: (a) said therapeutic compound that is metabolized by a CYP3A enzyme and (b) a compound of claim 1, or a pharmaceutically acceptable salt thereof.

* * * * *